United States Patent
Hong et al.

(10) Patent No.: US 9,212,258 B2
(45) Date of Patent: Dec. 15, 2015

(54) AMPHIPHILIC DENDRON-COILS, MICELLES THEREOF AND USES

(75) Inventors: Seungpyo Hong, Naperville, IL (US); Jin Woo Bae, Suwon (KR)

(73) Assignee: THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 0 days.

(21) Appl. No.: 14/001,115

(22) PCT Filed: Feb. 22, 2012

(86) PCT No.: PCT/US2012/026133
§ 371 (c)(1),
(2), (4) Date: Oct. 25, 2013

(87) PCT Pub. No.: WO2012/116073
PCT Pub. Date: Aug. 30, 2012

(65) Prior Publication Data
US 2014/0037747 A1    Feb. 6, 2014

Related U.S. Application Data

(60) Provisional application No. 61/445,627, filed on Feb. 23, 2011.

(51) Int. Cl.
| | | |
|---|---|---|
| *C08G 63/91* | (2006.01) | |
| *A61K 9/50* | (2006.01) | |
| *C12Q 1/02* | (2006.01) | |
| *A61K 9/107* | (2006.01) | |
| *A61K 47/44* | (2006.01) | |
| *C08G 63/66* | (2006.01) | |
| *G01N 33/574* | (2006.01) | |
| *A61K 31/352* | (2006.01) | |
| *A61K 31/405* | (2006.01) | |
| *C08G 81/00* | (2006.01) | |
| *C08G 83/00* | (2006.01) | |

(52) U.S. Cl.
CPC ............ *C08G 63/912* (2013.01); *A61K 9/1075* (2013.01); *A61K 9/5031* (2013.01); *A61K 31/352* (2013.01); *A61K 31/405* (2013.01); *A61K 47/44* (2013.01); *C08G 63/66* (2013.01); *C08G 81/00* (2013.01); *C08G 83/004* (2013.01); *C08G 83/008* (2013.01); *C12Q 1/02* (2013.01); *G01N 33/574* (2013.01)

(58) Field of Classification Search
None
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,472,509 A | 9/1984 | Gansow et al. |
| 5,021,236 A | 6/1991 | Gries et al. |

FOREIGN PATENT DOCUMENTS

| | | |
|---|---|---|
| WO | WO-2004/039957 A2 | 5/2004 |
| WO | WO-2006/133099 A2 | 12/2006 |
| WO | WO-2010/018286 A1 | 2/2010 |
| WO | WO-2010/124227 A2 | 10/2010 |
| WO | WO-2011/009991 A2 | 1/2011 |

OTHER PUBLICATIONS

Kim et al. "Methoxy poly(ethylene glycol) and e-caprolactone amphiphilic block copolymeric micelle containing indomethacin". Journal of Controlled Release 51 1998 p. 13-22.*
Lee et al. "Temperature-triggered reversible micellar self-assembly of linear-dendritic block copolymers". Chem. Commun. 2008 pp. 3726-3728.*
Qui "Polymer Architecture and Drug Delivery". Pharmaceutical Research, vol. 23, No. 1, Jan. 2006.*
Sigma-Aldrich "Nanomaterials Dendrons" Oct. 30, 2008.*
Sutton et al. "Functionalized Micellar Systems for Cancer Targeted Drug Delivery". Pharmaceutical Research, vol. 24, No. 6 Jun. 2007 p. 1029-1046.*
Hua et al. "Synthesis and Characterization of Linear-Dendron Like poly(e-caprolactone)-b-poly(etheyne oxide) copolymers via the combination of Ring-Opening Polymerization and Click Chemistry" (2008).*
Al-Jamal et al., Supramolecular structures from dendrons and dendrimers, Adv. Drug Deliv. Rev., 57(15):2238-70 (2005).
Becher et al., Nonionic Surfactants Physical Chemistor, New York: Marcel Dekker (1987).
Binder et al., 'Click' Chemistry in Polymer and Material Science: An Update, Macromol. Rapid Commun., 29(12-13):952-81 (2008).
Bodine et al., Synthesis of readily modifiable cyclodextrin analogues via cyclodimerization of an alkynyl-azido trisaccharide, J. Am. Chem. Soc., 126(6):1638-9 (2004).
Chen et al., A precise packing sequence for self-assembled convex structures, Proc. Natl. Acad. Sci. USA, 104(3):717-22 (2007).
Cho et al., Mesophase structure-mechanical and ionic transport correlations in extended amphiphilic dendrons, Science, 305(5690):1598-601 (2004).
Christiansen et al., Additivity and the Physical Basis of Multivalency Effects: A Thermodynamic Investigation of the Calcium EDTA Interaction, J. Am. Chem. Soc., 125(24):7357-66 (2003).
Chung et al., Self-assembling behavior of amphiphilic dendron coils in the bulk crystalline and liquid crystalline states, J. Am. Chem. Soc., 130:7139-47 (2008).
Ewald, Ann. Phys., 64:253 (1921).
Forrest et al., In vitro release of the mTOR inhibitor rapamycin from poly(ethylene glycol)-b-poly(epsilon-caprolactone) micelles, J. Control. Release, 110(2):370-7 (2006).

(Continued)

*Primary Examiner* — Robert A Wax
*Assistant Examiner* — Danah Al-Awadi
(74) *Attorney, Agent, or Firm* — Marshall, Gerstein & Borun LLP

(57) ABSTRACT

The invention generally relates to the fields of drug delivery and cell capture. In particular, the invention relates to amphiphilic dendron-coils, micelles thereof and their use for drug delivery vehicles and/or cell capture.

16 Claims, 25 Drawing Sheets

(56) References Cited

OTHER PUBLICATIONS

Gaucher et al., Block copolymer micelles: preparation, characterization and application in drug delivery, J. Control. Release, 109(1-3):169-88 (2005).

Ge et al., Responsive supramolecular gels constructed by crown ether based molecular recognition, Angew. Chem. Int. Ed. Engl., 48(10):1798-802 (2009).

Gestwicki et al., Selective immobilization of multivalent ligands for surface plasmon resonance and fluorescence microscopy, Anal. Biochem., 305(2):149-55 (2002).

Gillies et al., Designing Macromolecules for Therapeutic Applications: Polyester DendrimerPoly(ethylene oxide) "Bow-Tie" Hybrids with Tunable Molecular Weight and Architecture, J. Am. Chem. Soc., 124(47):14137-46 (2002).

Gillies et al., Stimuli-Responsive Supramolecular Assemblies of Linear-Dendritic Copolymers, J. Am. Chem. Soc., 126(38):11936-43 (2004).

Harada et al., Supramolecular assemblies of block copolymers in aqueous media as nanocontainers relevant to biological applications, Prog. Polymer Sci., 31(11):949-82 (2006).

Hong et al., Covalent immobilization of p-selectin enhances cell rolling, Langmuir, 23(14):12261-8 (2007).

Hong et al., Interaction of poly(amidoamine) dendrimers with supported lipid bilayers and cells: hole formation and the relation to transport, Bioconjug. Chem., 15(4):774-82 (2004).

Hong et al., Interaction of polycationic polymers with supported lipid bilayers and cells: nanoscale hole formation and enhanced membrane permeability, Bioconjug. Chem., 17(3):728-34 (2006).

Hong et al., The binding avidity of a nanoparticle-based multivalent targeted drug delivery platform, Chem. Biol., 14(1):107-15 (2007).

Hua et al., Versatile strategy for the synthesis of dendronlike polypeptide/linear poly(epsilon-caprolactone) block copolymers via click chemistry, Biomacromolecules, 10(5):1140-8 (2009).

Humphrey et al., VMD: Visual molecular dynamics, J. Mol. Graphics, 1491):33-8 (1996).

International Preliminary Report on Patentability, corresponding International Application No. PCT/US2012/026133, Aug. 27, 2013.

International Search Report and Written Opinion, corresponding International Application No. PCT/US2012/026133, mailing date Dec. 27, 2012.

Israelachvili et al., Theory of self-assembly of hydrocarbon amphiphiles into micelles and bilayers, J. Chem. Soc., Faraday Trans. 3, 72:1525-68 (1976).

Israelachvili, Intermolecular and Surface Forces, San Diego: Academic Press Inc. (1995).

Joralemon et al., Shell Click-Crosslinked (SCC) Nanoparticles: A New Methodology for Synthesis and Orthogonal Functionalization, J. Am. Chem. Soc., 127(48):16892-9 (2005).

Kellermann et al., The first account of a structurally persistent micelle, Angew. Chem. Int. Ed. Engl., 43(22):2959-62 (2004).

Kim et al., Hydrophilic matrix-assisted ionic transportation in the columnar assembly of amphiphilic dendron-coils, Chem. Eur. J., 15:8683-6 (2009).

Kim et al., Methoxy poly(ethylene glycol) and epsilon-caprolactone amphiphilic block copolymeric micelle containing indomethacin. II. Micelle formation and drug release behaviours, J. Control. Release, 51(1):13-22 (1998).

Kitov et al., On the Nature of the Multivalency Effect: A Thermodynamic Model, J. Am. Chem. Soc., 125(52):16271-84 (2003).

Kong et al., Quantifying the relation between adhesion ligand-receptor bond formation and cell phenotype, Proc. Natl. Acad. Sci. USA, 103(49):18534-9 (2006).

Kostiainen et al., High-affinity multivalent DNA binding by using low-molecular-weight dendrons, Angew. Chem. Int. Ed. Engl., 44(17):2556-9 (2005).

Kostiainen et al., Precisely defined protein-polymer conjugates: construction of synthetic DNA binding domains on proteins by using multivalent dendrons, ACS Nano, 1(2):103-13 (2007).

Kratzat et al., Influence of the Molecular Geometry of Nonionic Surfactants on Surface and Micellar Properties in Aqueous Solutions, Langmuir, 12(7):1765-70 (1996).

Lee et al., Molecular Dynamics Studies of Polyethylene Oxide and Polyethylene Glycol: Hydrodynamic Radius and Shape Anisotropy, Biophysical J., 95(4):1590-9 (2008).

Lee et al., Temperature-triggered reversible micellar self-assembly of linear-dendritic block copolymers, Chem. Commun. (Camb.), 32:3726-8 (2008).

Leroueil et al., Nanoparticle interaction with biological membranes: does nanotechnology present a Janus face?, Acc. Chem. Res., 40(5):335-42 (2007).

Liu et al., In vivo fate of unimers and micelles of a poly(ethylene glycol)-block-poly(caprolactone) copolymer in mice following intravenous administration, Eur. J. Pharm. Biopharm., 65(3):309-19 (2007).

Low et al., Discovery and development of folic-acid-based receptor targeting for imaging and therapy of cancer and inflammatory diseases, Acc. Chem. Res., 41(1):120-9 (2008).

Lu et al., Aggregation behavior of MPEG-PCL diblock copolymers in aqueous solutions and morphologies of the aggregates, J. Polymer Sci. Polymer Phys., 44:3406-17 (2006).

MacKerell et al., All-Atom Empirical Potential for Molecular Modeling and Dynamics Studies of Proteins, J. Phys. Chem. B, 102(18):3586-616 (1998).

McNerny et al., RGD dendron bodies; synthetic avidity agents with defined and potentially interchangeable effector sites that can substitute for antibodies, Bioconjug. Chem., 20(10):1853-9 (2009).

Myung et al., Dendrimer-mediated multivalent binding for the enhanced capture of tumor cells, Angew. Chem. Int. Ed. Engl., 50(49):1 1769-72 (2011).

Nagarajan, Molecular Packing Parameter and Surfactant Self-Assembly: The Neglected Role of the Surfactant Tail, Langmuir, 18(1):31-8 (2002).

Nagrath et al., Isolation of rare circulating tumour cells in cancer patients by microchip technology, Nature, 450(7173):1235-9 (2007).

Nandivada et al., Click Chemistry: Versatility and Control in the Hands of Materials Scientists, Adv. Mater., 19(17):2197-208 (2007).

Oerlemans et al., Polymeric micelles in anticancer therapy: targeting, imaging and triggered release, Pharm. Res., 27(12):2569-89 (2010).

Papp et al., Inhibition of influenza virus infection by multivalent sialic-acid-functionalized gold nanoparticles, Small, 6(24):2900-6 (2010).

Parker et al., Folate receptor expression in carcinomas and normal tissues determined by a quantitative radioligand binding assay, Anal. Biochem., 338(2):284-93 (2005).

Peer et al., Nanocarriers as an emerging platform for cancer therapy, Nat. Nanotechnol., 2(12):751-60 (2007).

Philips et al., Scalable molecular dynamics with NAMD, J. Computational Chem., 26:1781 (2005).

Posocco et al., Morphology prediction of block copolymers for drug delivery by mesoscale simulations, J. Mater. Chem., 20:7742-53 (2010).

Qiu et al., Polymer architecture and drug delivery, Pharm. Res., 23(1):1-30 (2006).

Riley et al., Physicochemical Evaluation of Nanoparticles Assembled from Poly(lactic acid)-Poly(ethylene glycol) (PLA-PEG) Block Copolymers as Drug Delivery Vehicles, Langmuir, 17(11):3168-74 (2001).

Riva et al., Combination of Ring-Opening Polymerization and "Click Chemistry": Toward Functionalization and Grafting of Poly(?-caprolactone), Macromolecules, 40(4):796-803 (2007).

Rosen et al., Dendron-mediated self-assembly, disassembly, and self-organization of complex systems, Chem. Rev., 109(11):6275-540 (2009).

Sun et al., Biodegradable micelles with sheddable poly(ethylene glycol) shells for triggered intracellular release of doxorubicin, Biomaterials, 30(31):6358-66 (2009).

Sutton et al., Functionalized micellar systems for cancer targeted drug delivery, Pharm. Res., 24(6):1029-46 (2007).

Tanford, The Hydrophobic Effect: Formation of Micelles and Biological Membranes, New York: Wiley Sons (1973).

(56) References Cited

OTHER PUBLICATIONS

Tian et al., Vesicular self-assembly of comb-dendritic block copolymers, Chem. Commun. (Camb.), 33:3489-91 (2006).

Urbani et al., Self-Assembly of Amphiphilic Polymeric Dendrimers Synthesized with Selective Degradable Linkages, Macromolecules, 41(1):76-86 (2008).

Vanommeslaeghe et al., CHARMM general force field: A force field for drug-like molecules compatible with the CHARMM all-atom additive biological force fields, J. Comput. Chem., 31(4):671-90 (2010).

Ward, Mechanical Properties of Solid Polymers, New York: John Wiley and Sons (1971).

Whitesides et al., Molecular self-assembly and nanochemistry: a chemical strategy for the synthesis of nanostructures, Science, 254(5036):1312-9 (1991).

Wilheim et al., Poly(styrene-ethylene oxide) block copolymer micelle formation in water: a fluorescence probe study, Macromolecules, 24(5):1033-40 (1991).

Wiradharma et al., Self-assembled polymer nanostructures for delivery of anticancer therapeutics, Nano Today, 4(4):302-17 (2009).

Yang et al., Aggregation behavior of self-assembling polylactide/poly(ethylene glycol) micelles for sustained drug delivery, Int. J. Pharm., 394(1-2):43-9 (2010).

Yoo et al., Biodegradable polymeric micelles composed of doxorubicin conjugated PLGA-PEG block copolymer, J. Control. Release, 70(1-2):63-70 (2001).

Yoshimoto et al., Binding enhancement of antigen-functionalized PEGylated gold nanoparticles onto antibody-immobilized surface by increasing the functionalized antigen using alpha-sulfanyl-omega-amino-PEG, Chem. Commun. (Camb.), 42:5369-71 (2008).

Zhou et al., Micellization of amphiphilic star polymers with poly(ethylene oxide) arms in aqueous solutions, Langmuir, 9(11):2907-13 (1993).

* cited by examiner (A)

A                                      B

AMPHIPHILIC DENDRON-COILS, MICELLES THEREOF AND USES

This application claims the benefit of U.S. Provisional Patent Application No. 61/445,627 filed Feb. 23, 2011. The provisional application is hereby incorporated by reference in its entirety.

FIELD OF THE INVENTION

The invention generally relates to the fields of drug delivery and cell capture. In particular, the invention relates to amphiphilic dendron-coils and their use for drug delivery and/or cell capture.

BACKGROUND

Drug delivery is a scientific and pharmaceutical field that encompasses the design, synthesis, and use of products that deliver drugs to patients. Goals for such products can include, targeting a drug to a particular location in the patient, protecting a drug against premature degradation, diminishing adverse side effects of a drug, and sustained release of a drug. Polymeric micelles are products that have been pursued as drug delivery vehicles. Polymeric micelles are small, spherical particles (<200 nm in diameter) made up of polymer chains. The polymer chains of polymeric micelles are block copolymers (i.e., typically linear polymers that are composed of repeating blocks of two polymers that differ in hydrophilicity, charge or polarity). Some block copolymers that are amphiphilic block copolymers self-assemble into micelles when placed in an appropriate solvent.

Self-assembled polymeric micelles represent one of the most promising, versatile platforms for drug delivery. Their nanostructural features, such as thermodynamic stability, size, and shape of self-assemblies, can be widely manipulated depending on both amphiphilicity of materials and fabrication techniques. Self-assembly is a process in which a stable ordered ensemble of molecules is formed through the balancing of attractive and repulsive forces between amphiphiles at a concentration above the critical micelle concentration (CMC).[1] One of the most promising types of block copolymers capable of self-assembling is the dendron-coil (DC).[2] A DC is comprised of a flexible linear polymer dendronized at one end in which amphiphilicity can be engineered through the appropriate choice of hydrophilic and hydrophobic blocks. The highly branched, controlled molecular architecture of the dendron allows the unique properties of dendrimers such as monodispersity, precise control of peripheral functional groups, and multivalency to be integrated.[3]

Many groups have reported amphiphilic DCs and other dendron-based copolymers capable of self-assembling into a wide variety of morphologies.[2] Particularly, amphiphilic DCs containing a single hydrophobic peptide block and multiple hydrophilic blocks combined through mediation by a dendron have been shown to preferentially self-assemble into spherical micelles with sizes less than 100 nm.[4]

Over the past decade, significant advances have been made in the development of polymeric micelles to treat and detect cancer effectively[5] and various design strategies have been implemented to enhance cancer targeting.[6,7] The hydrophilic-lipophilic balance (HLB) between polymer chains is a crucial factor used to describe the self-assembly behavior of polymers and is strongly associated with the degree of micellar dissociation and blood circulation time augmenting the enhanced permeability and retention (EPR) effect. In addition, by controlling the HLB it has been shown that a variety of morphologies can be induced (e.g. vesicular, spherical, cylindrical micelles) via self assembly as a result of the interplay between thermodynamic forces.[8] A well-defined density of targeting ligands on the surface and their adopted geometry are also important to produce enhanced selective binding to cancer tissues as supported by recent studies on multivalent cancer targeting.[9,10] In this regard, a dendron, a segment of a dendrimer, is a unique material that not only retains the properties of its parent dendrimer (symmetry and monodispersity) but through distinctive chemical modifications of its focal point and periphery can be hybridized with other materials to create amphiphilic structures that self-assemble and exhibit unique biological responses[11].

In Oerlemans et al. 2010[5], the authors review research and clinical trials on polymeric micelles in anticancer therapy. In Table 1 on page 2571, the review article reports that five micelle products for anticancer therapy had been investigated in clinical trials, one of which (Genexol-PM) has been granted FDA approval to be used in patients with breast cancer. In Table VII on page 2583, the review article lists various multifunctional micellar formulations, including a EGF-receptor-targeted PEG-b-PCL micelles labeled with $^{111}$I and a micellar formulation consisting of folate-conjugated PEG-b-PCL loaded with doxorubicin and SPIONS, that combine two or more the functions of targeting ligands, imaging agents and triggered release. At the end of its "Conclusion and Future Perspectives" section on page 2583, the authors state that "the versatility of micelle-based drug delivery and the large number of promising preclinical studies describing numerous approaches to optimize these nanomedicines will bring the development of a magic bullet a major step forward. Now it is time to bring this potential into clinical practice."

Detecting and/or capturing cells is another field that is important for cancer medicine. For example, although recent advances in diagnostic and therapeutic methods to treat primary tumors have resulted in a decrease in mortality from cancer over the past two years, metastasis of cancer still poses a great challenge as patients often relapse. Disseminated and Circulating tumor cells (DTCs and CTCs respectively) are known to induce secondary tumor formation at distant sites from primary tumors, known as metastasis. Research efforts on diagnosis and prognosis of metastatic cancer have been concentrated on detection of DTCs in bone marrow (BM) and CTCs in blood. Detection of DTCs requires aspiration of BM—a process that is invasive, time-consuming, and often painful for the patients, precluding repeated samplings that are necessary for prognosis studies along with therapeutic treatments. Consequently, effective detection of CTCs in peripheral blood of cancer patients holds a promise as an alternative due to its minimal invasiveness and easy sampling (i.e., blood drawing). However, the detection of CTCs has not yet been implemented for routine clinical practice. Unlike DTCs in BM that are relatively easy to enrich using Ficoll-based assays or the OncoQuick approach, or other immunomagnetic enrichment procedures, CTCs are extremely rare (estimated to be in the range of one tumor cell in the background of 106-109 normal blood cells), presenting a tremendous challenge for efficient, clinically significant detection of CTCs.

Thus, there exists in the art a need for products and methods to efficiently detect and/or capture circulating tumor cells, and to deliver drugs to target cells.

SUMMARY

The present invention provides amphiphilic dendron-coils, micelles thereof and their use for drug delivery and/or cell-capture. Micelles according to the invention comprise amphiphilic dendron-coils. In turn, each amphiphilic dendron-coil comprises a non-peptidyl, hydrophobic core-forming block, a polyester dendron and a poly(ethylene) glycol (PEG) moiety. The non-peptidyl, hydrophobic core-forming block is a linear hydrophobic polymer, for example, a polycaprolactone (PCL), poly(lactic acid) (PLA), poly(glycolic acid) (PGA) or poly(lactic-co-glycolic acid) (PLGA). The polyester dendron is, for example, a generation 3 (G3) to generation 5 (G5) polyester dendron with either an acetylene or carboxylate core. The PEG moiety is, for example, a methoxy PEG (mPEG) moiety, amine-terminated PEG (PEG-$NH_2$) moiety, acetylated PEG (PEG-Ac) moiety, carboxylated PEG (PEG-COOH) moiety, thiol-terminated PEG (PEG-SH) moiety, N-hydroxysuccinimide-actived PEG (PEG-NHS) moiety, $NH_2$-PEG-$NH_2$ moiety or $NH_2$-PEG-COOH moiety. The micelles comprising amphiphilic dendron-coils are also referred to as "multivalent dendron conjugates" and "dendron-based nanomicelles (DNMs)" at various places in the Examples herein. The invention also provides the amphiphilic dendron-coils.

The polyester dendron is covalently modified with the linear hydrophobic polymer to help to facilitate chain entanglement and intramolecular interactions which aid in the self-assembly of core-shell type micelles and enable hydrophobic drug molecules to be loaded within the micelles. The PEG moieties form a hydrophilic corona with non-fouling properties and afford increased circulation half-life when the micelles are administered in vivo.

Biologically important properties such as biodegradability, circulation half-life, targetability, pharmacokinetics and drug release can be controlled by varying the three components (also referred to as the three polymer blocks) of the amphiphilic dendron-coils. Moreover, the copolymer structure is flexible and can be easily manipulated by varying the molecular weights of each component to fine-tune the hydrophilic-lipophilic balances (HLBs). For example, various embodiments of the invention employ PCL, polyester dendron, and PEG with molecular weights ranging 0.5-20 kDa, G3-G5 (~0.9-3.5 kDa), and 0.2-5 kDa, respectively. The HLBs (20 $M_H/(M_H+M_L)$, where $M_H$ is the mass of the hydrophilic block and $M_L$ is the mass of the lipophilic block) therefore widely vary from 2.22 to 19.94.

The micelles also exploit the unique structural benefits of their dendron components. Unlike linear polymers, a dendron offers multiple surface groups enabling multivalent interactions with other molecules. Multivalent interactions are beneficial for targeting[12] and capturing[13] uses. The multiple surface groups can be conjugated with virtually any biologically active molecule such as targeting, imaging, and therapeutic agents/drugs. Amphiphilic dendon-coils of the invention with different components can be mix-and-matched in the self-assembly process of micelles to, for example, integrate targeting, imaging and/or drug delivery (including delivery of single, dual or multiple drugs) functions in a single micelle preparation.

When a dendron is co-polymerized with the hydrophobic linear polymer [such as polycaprolactone (PCL), poly(lactic acid) (PLA), poly(glycolic acid) (PGA), and poly(lactic-co-glycolic acid) (PLGA)] in generation of the amphiphilic dendron-coils of the invention, the cone-shaped, amphiphilic dendron-coils in turn possess advantageous structural attributes because they form self-assembled micelles, which are thermodynamically favorable and have highly packed PEG surface layers for increased blood circulation time. The thermodynamic stability in forming micelles, along with the unique architecture that is easily tunable, makes the amphiphilic dendron-coils and their self-assembled micellar structures ideal for use as a drug delivery platform and in a cell-capture system.

The present invention also provides compositions comprising a micelle comprising amphiphilic dendron-coils, wherein each amphiphilic dendron-coil comprises a non-peptidyl, hydrophobic core-forming block, a polyester dendron and a poly(ethylene) glycol (PEG) moiety.

Also provided is methods of delivering a drug (or drugs) to a patient comprising administering a composition comprising a micelle and a pharmaceutically acceptable carrier, wherein the micelle comprises amphiphilic dendron-coils and encapsulates the drug, and wherein each amphiphilic dendron-coil comprises a non-peptidyl, hydrophobic core-forming block, a polyester dendron and a poly(ethylene) glycol (PEG) moiety.

The present invention also provides methods and devices for capturing a cell from a sample. The methods comprising the steps of: exposing the sample to an immobilized amphiphilic dendron-coil comprising a non-peptidyl, hydrophobic core-forming block, a polyester dendron and a poly (ethylene) glycol (PEG) moiety with a ligand conjugated to the PEG, wherein the ligand binds to the cell; and capturing the cell by binding of the ligand to the cell.

DETAILED DESCRIPTION

Figure 1:
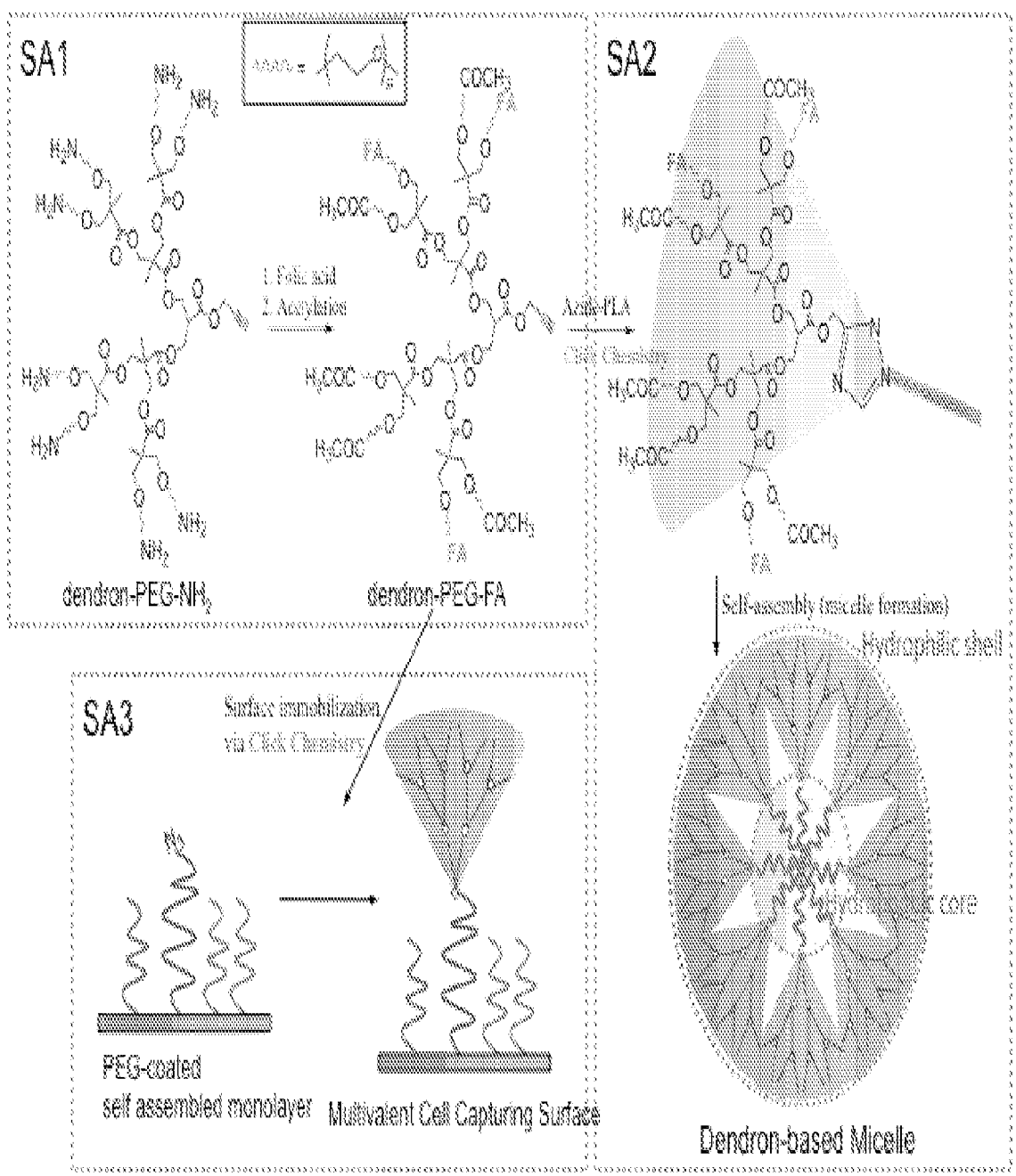
FIG. 1 shows a general overview of exemplary folic acid-conjugated amphiphilic dendron-coils and uses thereof.

In a first aspect, the invention provides micelles comprising amphiphilic dendron-coils and provides the amphiphilic dendron-coils. The amphiphilic dendron-coils each comprise three components: a non-peptidyl, hydrophobic core-forming block, a polyester dendron and a poly(ethylene) glycol (PEG) moiety. The hydrophobic core-forming block of the micelles is non-peptidyl, that is, the hydrophobic core-forming block is not a peptide. In some embodiments of the invention, a micelle comprises a single type of amphilphilic dendron-coil (i.e., the amphiphilic dendron-coils in the micelle all have the same three components.) In some embodiments of the invention, a micelle comprises more than one type of amphiphilic dendron-coil (i.e., the amphiphilic dendon-coils in the micelle vary in their three components.)

In some embodiments, the non-peptidyl, hydrophobic core-forming block of the amphiphilic dendron-coil comprises polycaprolactone (PCL), poly(lactic acid) (PLA), poly (glycolic acid) (PGA) or poly(lactic-co-glycolic acid) (PLGA). In some embodiments, the non-peptidyl, hydrophobic core-forming block is PCL. In some embodiments, the PCL is poly(ε-caprolactone). In some embodiments, the non-peptidyl, hydrophobic core-forming block is PLA. In some embodiments, the non-peptidyl, hydrophobic core-forming block is PGA. In some embodiments, the non-peptidyl, hydrophobic core-forming block is PLGA. The non-peptidyl, hydrophobic core-forming block has a molecular weight including, but not limited to, a molecular weight from about 0.5 kDa to about 20 kDa. In some embodiments, the non-peptidyl, hydrophobic dore-forming block is poly(ε-caprolactone) with a molecular weight of about 3.5 kDa. In some embodiments, the non-peptidyl, hydrophobic dore-forming block is poly(ε-caprolactone) has a molecular weight of 14 kDa. In some embodiments, the amphiphilic dendron-coils those disclosed in Example 2.

In some embodiments, the polyester dendron of the amphiphilic dendron-coil includes, but is not limited to, a generation 3 to generation 5 [that is, a generation 3 (G3), a generation 4 (G4) or a generation 5 (G5)] polyester dendron with either an acetylene or carboxylate core. In some embodiments, the polyester dendron is a G3 dendron. In some embodiments, the polyester dendron is a G5 dendron. In some embodiments, the polyester dendron has an acetylene core. In some embodiments, the polyester dendron is generation 3 polyester-8-hydroxyl-1-acetylene bis-MPA dendron. In some embodiments, the polyester dendron has a carboxylate core. Methods of preparing and characterizing dendrons are well known in the art, and various polyester dendrons useful in the invention may be purchased from commercial entities.

In some embodiments, the PEG moiety of the amphiphilic dendron-coil is a methoxy PEG (mPEG) moiety, amine-terminated PEG (PEG-NH$_2$) moiety, acetylated PEG (PEG-Ac) moiety, carboxylated PEG (PEG-COOH) moiety, thiol-terminated PEG (PEG-SH) moiety, N-hydroxysuccinimide-activated PEG (PEG-NHS) moiety, NH$_2$-PEG-NH$_2$ moiety or NH$_2$-PEG-COOH moiety. In some embodiments, the PEG moiety has a molecular weight including, but not limited to, a molecular weight from about 0.2 kDa to about 5 kDa. In some embodiments, the PEG moiety is a mPEG moiety. In some embodiments, the PEG moiety is an mPEG moiety with a molecular weight of about 2 kDa. In some embodiments, the PEG moiety is an mPEG moiety with a molecular weight of about 5 kDa.

In some embodiments, the micelles of the invention encapsulate or, in other words, are loaded with one or more drugs. Drugs contemplated by the invention are discussed in more detail below. In some embodiments, the drug is a cancer drug (i.e., a drug used to treat cancer). In some embodiments, the drug is an anti-inflammatory drug including, but not limited to, indomethacin. In some embodiments, the drug is α-mangostin. The drug α-mangostin has been reported to have anti-oxidant, anti-bacterial, anti-cancer/anti-tumor and anti-allergy properties.

A "drug" is a compound that, upon administration to a patient (including, but not limited to, a human or other animal) in a therapeutically effective amount, provides a therapeutic benefit to the patient. Those skilled in the art will appreciate that the term "drug" is not limited to drugs that have received regulatory approval.

Drugs contemplated by the invention include, but are not limited to, small organic molecules, RNA, DNA, proteins, chemicals or peptides to block transcription, translation, intracellular signaling cascades, enzymes (kinases), proteosome activity, lipid metabolism, cell cycle, and membrane trafficking. Drugs include agents that target proinflammatory mediators such as cytokine and chemokine genes, enzymes involved in generation of inflammatory mediators, receptors for cytokines, chemokines, lipid mediators, apoptosis, cytoplasmic signaling molecules involved in inflammatory cascades, e.g., NF-κB, STAT, Talin, Rap-1; tissue injury such as apoptosis, e.g., caspase, bcl-2; molecules important for cell activation and proliferation, e.g., cyclins, kinesin Eg5; molecules important for cell movement/migration/invasion, e.g., small G-proteins, cytoskeletal proteins; and oncogenes. Specific targeting of CD4 with a drug may also be used for blocking HIV infection. Moreover, specific targeting of Ku70 may be used for killing or suppressing cancer cells and specific targeting of Cyclin-D1 may be used for blocking proliferation. Other exemplary drugs contemplated for blocking proliferation include chemotherapy agents set out below.

In addition, drugs for treating diseases such as viral diseases are also contemplated by the present invention. One example of such a drug is an siRNA which serves as a virocide. This is useful for treatment and/or prevention of HSV, HPB and HIV. Such therapeutic agents are described in PCT/US2006/021758 and PCT/US2003/034424, each of which are incorporated by reference in their entirety. Antiviral therapeutics also include viral entry inhibitors, viral assembly inhibitors, viral DNA and RNA polymerase inhibitors, viral reverse transcriptase inhibitors, viral protease inhibitors, viral integrase inhibitors, and inhibitors of viral shedding.

In some embodiments, the drug is a chemotherapy agent. Such agents include, e.g., anti-cancer drugs such as paclitaxel, methotrexate, doxorubicin, cisplatin, carboplatin; estrogen receptor (ER) antagonists such as, tamoxifen and its metabolites (e.g., 4-hydroxytamoxifen and endoxifen), and fulvestrant; and anti-angiogenesis agents such as canstatin, proliferin-related proteins, restin, maspin, osteopontin, Secreted Protein Acidic and Rich in Cysteine (SPARC) protein, Vascular Endothelial cell Growth Inhibitor (VEGI), prolactin, prothrombin, Interferon (IFN)-alpha, IFN-beta, IFN-gamma, C—X—C motif chemokine 10 (CXCL10), Interleukin (IL)-4, IL-12, etalloprotease and Thrombospondin domains protein (METH)-1 and METH-2, Tissue Inhibitors of etalloproteinase (TIMP), cell division autoantigen 1 (CDA1), platelet factor-4, vasostatin, calreticulin, endostatin, angiostatin, thrombospondin (TSP)-1 and TSP-2, Angiopoietin 2, Vascular Endothelial Growth Factor Receptor (VEGFR)-1, and Novel SH2-containing Protein 1 (NSP-1). Other chemotherapeutic agents include, but are not limited to, a Transforming Growth Factor Beta (TGFβ) inhibitor, a gamma-type Peroxisome Proliferator-Activated Receptor (PPARγ) ligand, an angiotensin activity inhibitor, a Platelet-Derived Growth Factor (PDGF) inhibitor, a sodium channel inhibitor, and an apoptosis inducer.

The amount of drug present in the micelle can vary over a wide range. The drug can be about 25% to about 75% (weight/weight) of the total mass of the micelle (wherein the mass of the drug is included in the total mass of the micelle). In some embodiments, the drug can be about 30% to about 60% w/w of the total mass of the micelle (same basis). In some embodiments, the drug can be about 40% to about 70% w/w of the total mass of the micelle (same basis).

In some embodiments, the micelles of the invention comprise one or more ligands conjugated to one or more PEG moieties. Ligands contemplated by the invention are discussed in more detail below. In some embodiments, the ligand is folic acid.

The term "ligand" refers to a compound that exhibits selectivity for a particular target organ, tissue or cell. A ligand is capable of binding to the particular target organ, tissue, or cell. As with the drug that may be loaded in a micelle, various ligands may be used in the micelles, compositions and methods herein. In some embodiments, the ligand binds a cancer cell. One example of a ligand is the vitamin folic acid (FA), which binds folate receptors that are overexpressed in ~90% of human ovarian carcinomas. Luteinizing hormone-releasing hormone (LHRH) is another suitable ligand. LHRH is relatively small molecule (MW 1,182 Da), with the receptors overexpressed by breast, ovarian, and prostate cancer cells. As another example, the ligand is a retinoid such as retinol, retinal, retinoic acid, rexinoid, or derivatives or analogs thereof. Further examples of ligands include, but are not limited to, transferrin, RGD peptide, Herceptin, prostate-specific membrane antigen (PSMA)-targeting aptamers, follicle stimulating hormone (FSH), epidermal growth factor (EGF) and the like. Other ligants include various antibodies such as anti-CD19, anti-CD20, anti-CD24, anti-CD33, anti-CD44, Lewis-Y antibody, sialyl Lewis X antibody, LFA-1 antibody, rituximab, bevacizumab, anti-VEGF mAb, and their fragments, dimers, and other modified forms. In other embodiments, the ligand targets an immune cell. For targeting immune cells, the ligand can be a ligand of e.g., a T cell surface receptor. Lectins can be used as ligands to target mucin and the mucosal cell layer. Lectins of use in the invention include those isolated from *Abrus precatroius, Agaricus bisporus, Glycine max, Lysopersicon esculentum, Mycoplasma gallisepticum*, and *Naja mocambique*, as well as lectins such as Concanavalin A and Succinyl-Concanavalin A.

In some embodiments, the ligand increases the selective delivery of the micelle to a particular target organ, tissue or cell. Target organs may include, for example, the liver, pancreas, kidney, lung, esophagus, larynx, bone marrow, and brain. In some embodiments, the increase in selective delivery may be at least about two-fold as compared to that of an otherwise comparable composition lacking the targeting agent. In some embodiments, the delivery of the micelle containing a ligand to the target organ, tissue or cell is increased by at least 10% compared to that of an otherwise comparable composition lacking the ligand. In some embodiments, the delivery of the micelle to the target organ, tissue or cell is increased by at least 25% or more as compared to that of an otherwise comparable composition lacking the ligand.

The amount of ligand present in a micelle can vary over a wide range. In some embodiments, the ligand can be about 1% to about 50% (weight/weight) of the total mass of the micelle (wherein the mass of the ligand is included in the total mass of the nanocore). In other embodiments, the ligand may be about 10% to about 30% w/w of the total mass of the micelle (same basis). In still other embodiments, the ligand may be about 20% to about 40% w/w of the total mass of the micelle (same basis).

In some embodiments, the ligands may be conjugated to the micelle through a covalent bond to PEG. A variety of mechanisms known to those skilled in the art can be used to form the covalent bond between the ligands and PEG, e.g., a condensation reaction. Additional methods for directly bonding one or more ligands to PEG are known to those skilled in the art, and may be identified by routine experimentation informed by the guidance provided herein. As is known to the skilled artisan, chemistries include, but are not limited to, thioether, thioester, malimide and thiol, amine-carboxyl, amine-amine, and others listed in organic chemistry manuals, such as, Elements of Organic Chemistry, Isaak and Henry Zimmerman Macmillan Publishing Co., Inc., New York, N.Y. Ligands can also be attached to PEG using a crosslinking reagent [e.g., glutaraldehyde (GAD), bifunctional oxirane (OXR), ethylene glycol diglycidyl ether (EGDE), N-hydroxysuccinimide (NHS), and a water soluble carbodiimide, such as 1-ethyl-3-(3-dimethylaminopropyl) carbodiimide (EDC)]. The compositions herein can further have at least one hydrolysable linker between the therapeutic agent and scaffold and/or targeting agent and scaffold.

Targeting efficacy of the micelles is enhanced by harnessing both mechanisms of passive and active targeting that complement each other.

In some embodiments, the outer surface of the micelle is modified. One example of such a modification is modification of the outer surface of the micelle with a long-circulating agent, e.g., glycosaminoglycans. Examples of suitable glycosaminoglycans for use include, e.g., hyaluronic acid. The micelles may also, or alternatively, be modified with a cryoprotectant, e.g., a sugar, such as trehalose, sucrose, mannose, glucose or HA. The term "cryoprotectant" refers to an agent that protects a lipid particle subjected to dehydration-rehydration, freeze-thawing, or lyophilization-rehydration from vesicle fusion and/or leakage of vesicle contents.

In some embodiments, micelles of the invention include one or more imaging agents. In this respect, the micelles can deliver single or dual imaging agents. Many imaging agents are known in the art (see, e.g., U.S. Pat. Nos. 5,021,236 and 4,472,509, both incorporated herein by reference). Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III). Radioisotopes of potential use as imaging or therapeutic agents include astatine$^{211}$, carbon$^{14}$, chromium$^{51}$, chlorine$^{36}$, cobalt$^{57}$, cobalt$^{58}$, copper$^{52}$, copper$^{64}$, copper$^{67}$, fluorine$^{18}$, gallium$^{67}$, gallium$^{68}$, hydrogen$^{3}$, iodine$^{123}$, iodine$^{124}$, iodine$^{125}$, iodine$^{131}$, indium$^{111}$, iron$^{52}$, iron$^{59}$, lutetium$^{177}$, phosphorus$^{32}$, phosphorus$^{33}$, rhenium$^{186}$, rhenium$^{188}$, and selenium$^{75}$ I$^{125}$ is used in some embodiments, and indium$^{111}$ is also used in some embodiments due to its low energy and suitability for long-range detection.

In some embodiments, the imaging agent is a secondary binding ligand or an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art and is described, for example, in U.S. Pat. Nos. 3,817,837; 3,850,752; 3,939,350; 3,996,345; 4,277,437; 4,275,149 and 4,366,241; each incorporated herein by reference in their entirety. These fluorescent labels are preferred for in vitro uses, but may also be of utility in in vivo applications, particularly endoscopic or intravascular detection and/or diagnostic procedures.

In some embodiments, the imaging agent is a fluorescent marker. Non-limiting examples of photodetectable labels include ALEXA 350, ALEXA 430, AMCA, aminoacridine, BODIPY 630/650, BODIPY 650/665, BODIPY-FL, BODIPY-R6G, BODIPY-TMR, BODIPY-TR, 5-carboxy-4$^{1}$, 5'-dichloro-2$^{1}$, 7$^{1}$-dimethoxy fluorescein, 5-carboxy-2',4',5', 7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FA, dansyl chloride, Fluorescein, HEX, 6-JOE, NBD (7-nitrobenz-2-oxa-1,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococyanin B, phycocyanin C, phycocyanin R, thiamine, phycoerythrocyanin, phycoerythrin R, REG, Rhodamine Green, rhodamine isothiocyanate, Rhodamine Red, ROX, TAMRA, TET, TRIT (tetramethyl rhodamine isothiol), Tetramethylrhodamine, Edans and TEXAS RED. These and other luminescent labels may be obtained from commercial sources such as Molecular Probes (Eugene, Oreg.), and EMD Biosciences (San Diego, Calif.).

Chemiluminescent agents of use may include luminol, isoluminol, an aromatic acridinium ester, an imidazole, an acridinium salt and an oxalate ester, or a bioluminescent compound such as luciferin, luciferase and aequorin. Diagnostic conjugates may be used, for example, in intraoperative, endoscopic, or intravascular tumor or disease diagnosis.

It is contemplated that, as with the other modifications disclosed herein, imaging agents can be attached to the amphiphilic dendron-coils and micelles by known methods and functional groups.

In a second aspect, the invention provides compositions of the micelles of the invention.

Compositions of micelles of the inventions for use in drug delivery comprise a pharmaceutically acceptable carrier (used interchangeably with the term pharmaceutically acceptable excipient). Such carriers include, but are not limited to, saline, buffered saline, dextrose, water, glycerol, ethanol, and combinations thereof. The formulation should suit the mode of administration and therefore, the formulation can be prepared with or without an agent or device for sustained release, for delivery locally or systemically. An "effective amount" as the term is used herein is an amount of a drug or combination of drugs sufficient to achieve a recognized medical endpoint, e.g., a decrease in tumor size or proliferation or a decrease in the symptoms of a viral infection. The effective amount can be determined empirically by a skilled artisan according to established methods of measurement of relevant parameters.

The compositions herein can further include wetting or emulsifying agents, or pH buffering agents. The composition can be a liquid solution, suspension, emulsion, tablet, pill, capsule, sustained release formulation, or powder. The compositions can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc.

In some embodiments, a composition herein is formulated in accordance with routine procedures as a pharmaceutical composition adapted for subcutaneous administration to human beings. Typically, compositions for subcutaneous administration are solutions in sterile isotonic aqueous buffer. Where necessary, the composition may also include a solubilizing agent and a local anesthetic to ameliorate pain at the site of the injection. Generally, the ingredients are provided either separately or mixed together in unit dosage form, for example, as a dry, lyophilized powder or water-free concentrate in a hermetically sealed container such as an ampoule or sachet, for example, indicating the quantity of active agent. Where the composition is to be administered by infusion, it can be dispensed with an infusion bottle containing sterile pharmaceutical grade water, buffer, or saline. Where the composition is administered by injection, an ampoule of sterile water or saline for injection can be provided so that the ingredients may be mixed prior to administration. The compositions herein can in various components thereof be formulated as suppositories, which contain active ingredient in the range of about 0.5% to about 10% by weight; oral formulations preferably contain about 10% to about 95% active ingredient by weight. A daily dose is administered as a single dose, or is divided into a plurality of smaller fractional doses, to be administered several times during the day.

In a third aspect, the invention provides methods of delivering a drug to a patient comprising administering a composition comprising a micelle of the invention and a pharmaceutically acceptable carrier.

As used herein, a dosing schedule refers to a protocol for administering any of the compositions as described herein, in an effective dose, administered simultaneously or within a particular interval of each other, for example, within one day of each other, or as a combined preparation, or separately, and includes the amount of the composition delivered per unit time such as per day, and the duration or period of time over which each composition is administered.

Aggressive tumors inherently develop leaky vasculature with 100 to 800 nm pores due to rapid formation of vessels that must serve the fast-growing tumor. This defect in vasculature coupled with poor lymphatic drainage serves to enhance the permeation and retention of drug delivery particles within the tumor region. This is often called the EPR effect. This phenomenon provides for "passive targeting." The basis for increased tumor specificity is the differential accumulation of drug-loaded particles in tumor tissue versus normal cells, which results from particle size rather than binding. Normal tissues contain capillaries with tight junctions that are less permeable to nanosized particles. Passive targeting can therefore result in increases in drug concentrations in solid tumors of several-fold relative to those obtained with free drugs.

Passive delivery may also be directed to lymphoid organs of the mammalian immune system, such as lymphatic vessels and spleen. These organs are finely structured and specialized in eliminating invaders that have gained entry to tissue fluids. Nanosized particles may easily penetrate into lymphatic vessels taking advantage of the thin walls and fenestrated architecture of lymphatic microvessels. Passive targeting to the spleen is via a process of filtration. Indeed the spleen filters the blood of foreign particles larger than 200 nm. This function facilitates splenic targeting with nanosized particles encapsulating drug for effective treatments against several hematological diseases.

Given that the micelles of the invention have a controlled size range, which takes advantage of passive targeting, and also provides active targeting to reduce side effects and cytotoxicity of the polymeric scaffold, the present invention also provides methods for preventing or treating a disease or condition such as cancer (e.g., gastric, lung, breast, ovarian, liver, bronchogenic, nasopharyngeal, laryngeal, pancreatic, bladder, colon, and cervical cancers), viral infection or other diseases that induce leaky vasculature, e.g., inflammatory diseases, macular degeneration and diabetes. The method involves the step of administering to a subject in need thereof a composition as described herein in an amount sufficient to decrease one or more signs or symptoms of the disease or condition. Such symptoms can include, but are not limited to a decrease in cancer cell proliferation, a decrease in tumor size, a decrease in the number of infective viral units in the subject, or a decrease in vascular leakage as determined by routine methods. Administering the composition described herein reduces signs or symptoms of the disease or condition in a subject, compared to the signs or symptoms in subject prior to administering the composition, or compared to a subject not receiving such treatment.

Given the instant design, the non-specific interaction of the micelle composition during circulation will be avoided until the biodegradable micelles accumulate (due to the EPR effect) at the tumor sites or sites of vascular leakage.

The amount of the micelle of the invention which will be effective in the treatment of a particular disease or condition will depend on the nature of the disease or condition, and can be determined by standard clinical techniques. The precise dose to be employed in the formulation will also depend on the route of administration, and the seriousness of the disease or condition, and should be decided according to the judgment of the practitioner and each patient's circumstances. Effective doses may be extrapolated from dose-response curves derived from in vitro or animals or animal model test systems, by one of ordinary skill in the art of pharmacology. Dosages of the compositions to be administered to a subject are adjusted for known variations from species to species using standard data encompassing criteria for absorption, distribution, half-life kinetics in circulation, metabolism, excretion, and toxicology of the compositions of the embodiments herein. Suitable dosage ranges for administration are generally about 0.01 micrograms to about 10,000 micrograms of each active compound per kilogram body weight per day, for example, about 0.01 micrograms to about 1 microgram/kg, about 0.1 micrograms/kg to about 10 micrograms/kg, about 1 microgram/kg to about 500 micrograms/kg, or about 10 micrograms/kg to about 10 mg/kg of body weight per day. Suitable dosage ranges for administration are thus generally about 0.01 micrograms/kg body weight/day to about 10 mg/kg body weight/day.

The invention provides a pharmaceutical pack or kit comprising one or more containers filled with one or more of the ingredients of the compositions of the invention. In such a pack, or kit, can be found a container holding a micelle composition of the invention. Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

In a fourth aspect, the invention provides methods of capturing a cell from a sample by: exposing the sample to an immobilized amphiphilic dendron-coil of the invention which comprises a non-peptidyl, hydrophobic core-forming block, a polyester dendron and a poly(ethylene) glycol (PEG) moiety with a ligand conjugated to the PEG, wherein the ligand binds to the cell; and capturing the cell by binding of the ligand to the cell. Ligands contemplated by the invention are discussed above. In some embodiments, the ligand is folic acid. In some embodiments, the cell is a circulating tumor cell (CTC).

The invention also provides a devices for capturing cells from a sample. The devices comprise immobilized amphiphilic dendron-coils of the invention which comprise a non-peptidyl, hydrophobic core-forming block, a polyester dendron and a poly(ethylene) glycol (PEG) moiety with a ligand conjugated to the PEG, wherein the ligand binds to the cells; and the devices capture the cells by binding of the ligand to the cell. Again, ligands contemplated by the invention are discussed above. In some embodiments, the ligand is folic acid. In some embodiments, the cell is a circulating tumor cell (CTC).

In some embodiments, the device includes a channel that includes a cell capture surface and a flow modification surface. The cell capture surface includes an amphiphilic dendron-coil of the invention with a ligand conjugated thereto. The flow modification surface includes one or more structures arranged to induce a rotational flow in the a sample flowing through the channel. Using the device in a method for capturing cells (including, but not limited to, CTCs) from a sample, the method includes includes introducing the sample into the device under conditions that allow a cell to bind to the ligand. The flow modification surface induces a rotational flow in the sample allowing enhanced contact of the cells with the cell capture surface and, thus more efficient cell capture. Use of amphiphilic dendron-coils of the invention as capturing agents in the devices and methods described in WO 2010/124227 (published Oct. 28, 2010 and incorporated by reference herein in its entirety) are specifically contemplated.

EXAMPLES

Various aspects and advantages of the invention are illustrated in the non-limiting examples below, wherein Example 1 describes exemplary uses of materials and methods of the invention, Example 2 describes the preparation of exemplary amphiphilic dendron-coils (DCs) and encapsulation of the drug indomethacin in exemplary micelles of the invention, Example 3 describes the encapsulation of the drug α-mangostin in exemplary micelles of the invention, Example 4 describes exemplary folic acid-conjugated micelles of the invention and Example 5 describes supramolecular structures of exemplary micelles of the invention.

Example 1

In response to the need for development of effective cancer treatments, the present invention provides two approaches: 1) cancer cell specific targeting using nanocarriers for enhanced therapeutic indices with reduced toxicity concerns and 2) selective detection and isolation of circulating tumor cells (CTCs) for diagnosis and prognosis of cancer metastasis. Both necessitate a strong, selective binding to biological targets (cell surface markers for targeting or whole cells for capturing), which may be achieved by utilizing multivalent binding. Multivalent binding properties can be engineered and fabricated using nanotechnology that allows a single versatile material to be used for multiple biomedical purposes. The present invention contemplates a nano-scale material that is useful for targeting (when formulated as a drug delivery nanocarrier) as well as capturing (when surface immobilized) cancer cells.

Multivalent binding is the simultaneous binding event of multiple ligands to multiple receptors in biological systems, which is central to a number of pathological processes, including the attachment of viral, parasitic, mycoplasmal, and bacterial pathogens. These activities can promote targeting of specific cell types. Studies with biological multivalent inhibitors have yielded quantitative measurements of binding avidities, with increases on the order of 1 to 9 orders of magnitude[15-17]. Polyamidoamine (PAMAIA) dendrimers have been reported to be an excellent mediator for facilitated multivalent effect because pre-organization/orientation of ligand, polymer backbone topology, and easy deformability of the material all contribute for strong multivalent binding to cell surfaces[14]. However, PAMAM dendrimers have several drawbacks such as: 1) limited drug payloads—therapeutics can be stably carried only if chemically conjugated, and thus the number of drugs per molecule is limited by the number of the available surface functional groups and steric hindrance and 2) toxicity concerns due to non-biodegradability and intramolecular charges by tertiary amines.

The present invention instead utilizes a dendron as a platform material. A dendron is monodisperse wedge-shaped dendrimer section with multiple terminal groups and a single reactive function at the focal point. In some embodiments, the invention contemplates the use of polyester-16-hydroxyl-1-alkyne dendron as it has outstanding potential to facilitate the multivalent binding as well as to be utilized for multiple biological applications[18]. This dendron shares the advantages of a dendrimer such as: 1) chemically well-defined structure; 2) precise control over size and number of terminal functional groups; and 3) easy control over possible chemistries such as introduction of pH-, thermo-, or enzyme-sensitive linkages to control the drug release kinetics. In addition to those advantages, this dendron uniquely provides an option of orthogonal reactions utilizing the distinct focal point and surface groups. The peripheral groups of the dendron (see FIG. 1 for chemical structure) provide multiple, well-defined reactive sites for conjugation with targeting molecules. Flexibility (conformability) of the dendron branches that are pre-organized in a relatively small area facilitates localized multivalent effect, which is expected to substantially enhance targeting/capturing efficiency of the functionalized dendron. Furthermore, amphiphilicity of dendron will be engineered by introducing a hydrophobic or hydrophilic building block to the focal point (alkyne) of dendron (see FIG. 2) through click chemistry. The enhanced targeting efficacy through engineered multivalent effect, along with the easy control over supramolecular structure, makes the dendron-based nanomaterial a novel, versatile platform.

Thus, the invention involves multiple aspects, including but not limited to, the following.

1) Preparation of Multivalent Dendron Conjugates and Optimization of Multivalent Effect.

A synthetic route for multivalent dendron conjugates is outlined in FIG. 1 (Panel SA1). Briefly, dendron (generation 4, Polyester-16-hydroxyl-1-acetylene bis-MPA dendron, Sigma-Aldrich) is modified through reaction with PEG diamine ($NH_2$-PEG-$NH_2$) to decorate the peripheral surface with primary amine groups, resulting in amine-terminated dendron (dendron-PEG-NH$_2$). A series of targeted dendron conjugates is prepared by conjugation with various amounts of a targeting molecule. In some embodiments, the targeting molecule is folic acid (FA). After conjugation of FA using 1-ethyl-3-(3-dimethylaminopropyl)carbodiimide (EDC) chemistry, the remaining amine groups are acetylated to prevent any electrostatic, non-specific interactions[14,19-21]. FA has great potential for cancer targeting because folate receptors (FR) are overexpressed in many human carcinomas[22]. Furthermore, as a low molecular weight (MW 441) ligand, FA presumably lacks immunogenicity; still has high affinity for FR (K$_D$~10$^{-10}$ M), and defined conjugation chemistry[23]. To determine an optimal range of number of targeting molecules conjugated to the targeted dendron conjugates (dendron-PEG-FA), a series of experiments are conducted. First, extensive material characterization using NMR, FT-IR, UV/Vis, dynamic light scattering (DLS), HPL, GPC, and capillary electrophoresis (CE) are performed. Second, the surface plasmon resonance (SPR) technique using Biacore X quantifies material design-dependent binding events of dendron-PEG-FA at a .molecular level, using a similar method to that previously described[14]. Optimized targeted dendron conjugates self-assemble into dendron-based nanomicelles (DNM) after further modification with a hydrophobic block (FIG. 1, Panel SA2) or immobilization on surfaces to capture target cells (FIG. 1, Panel SA3).

2) Preparation of Amphiphilic Dendrons for Micelle Formulation and In Vitro Validation of Targeting Efficacy.

Figure 2:
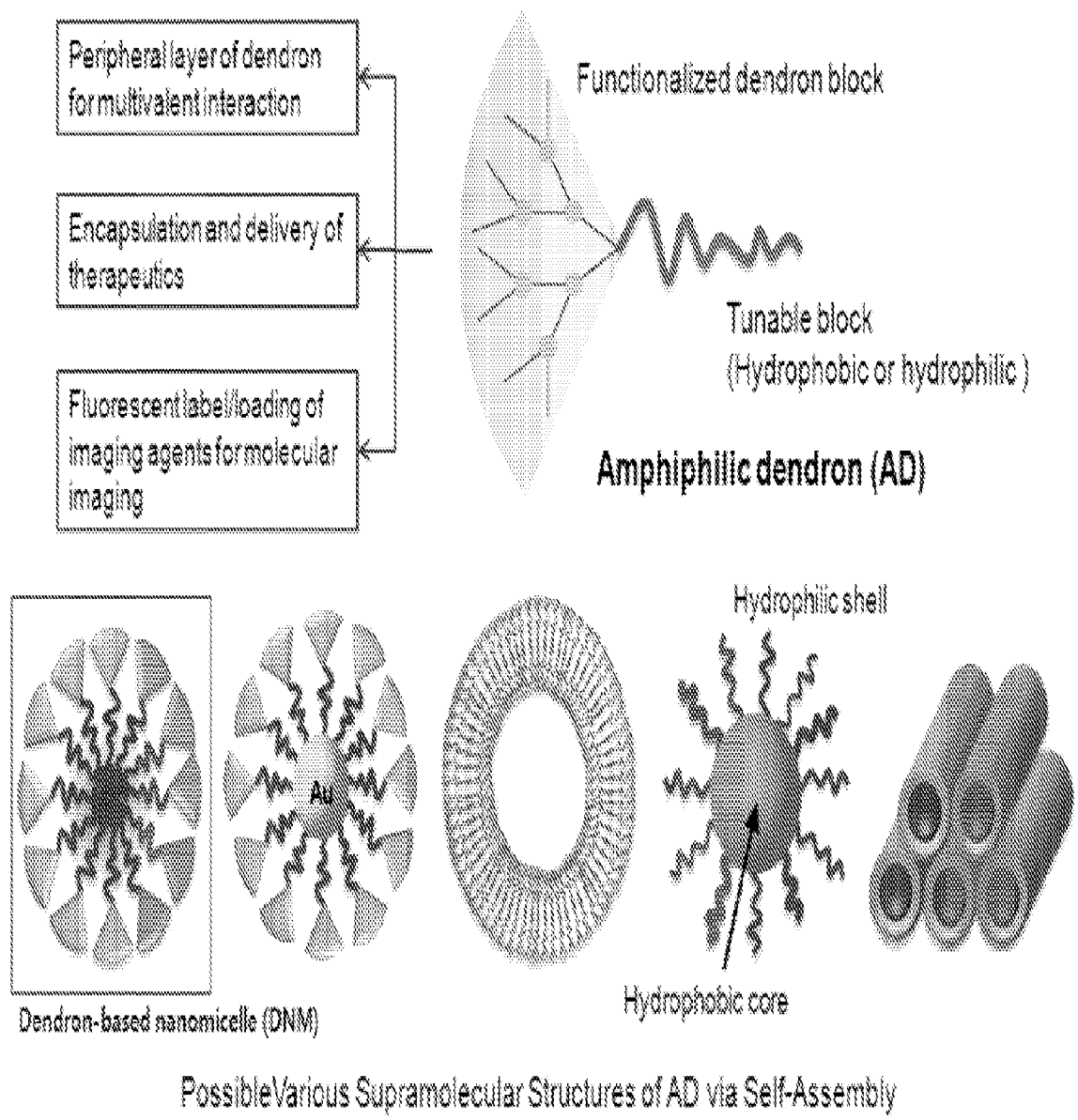
FIG. 2 shows various possible supramolecular structures of amphiphilic dendron-coils.

As illustrated in FIG. 2, the hydrophilic/hydrophobic balance between the core and dendron blocks determines supramolecular structure (e.g., sphere, vesicle, disk, or cylinder) that is formed via self-assembly of the amphiphilic molecules in a given solvent system[24]. The nano-scale structure derived from self-assembly is primarily .affected by several parameters: 1) generation of the dendron; 2) size of the core; 3) relative hydrophilicity of the attached block; and 4) type of solvent used. By controlling these parameters, the morphology and size of dendron-hased nanocarriers can be manipulated. In some embodiments, DNM with a hydrophobic core [by conjugation of a lipophilic polymer block such as poly (lactic acid)] and a hydrophilic PEG outer-layer with size of 20-30 nm in diameter is anticipated to utilize both passive and active targeting for drug delivery. Fluorescence activated cell sorter (FACS), cofocal laser scanning microscopy (CLSM), and fluorescence resonance energy transfer (FRET) analyses are used to confirm the consistency of the quantitative SPR data with the in vitro results using K13 cells which FR expression can be easily regulated[14,25]. Additional FR expressing cells such as A2780, and SKOV3 cells can also be employed to test specificity of DNM.

3) Surface Immobilization of the Multivalent Conjugates and In Vitro Validation of Capturing Efficiency Using Mixture of Two or More Cell Lines.

Significant efforts have been made to selectively capture CFCs from the blood stream. Although recent results using anti-EpCAM have been reported[26], sensitivity/specificity still needs to be improved to achieve highly sensitive capturing devices for rare cells. To this end, the strong, localized multivalent binding mediated, for example, by dendron-PEG-FA (prepared in SAI) will increase sensitivity of the surface to recognize target cells (FIG. 1, Panel SA3).

To further increase selectivity, surfaces are first coated with non-fouling polymers such as PEG-based self-assembled monolayers (SAMs)[27]. The reactive sites (azide group for click chemistiy) for subsequent conjugation with dendron-PEG-FA are controlled by varying ratios and lengths between mono- (for non-fouling) and azide-terminated bi-functional (for conjugation) PEG SAMs. Binding kinetics between the surface and cell-mimicking microspheres (polystyrene beads coated with FR) will be first measured using Biacore X to determine optimal surface presentation of dendron-PEG-FA. Subsequently, in vitro validation is performed using a mixture of two cell lines: KB cells as a CTC model and HL-60 cells as a leukocyte model.

Thus, the invention provides multivalent dendron conjugates with versatility for 1) targeted drug delivery after formulated into DNM and 2) cell specific capturing when immobilized on surfaces.

The targeted drug delivery platform exhibits enhanced targeting efficacy utilizing passive and active targeting, and enhanced drug loading capacity. The multivalent dendron-mediated binding plays a key role in enhancing the targeting efficacy of DNM. Additionally, the PEG outer-layer prolongs the blood circulation time of the DNM and minimizes systemic clearance (24), resulting in selective accumulation of DNM with precisely controlled size in tumor sites through the enhanced permeation and retention (EPR) effect.

In cell capturing products, the multivalent effect of the dendron conjugates immobilized on non-fouling, biocompatible surfaces provides enhanced sensitivity and selectivity of the surfaces towards target cells. Unlike currently available capturing devices, the system is transformable platform technology since a variety of targeting agents specific to different cancer cell types can be employed through surface modification of the conjugates and be easily immobilized through one-step click chemistry.

Example 2

Figure 3:
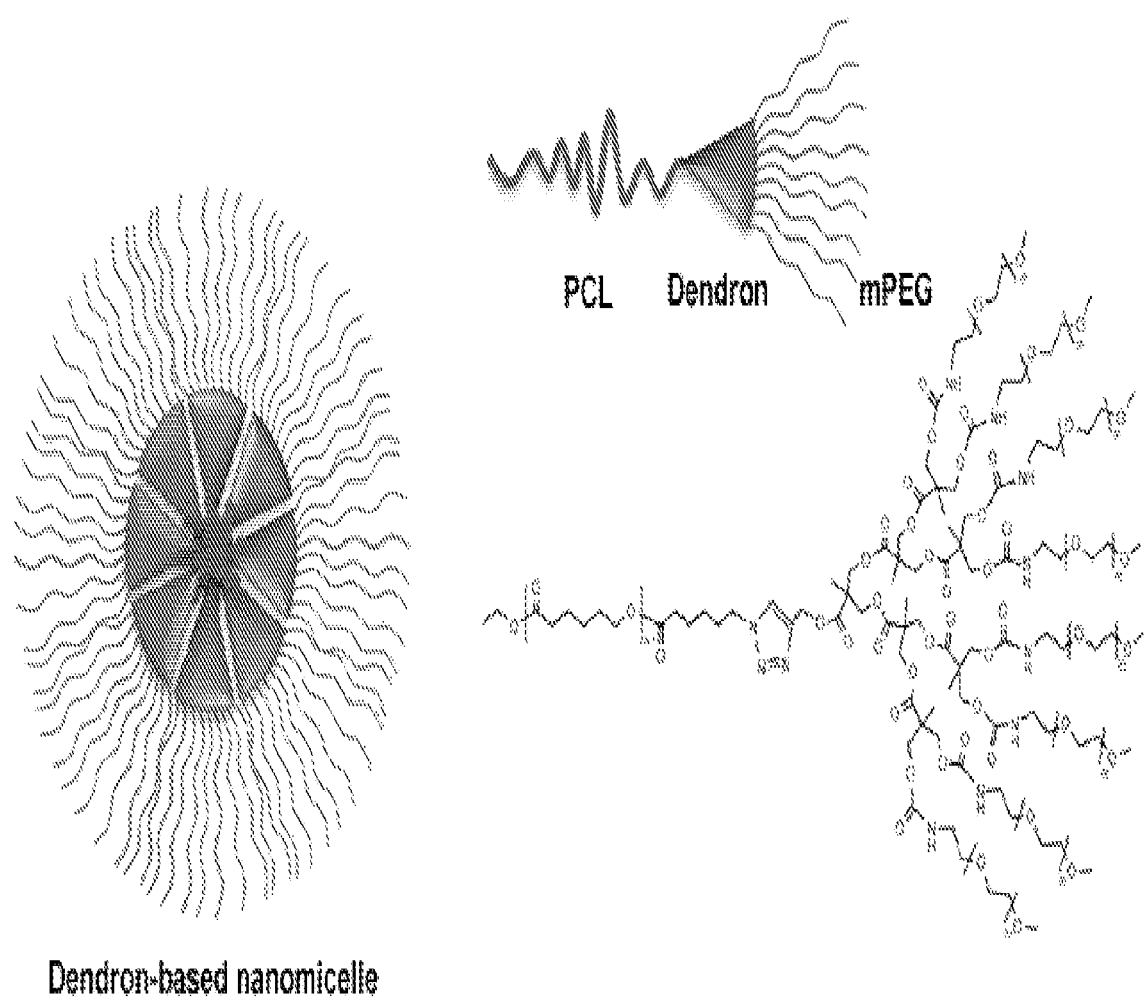
FIG. 3 shows the chemical structure of amphiphilic dendron-coils prepared through click chemistry between poly (caprolactone) (PCL), dendron and methoxy poly(ethylene glycol) (mPEG) and its self-assembled structure.

Four novel amphiphilic DCs with the general structure shown in FIG. 3, along with analogous linear-block copolymers were prepared. The amphiphilic DCs were designed with three major functional components: (1) poly(caprolactone) (PCL) as the hydrophobic core-forming block; (2) polyester G3-dendron with acetylene core to enable facile attachment of PCL by click chemistry, introduce additional molecular flexibility, to achieve a localized high density of peripheral functional groups and to mediate the combination of core- and shell-forming blocks; and (3) methoxy poly (ethylene glycol) (mPEG) to form the hydrophilic corona. In addition, two different molecular weights of PCL (PCL3.5K and PCLI4K) and mPEG (mPEG2K and mPEG5K) were used to vary HLB values of the resulting amphiphilic DCs.

Figure 4:
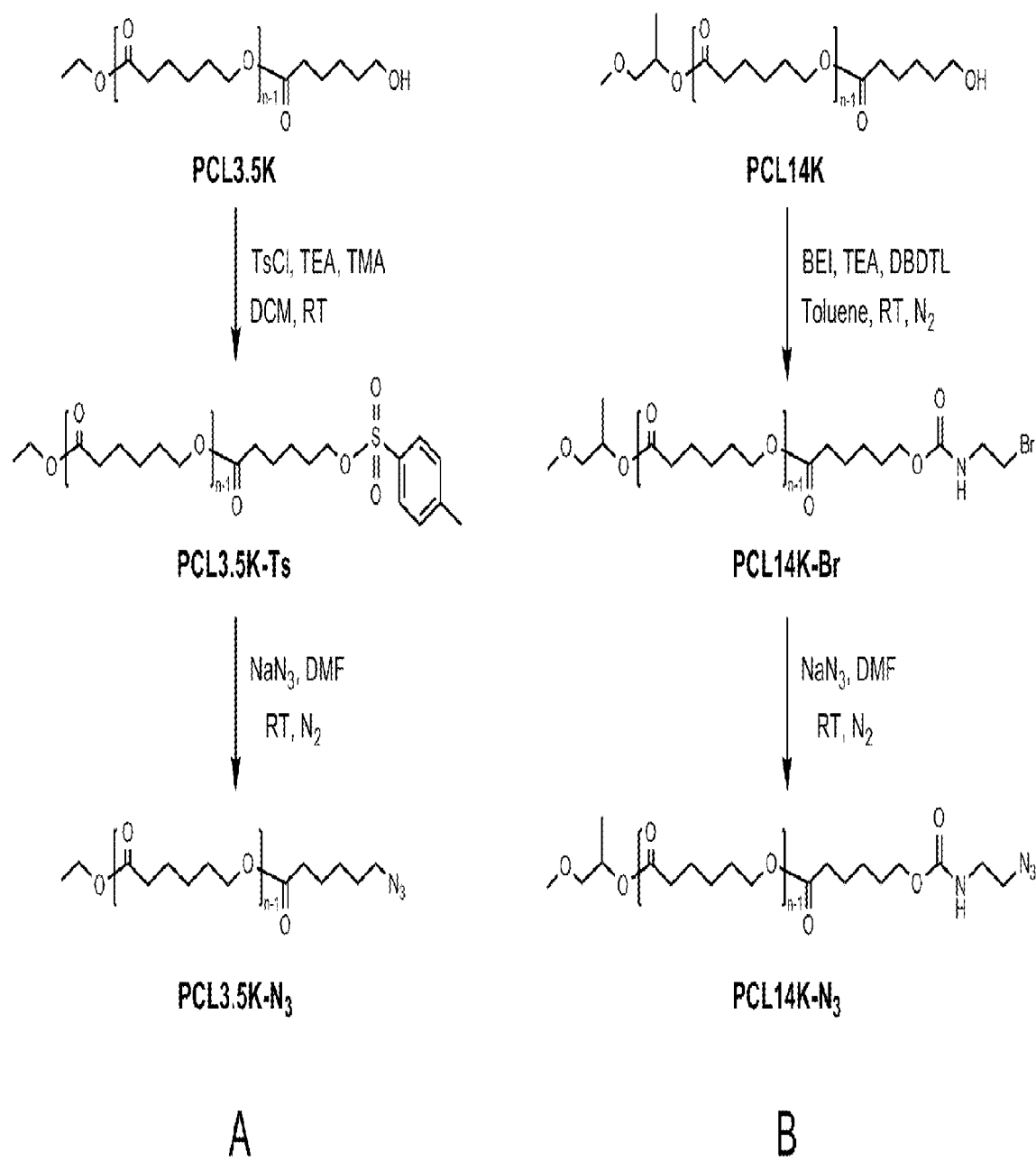
FIG. 4 shows the azido-functionalization of PCL3.5K (Panel A) and PCL14K (Panel B).
Figure 5:
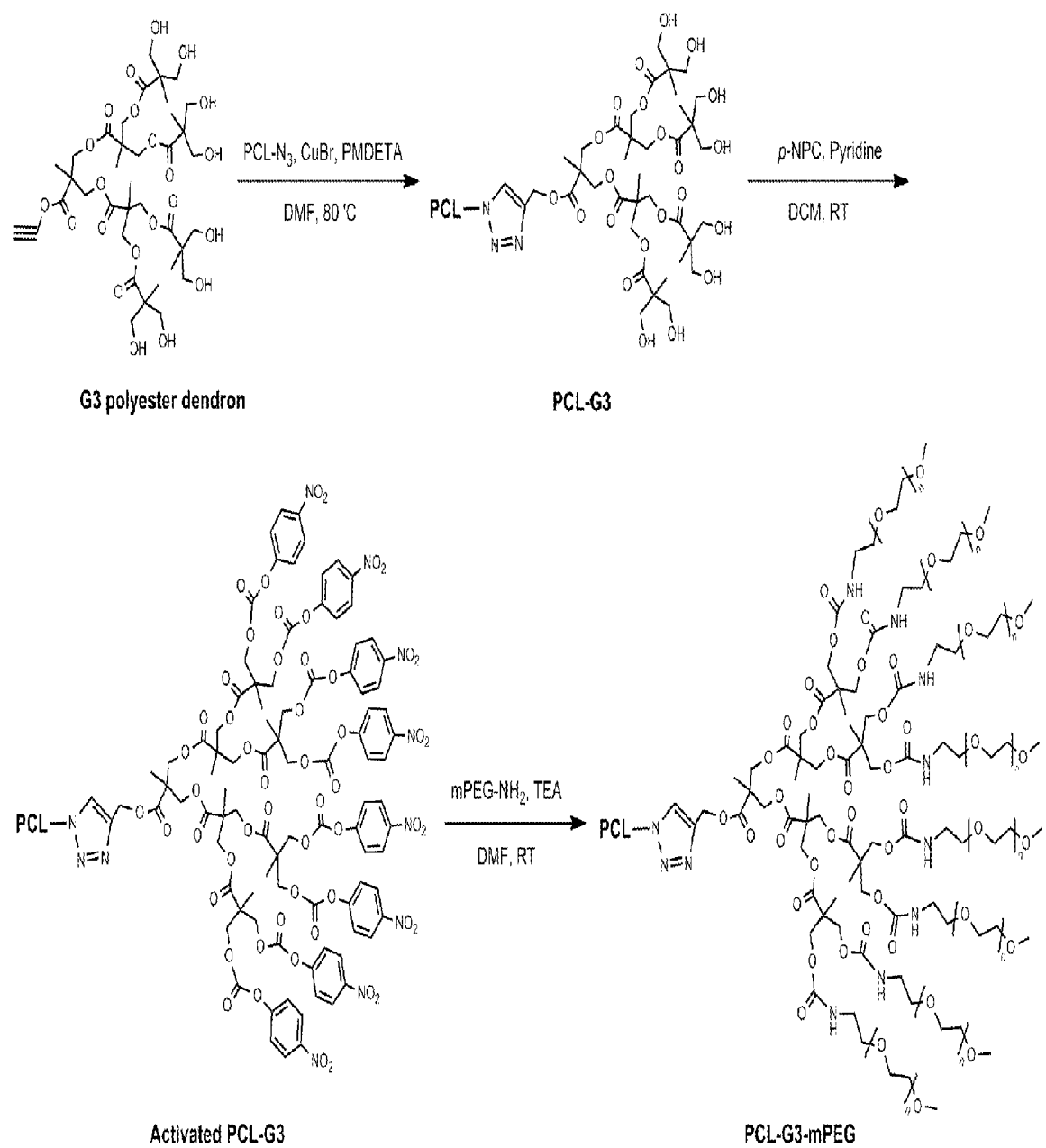
FIG. 5 shows the synthesis of PCL-G3 via click chemistry and mPEG conjugation to PCL-G3.
Figure 6A:
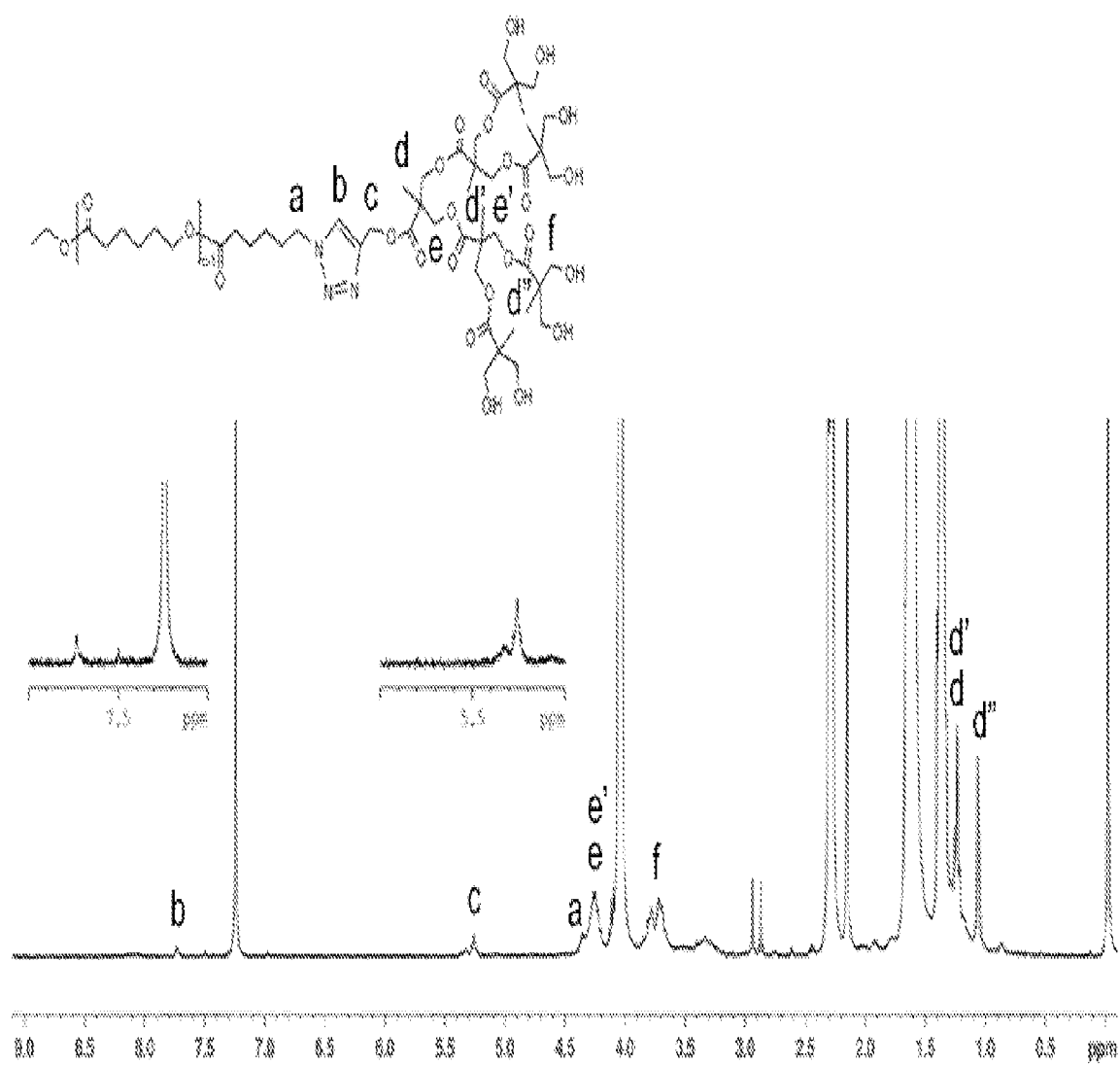
FIG. 6 shows $^1$H-NMR spectra of PCL3.5K-G3 (Panel A) and PCL14K-G3 (Panel B) prepared by click reaction. In the $^1$H-NMR spectrum of PCL3.5K-G3, the characteristic peaks of the polyester dendron were observed at 4.40-4.18, 3.82-3.60, and 1.06. The three peaks corresponding to the triazole formation appeared at 7.73, 5.26 and the third overlapped with the G3 dendron.[3b,13] In the case of PCL14K-G3, the peaks corresponding to the triazole ring appeared at 7.80, 5.27, and 4.49.
Figure 6B:
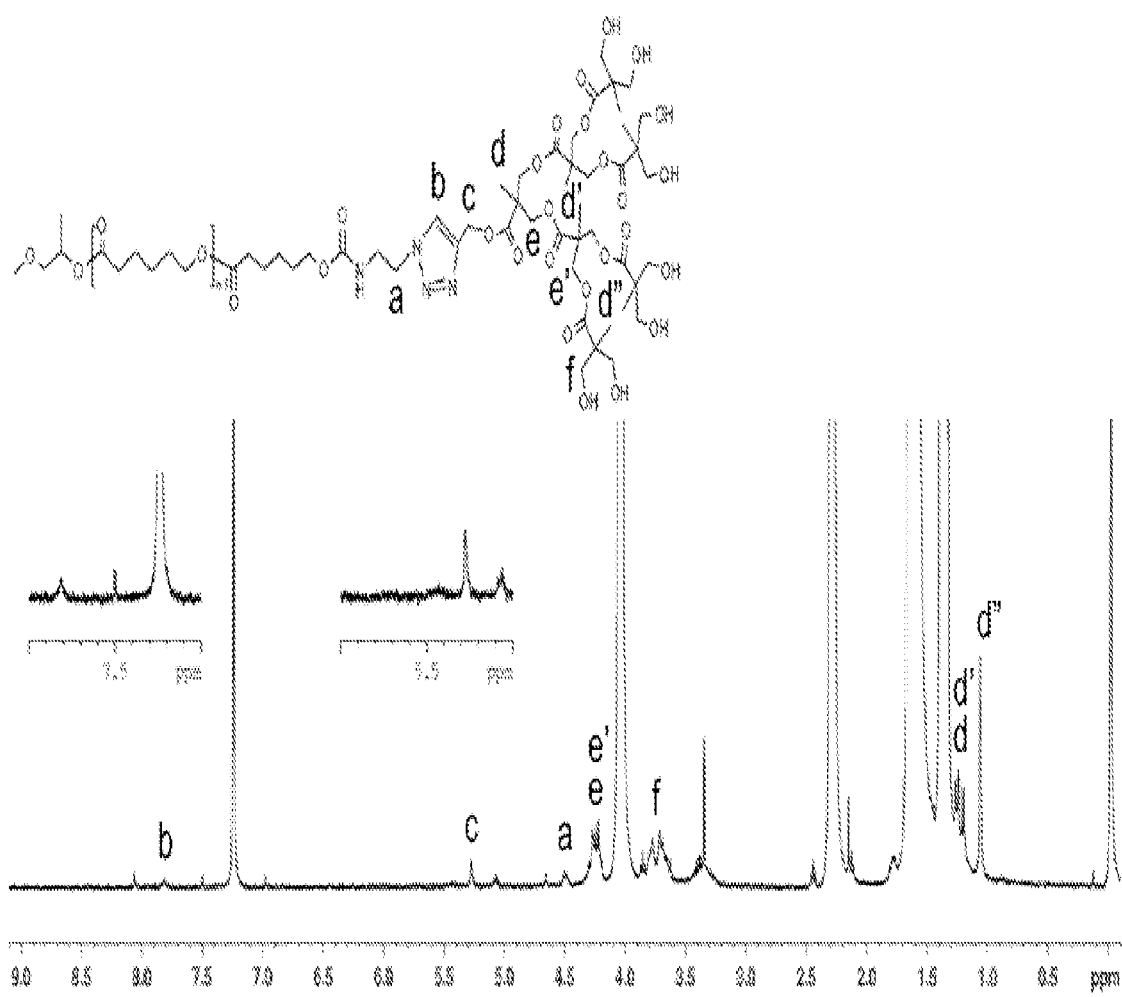
Figure 7:
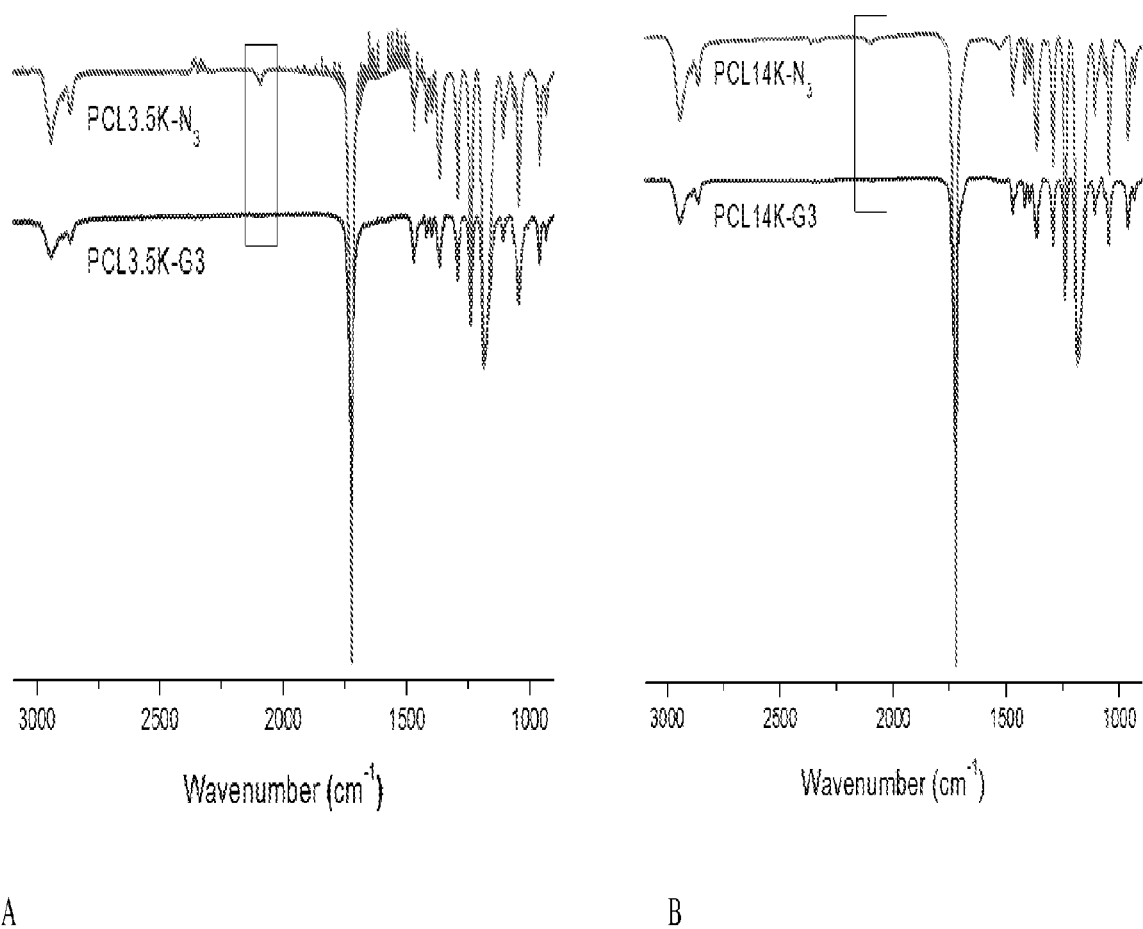
FIG. 7 shows FT-IR spectra of PCL3.5K-$N_3$ and PCL3.5K-G3 (Panel A), PCL14K-$N_3$ and PCL14K-G3 (Panel B). The disappearance of the azide peak at 2095 $cm^{-1}$ in the FT-IR spectra supports that the click reaction was successful.
Figure 8:
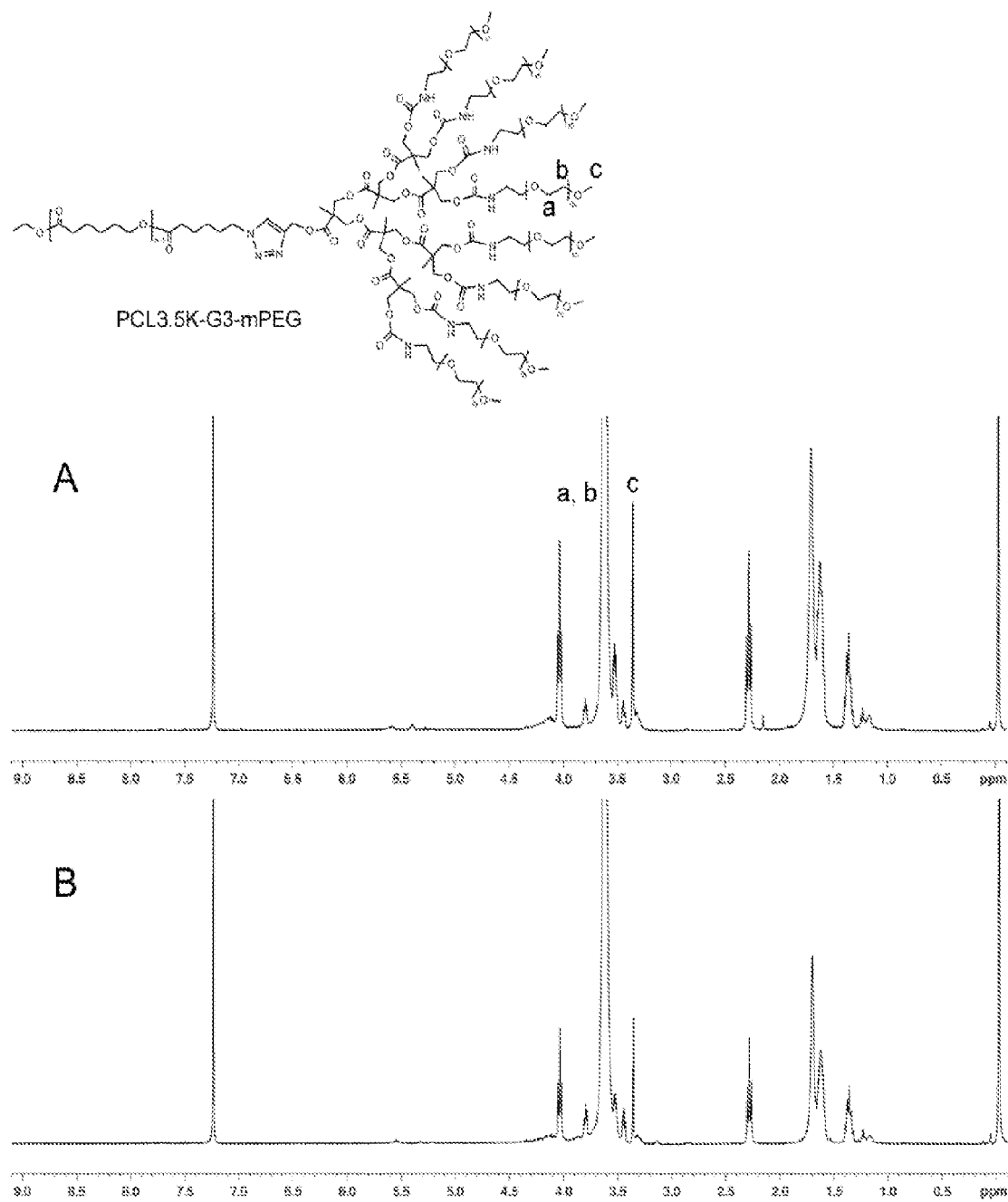
FIG. 8 shows $^1$H-NMR spectra of PCL3.5K-G3-mPEG2K (A) and PCL3.5K-G3-mPEG5K (B). The major peak representing the ethylene glycol repeating unit for mPEG appeared at 3.62 along with the singlet corresponding to methoxy groups at 3.36. Setting the peak integration values of PCL as a control, the conjugated mPEG integration value was close to the theoretical number of protons needed to indicate multiple mPEG molecules were successfully introduced to the periphery of the PCL3.5K-G3. In addition, the conjugation of mPEG5K-$NH_2$ was attributed to higher intensity corresponding to the number of attached mPEG molecules, compared to linear PCL-mPEG.
Figure 9:
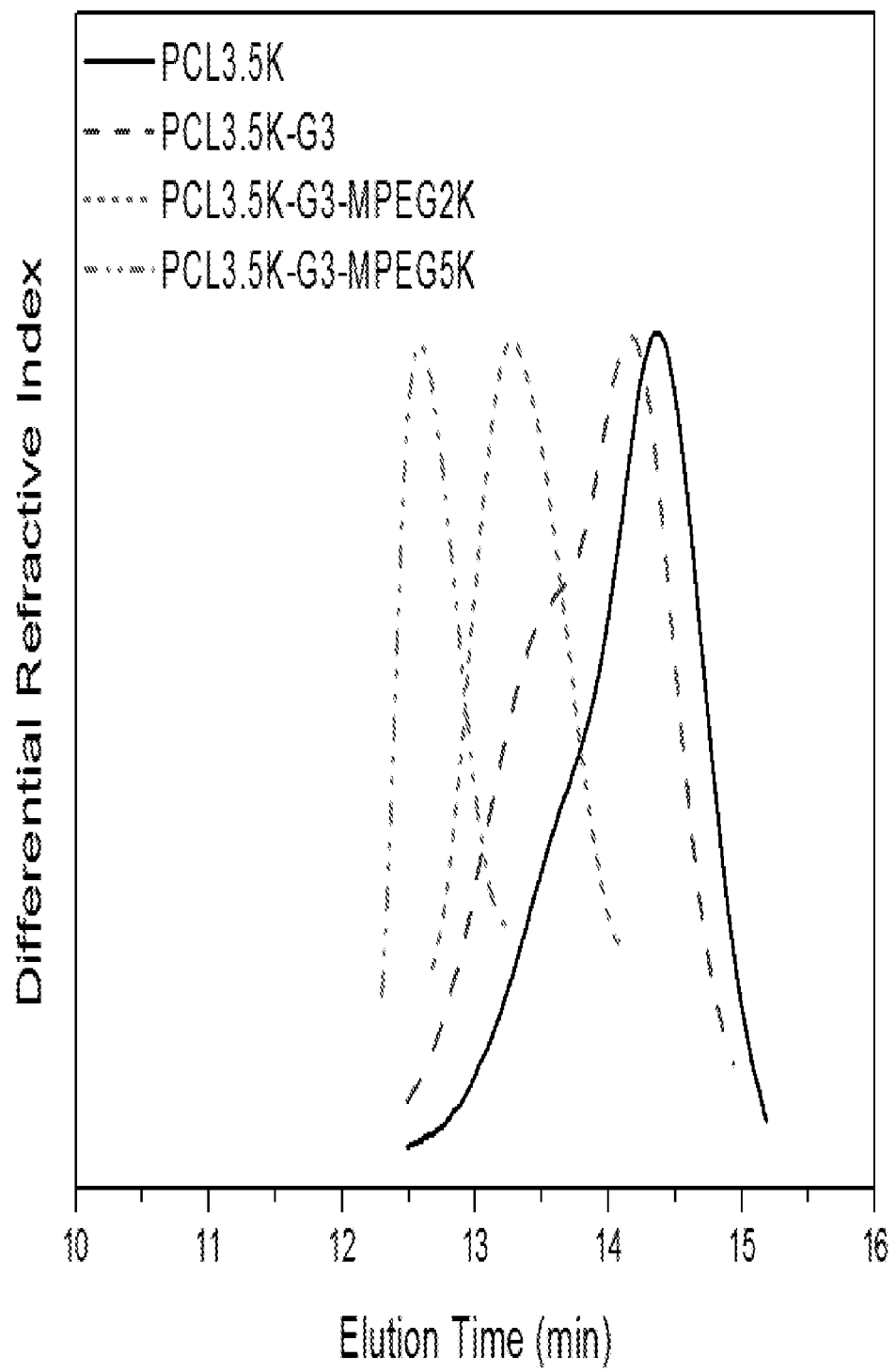
FIG. 9 shows GPC traces of PCL3.5K, PCL3.5K-G3, PCL3.5K-G3-mPEG2K, and PCL3.5K-G3-mPEG5K. The GPC traces represent the great shift to shorter elution time as the molecular weights of the samples increase.

The PEGylated DCs were synthesized via a multiple-step process. The terminal hydroxyl group of PCL3.5K and PCLI4K were first converted to an azide group (PCL-N$_3$) for subsequent conjugation with a dendron via click chemistry (FIG. 4, Panels A and B).[28] Complete conversion of the hydroxyl groups of PCL to azide was confirmed by IH-NMR (Figure S3). G3-dendron bearing an acetylene group at the focal point was then reacted with PCL-N 3 via click chemistry to yield 2 types of PCL-G3 (FIGS. 5; 6, Panels! and B; and 7, Panels A and B).[29] To achieve high reaction yields, various click reaction conditions were tested and an optimized condition was found (See details in Supporting Information).[30] Both types of mPEG were then conjugated to PCL-G3 following activation of surface hydroxyl groups with p-nitrophenyl chloroformate.[31] Changes in the structures and the molecular weights of the resulting copolymers were monitored by I H-NMR and GPC at each reaction step (FIGS. 8, Panels A and B; 9, Panels A and B; and Table 1).

TABLE 1

Molecular weight and polydispersity index (PDI) of polymers used in this study. The molecular weights of PCL-G3-mPEG increased significantly due to multiple conjugations of mPEG molecules to the periphery of the G3 dendron and all copolymers showed relatively narrow polydispersity around 1.07-1.38.

| Samples | Theoretical Mw | $M_n$[a] | $M_n$[b] | PDI[c] |
|---|---|---|---|---|
| PCL3.5K | 3,500 | — | 3,500 | 1.03 |
| PCL3.5K-G3 | 4,370 | 4,020 | 3,630 | 1.27 |
| PCL3.5K-G3-mPEG2K | 21,990 | 26,280 | 24,290 | 1.07 |
| PCL3.5K-G3-mPEG5K | 44,720 | 48,090 | 38,900 | 1.06 |
| PCL14K | 14,000 | — | 13,370 | 1.20 |
| PCL14K-G3 | 14,870 | 14,780 | 16,370 | 1.27 |
| PCL14K-G3-mPEG2K | 32,490 | 32,000 | 27,710 | 1.16 |
| PCL14K-G3-mPEG5K | 55,220 | 58,780 | 54,140 | 1.38 |

[a]Number-averaged molecular weight, $M_n$, estimated by $^1$H-NMR.
[b],[c]Measured by GPC using triple angle laser light scattering.

Interestingly, those micelles were primarily composed of hydrophilic blocks described by hydrophilic-lipophilic balances[32] (HLB) greater than 10. Yet when the thermodynamic stability was assessed by evaluation of the CMC, the values were in the $10^{-8}$ M range which is orders of magnitude lower than linear-block copolymers with the same HLBs.[33] Here, we explore this contradiction by systematic comparison of the self-assembly properties of amphiphilic DCs and linear-block copolymers.

We directly measured the thermodynamic stability of each amphiphilic copolymer by measuring the CMC.[34] Table 2 summarizes the CMC results along with HLB and LH-ratio of amphiphilic DCs and linear-block copolymers.

TABLE 2

Critical micelle concentrations (CMCs) of the amphiphilic copolymers with various hydrophilic-lipophilic balances (HLBs).

| Sample | HLB[a] | HL-ratio[b] | CMC (mg/L) | CMC ($10^{-7}$ M) |
|---|---|---|---|---|
| PCL3.5K-mPEG2K | 7.27 | 36:64 | 1.32 | 2.40 |
| PCL3.5K-mPEG5K | 11.76 | 59:41 | 3.29 | 3.75 |
| PCL14K-mPEG2K[c] | 2.50 | 13:87 | — | — |
| PCL14K-mPEG5K | 5.26 | 26:74 | 1.62 | 0.82 |
| PCL3.5K-G3-mPEG2K | 16.56 | 77:23 | 4.87 | 3.02 |
| PCL3.5K-G3-mPEG5K | 18.42 | 91:9 | 12.59 | 3.52 |
| PCL14K-G3-mPEG2K | 10.93 | 52:48 | 1.62 | 0.65 |
| PCL14K-G3-mPEG5K | 14.90 | 74:26 | 4.74 | 1.17 |

[a]HLB = $20 M_H/(M_H+M_L)$, where $M_H$ is the mass of the hydrophilic block and $M_L$ is the mass of the lipophilic block. The polyester dendron is considered to be part of the hydrophilic block.
[b]Hydrophilic-lipophilic ratio.
[c]PCL14K-mPEG2K could not be tested due to its poor water solubility.

Figure 10:
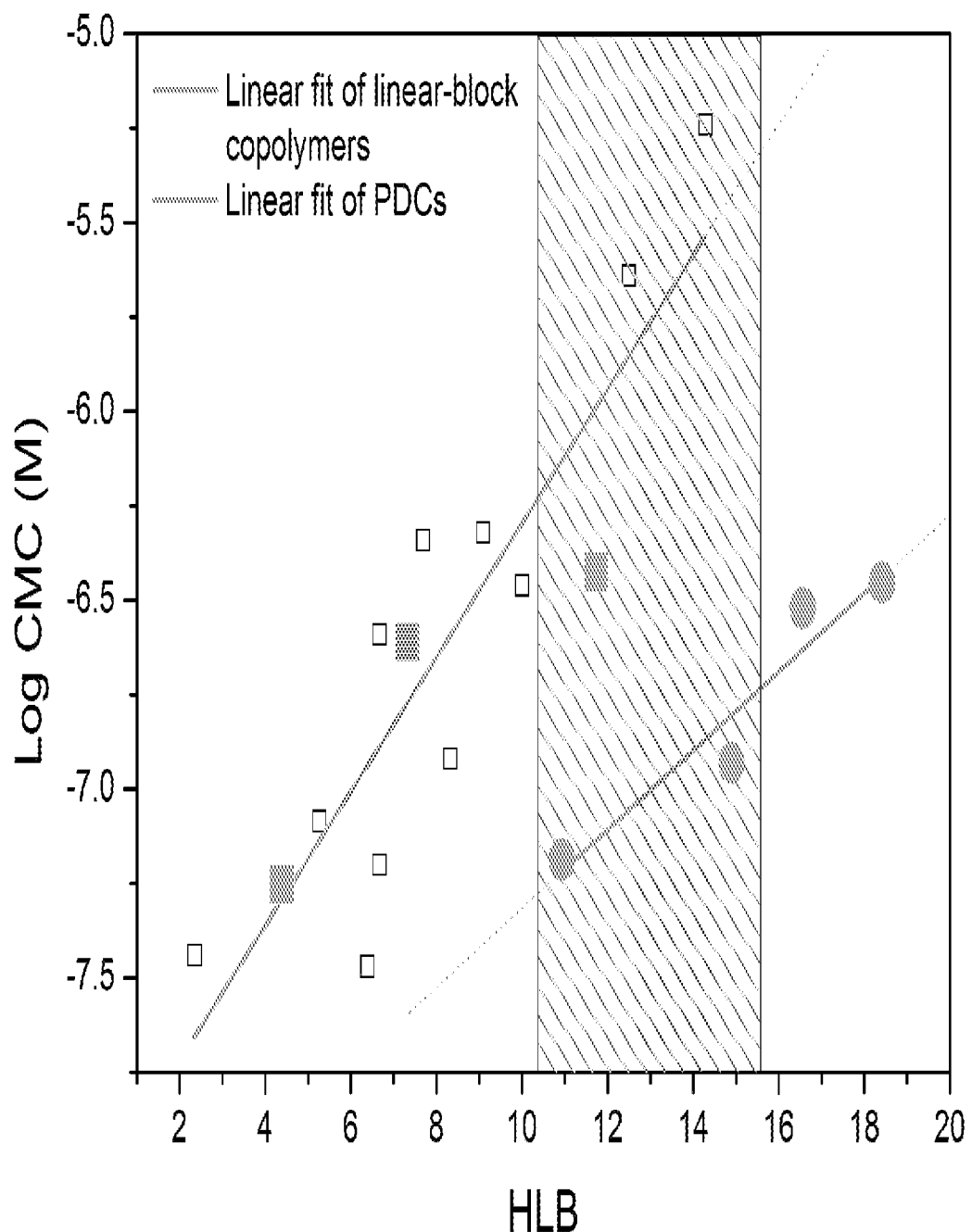
FIG. 10 shows a graph of the relationship between ln CMC and HLB for DC (circles) and linear-block copolymers (squares).

The CMC values of linear diblock copolymers were in good agreement with previous reports.[33a,35] The CMC values of the amphiphilic DCs were comparable to linear PCL-mPEG diblock copolymers even though in some cases, the HLB for amphiphilic DCs was twice as large (~90% hydrophilic). Amphiphilic DCs bearing PCL3.5K lipophilic blocks had similar CMC values to those of linear PCL-mPEG copolymers despite an average increase in HLB of 8 corresponding to a 40% increase in hydrophilicity. PCL14K-mPEG5K with the lowest HLB of all polymers tested at 5.26 was determined to have a CMC of $0.82 \times 10^{-7}$ M. Remarkably its counterpart, PCL14K-G3-mPEG5K with HLB of 14.90 had a CMC of $1.17 \times 10^{17}$ M. PCL14K-G3-mPEG2K was found to have the lowest CMC at $0.65 \times 10^{-7}$ M amongst all copolymers tested even with an HLB of 10.93. The presence of the dendron accounted for the dramatic increase in HLB observed in the amphiphilic DC structures, however this does not explain the preservation of low CMC values observed. Plotting ln CMC against HLB illustrates the relationship between HLB and CMC for the linear and amphiphile DCs (FIG. 10).[36] The notable shift to the right for the amphiphilie DCs towards higher HLBs without subsequent increase in ln CMC demonstrates that the thermodynamic stability of the amphiphilic DCs is superior to that of linear-block copolymers.

Figure 11:
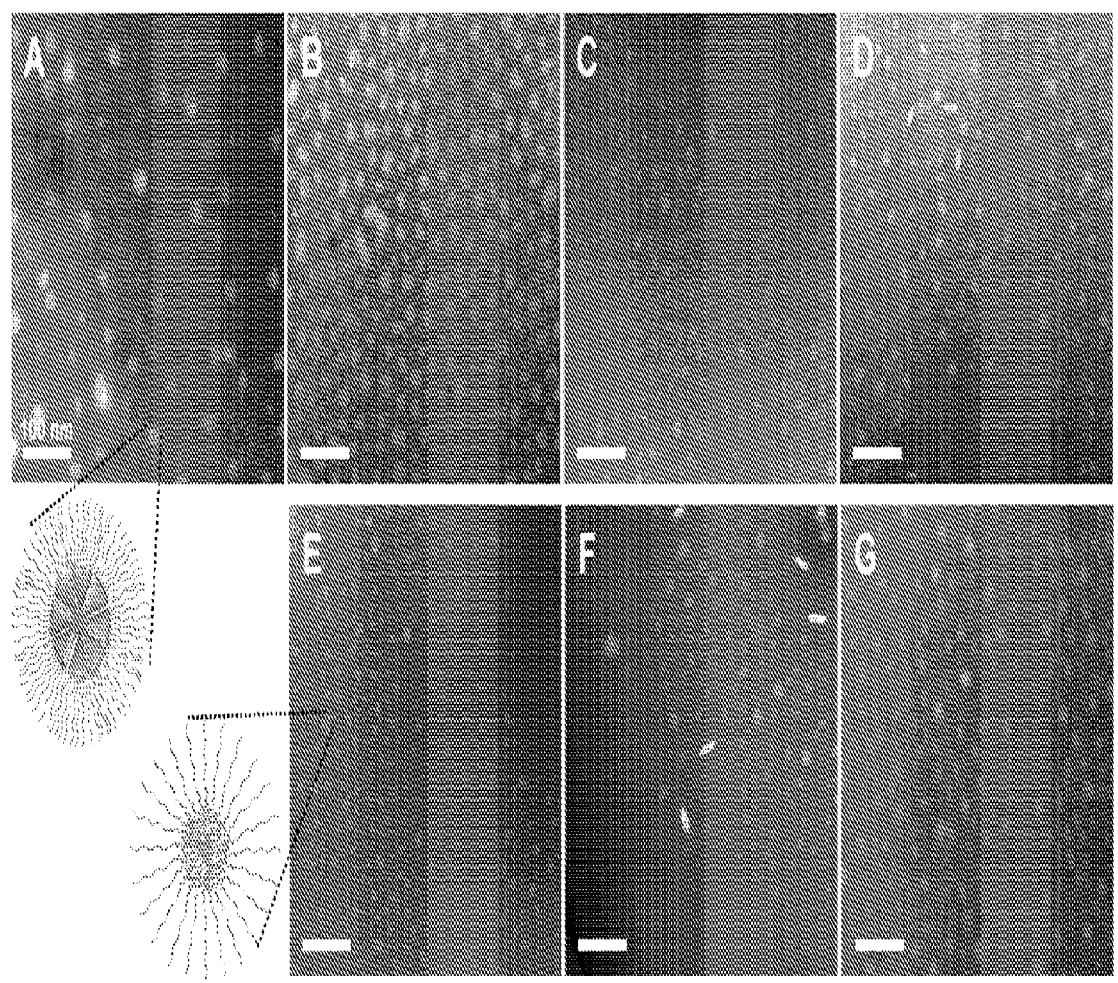
FIG. 11 shows transmission electron micrograph images of self-assembled structures. (Panel A) PCL3.5K-G3-mPEG2K, (Panel B) PCL3.5K-G3-mPEG5K, (Panel C) PCL14K-G3-mPEG2K, (Panel D) PCL14K-G3-mPEG5K, (Panel E) PCL3.5K-mPEG2K, (Panel F) PCL3.5K-mPEG5K, and (Panel G) PCL14K-mPEG5K. All samples were prepared at 0.2 mg/mL and stained with 2% Phosphotungstic Acid (pH 7). Scale bar=100 nm.

The size and morphology of self-assembled structures of the linear-block copolymers and amphiphilic DCs were examined using TEM and DLS. All samples were prepared at a concentration above their CMC by the dialysis method.[35a] As shown in FIG. 11, TEM images show that all DC micelles were spherical in shape and homogeneous in size, as similarly observed in the cases of the PCL-mPEG micelles. DC micelles (FIGS. 11C and D) with a longer PCL block were smaller in diameter than the micelles with PCL3.5K (FIGS. 11A and B). Average sizes of PCL3.5K-G3-mPEG2K and PCL3.5K-G3-mPEG5K micelles measured by DLS were approximately 18 nm. In contrast, PCL14K-G3-mPEG2K and PCL14K-G3-mPEG5K micelles were larger in size (30 and 50 nm, respectively).

Figure 12:
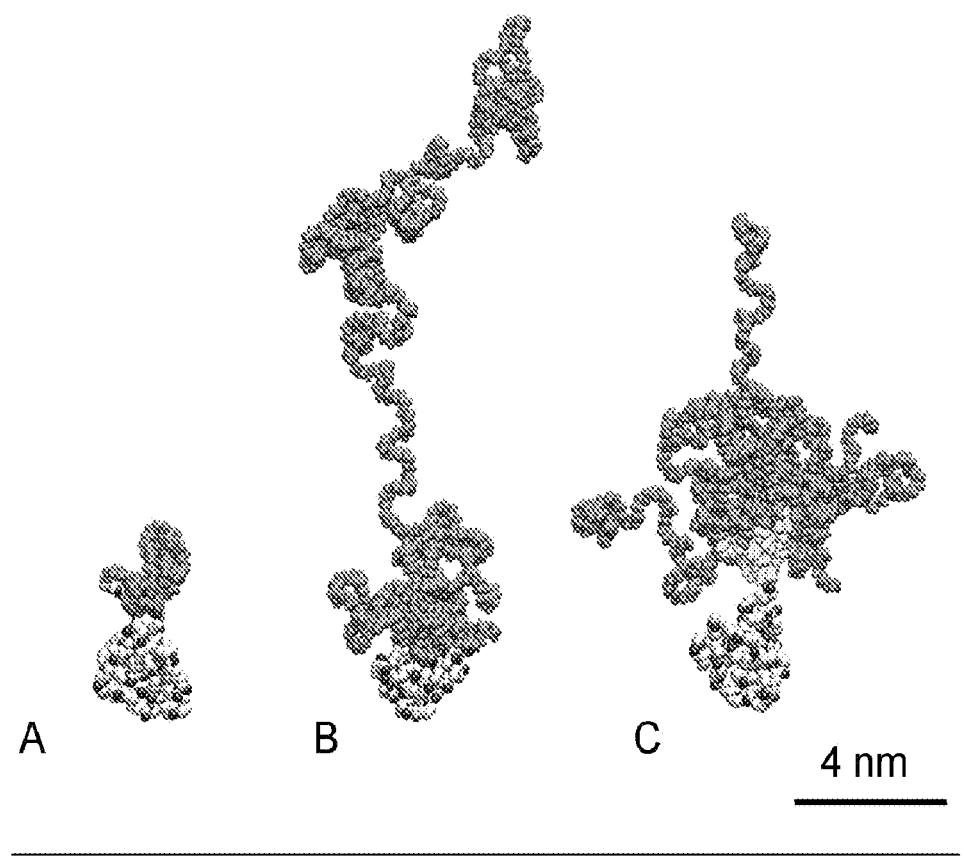
FIG. 12 shows MD simulation results for single (Panel a) PCL3.5K-mPEG2K, (Panel b) PC3.5K-mPEG16K and (Panel c) PCL3.5K-G3-mPEG2K monomers in water. (Panel d) PCL3.5K-mPEG2K micelle (number of monomers=128) and (Panel e) PCL3.5K-G3-mPEG2K micelle (number of monomers=14). PEG is shown in grey; PCL in white/black. Water is not shown for clarity. Scale bar=5 nm.
Figure 12:
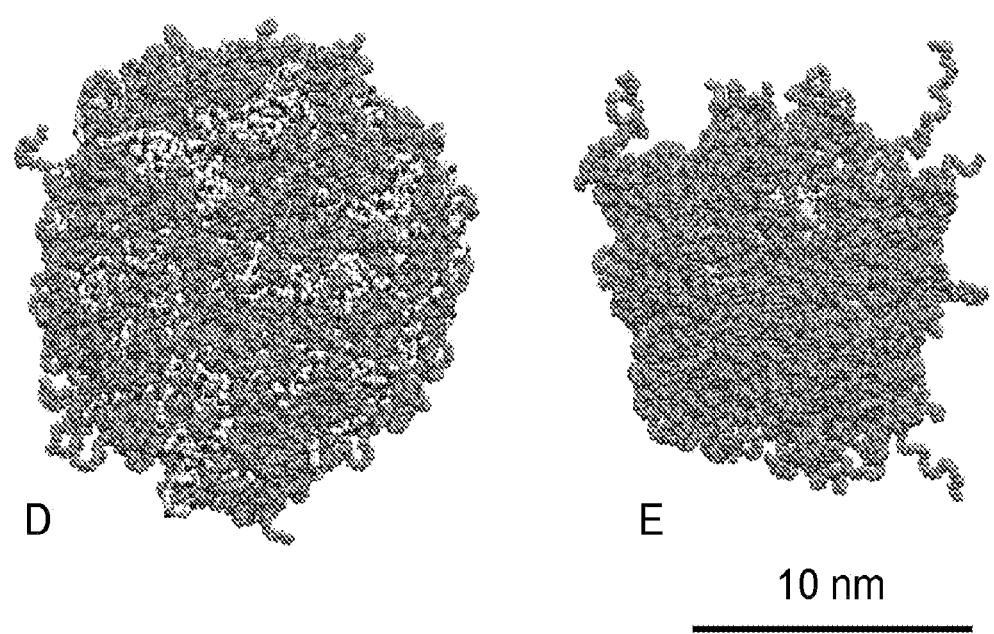

In order to understand in molecular detail the experimental observations, we modeled by atomistic molecular dynamics (MD) simulations single linear PCL3.5K-mPEG2K, PCL3.5K-mPEG16K and PCL3.5K-G3-mPEG2K in monomer and micelle forms (See details in Supporting Information). FIG. 12 shows the equilibrated structures after 5 nanoseconds (ns) of (Panel a) PCL3.5K-mPEG2K, (Panel b) PCL3.5K-mPEG16K, and (Panel c) PCL3.5K-G3-mPEG2K monomers in water and each was characterized in terms of their size and shape. In all the monomers, a compact PCL tail and an extended conformation of the PEG blocks due to their solvation in water was observed. The sizes of the compact PCL blocks are similar in all three cases, whereas there is a distinct difference in the sizes of the PEG layer for each. Monomers (Panel b) and (Panel c), which have the same molecular weight of PEG blocks and identical HLBs, do not have the same conformation of PEG blocks due to differences in molecular geometry. The simulation revealed that the eight grafted PEG chains on the amphiphilic DC adopt a fan-like shape (in comparison to a single PEG chain solvated in water) due to the pre-organized architecture of the dendron allowing a conical shape to be adopted. The conical morphology is a result of the hydrophobic effect[37] where the compaction of the PCL tail occurs to minimize the entropic loss of water reducing the energy at the PCL-water interface. Additionally, the observed increase in peripheral surface area for the amphiphilic DC can be attributed to steric repulsive forces between mPEG chains and high mPEG density.

We also simulated micellar assemblies of PCL3.5K-mPEG2K and PCL3.5K-G3-mPEG2K to understand the experimentally observed morphologies. FIG. 12 shows micelles formed from (Panel d) 128 monomers of PCL3.5K-mPEG2K and (Panel e) 14 monomers of PCL3.5K-G3-mPEG2K equilibrated in water for 5 ns. Micelle aggregation number ($N_{agg}$) for each was chosen to best represent the observed sizes of linear and DC micelles by TEM. Indeed, the aggregation number for PCL3.5K-mPEG2K micelles were quite close to the experimentally measured aggregation numbers of micelles with a similar structure.[38] In all equilibrated micelles, either two or three unique regions were recognizable: PCL core and PEG corona, or PCL core, dendron and PEG corona. The micelle cores were found to reorganize only slightly during several ns to form a spherical shape. In a separate simulation, a PCL3.5K-G3-mPEG2K micelle with 18 monomers was prepared and showed a distorted elongated shape. Therefore, we can conclude that spherical micelles can be observed for amphiphilic DC $N_{agg}$<18.

The stability and self-assembly behaviors of amphiphilic DCs is contradictory to current thought that copolymers with large HLBs have high CMCs. We used a simple analytic model to examine the entropic cost associated with the confinement of hydrophilic PEG blocks when in the micellar phase. To estimate the approximate entropic cost, it is assumed that PEG can be described within the framework of ideal chain theory.[39] An ideal chain of length L is comprised of n segments, each of statistical segment length l, so that L=ln. When placed in a good solvent (such as water), the PEG chain swells to maximize the number of polymer-fluid contacts. Configurations of the ideal chain can be characterized by a probability distribution function which depends on the chain end-to-end (e-t-e) distance. An ideal chain has a well defined average e-t-e distance $<r>=ln^{1/2}$ which is associated with minimum (configuration) free energy of the polymer. When the PEG becomes confined during self-assembly process, its average e-t-e distance will increase and the free energy cost associated with this extension is purely entropic. Entropy of a freely jointed chain with a given e-t-e distance is proportional to the logarithm of the number of chain configurations for that e-t-e distance. This is in turn proportional to the probability of the PEG having this e-t-e distance. The entropy difference between PEG chains in a given conformation with different e-t-c extensions is given by:[39] $\Delta S = S - S_1 = k_B b^2 (r_1^2 - r^2)$ where S and $S_1$ are configurational entropies associated with e-t-e extensions r and $r_1$, $k_B$ is the Boltzmann constant and $b^2 = 3/(2 nl^2)$.

For PCL3.5K-mPEG16K polymer, the PEG block has n=363 segments, each of the length l=3.68 Å. In water, the average e-t-e distance of this polymer is $<r>=ln^{1/2} \approx 70$ Å. Assume that due to steric confinement the e-t-e distance of the chains in the micelle is extended by 50% from the above value of $<r>$, the entropic cost for this extension is 1.11 kcal/mol≈1.9 $k_B T$. Since every chain forming a micelle needs to pay this configurational entropic cost, the micelle formation is not favorable for polymers with long hydrophilic blocks. Previously, we had hypothesized that the dendron geometry facilitates self-assembly of copolymers with high HLB due to low entropic costs. For amphiphilic DC monomers solvated in water, eight grafted PEG chains are forced to assume extended conformations due to their density and steric repulsion. When these copolymers form micelles, further extensions of the PEG blocks are likely small, in good agreement with the results of our MD simulations. Since the average e-t-e extensions of PEG of DC in solvated and micellar phases are similar, the associated conformational entropy cost is also small compared to the enthalpic binding, resulting in micellar phase being favored. For linear polymers, extensions of PEG will be considerable, resulting in larger differences in conformational entropies in monomer and aggregated states accounting for their increased CMC values compared to DCs with the same HLBs.

There are several pieces of evidence suggesting that certain geometric constraints placed on amphiphilic molecules enables the minimization of the free energy associated with the self-assembly process.[40b,41] Using geometrical relationships developed by Nagarajan[42], it is clearly observed that DCs will have a smaller aggregation number, g, than linear copolymers with the same tail length. Based on Tanford's free energy expression as described by Nagarajan[42], minimization of free energy results in low CMCs. The high flexibility and number of PEG on the exterior of each DC can promote the dense packing of monomers which results in a decrease in CMC as observed in the measured dimensions for each micelle (Table 3).[43]

TABLE 3

Dependence of the total micelle diameter ($d_{total}$), core diameter ($d_{core}$) and PEG corona diameter ($d_{PEG}$) based on aggregation number ($N_{agg}$) and monomer type. These values are obtained by angular averaging (2-5 ns) of the radial extensions of the PEG chains with respect to the micelle center of mass.

| Samples | $N_{agg}$ | $d_{total}$ (nm) | $d_{core}$ (nm) | $d_{PEG}$ (nm) |
| --- | --- | --- | --- | --- |
| PCL3.5K-mPEG2K | 86 | 12.94 | 11.44 | 0.75 |
| PCL3.5K-mPEG2K | 128 | 15.22 | 13.54 | 0.84 |
| PCL3.5K-G3-mPEG2K | 14 | 13.42 | 7.68 | 2.87 |
| PCL14K-G3-mPEG2K | 10 | 12.98 | 9.18 | 1.91 |

The results presented here support our hypothesis that the self-assembly process of amphiphilic DCs is more thermodynamically favored than linear PCL-mPEG copolymers and that entropic effects attribute greatly to the increased stability of amphiphilic DCs with large HLBs. In comparison to linear-block copolymers, our results indicate that the molecular structure of the DC: (1) enables the self-assembly process to be thermodynamically favored resulting in ultralow CMC values and homogeneous size distributions of self-assembled structures; and (2) the entropy cost associated with the self-assembly of DCs is much lower than linear-block copolymer counterparts even with high HLBs due to the preorganized dendron architecture.

In order to test the capability of DC micelles as drug delivery vehicles, indomethacin (IMC) was encapsulated into micelles. IMC loading and encapsulation percentages were calculated, and a drug release test and cytotoxicity test were carried out.

The IMC loading and encapsulation percentages were calculated as Loading (%)=(Measured IMC amount/Mass of IMC loaded micelle)×100(%) and Encapsulation (%)=(Measured IMC amount/Theoretical IMC loading amount)×100(%). As shown in Table 4, the encapsulation efficiencies (%) were significantly different between PCL3.5K-G3-mPEG2K and PCL3.5K-G3-mPEG5K IMC loaded micelles based on a 1-way ANOVA followed by Tukey's post-hoc test at p<0.05.

TABLE 4

IMC loading and encapsulation of various micelles (n = 3).

| Samples | Loading (%) | Encapsulation (%) | IMC/PCL ratio |
| --- | --- | --- | --- |
| PCL3.5K- mPEG2K | 6.7 ± 0.3 | 73.9 ± 3.3 | 1.62 |
| PCL3.5K- mPEG5K | 7.8 ± 0.7 | 85.7 ± 7.6 | 4.50 |
| PCL14K- mPEG5K | 8.4 ± 0.2 | 92.7 ± 2.4 | 6.05 |
| PCL3.5K-G3-mPEG2K | 8.3 ± 0.5 | 90.8 ± 5.6 | 32.05 |
| PCL3.5K-G3-mPEG5K | 5.0 ± 0.4 | 54.9 ± 3.9 | 79.83 |
| PCL14K-G3-mPEG2K | 9.3 ± 2.4 | 102.7 ± 25.8 | 19.60 |
| PCL14K-G3-mPEG5K | 6.2 ± 2.8 | 68.4 ± 31.2 | 37.75 |

The differences among all other samples were not statistically significant. IMC/PCL ratio represents the moles of IMC encapsulated per mole of PCL present in the copolymer, demonstrating that the amount of IMC encapsulated per amount of PCL was one order of magnitude greater than that of the linear-block copolymer micelles. The IMC/PCL ratios were calculated based on following. For the example of PCL3.5K-G3-mPEG2K, assuming 1 mg of drug encapsulated micelle, (1 mg/21990 mg/mmol)×(3500 mg PCL/21990 mg micelle)=7.238×10$^{-6}$ mmol PCL. Calculating the mass of IMC contained within 1 mg of micelle (loading) and converting to moles IMC: (0.083 mg IMC)×(1 mmol/357.79 mg IMC)=2.320×10$^{-4}$ mmol IMC. Therefore, IMC/PCL ratio=2.320×10$^{-4}$ mmol IMC/7.238×10$^{-6}$ mmol PCL=32.05.

Figure 13:
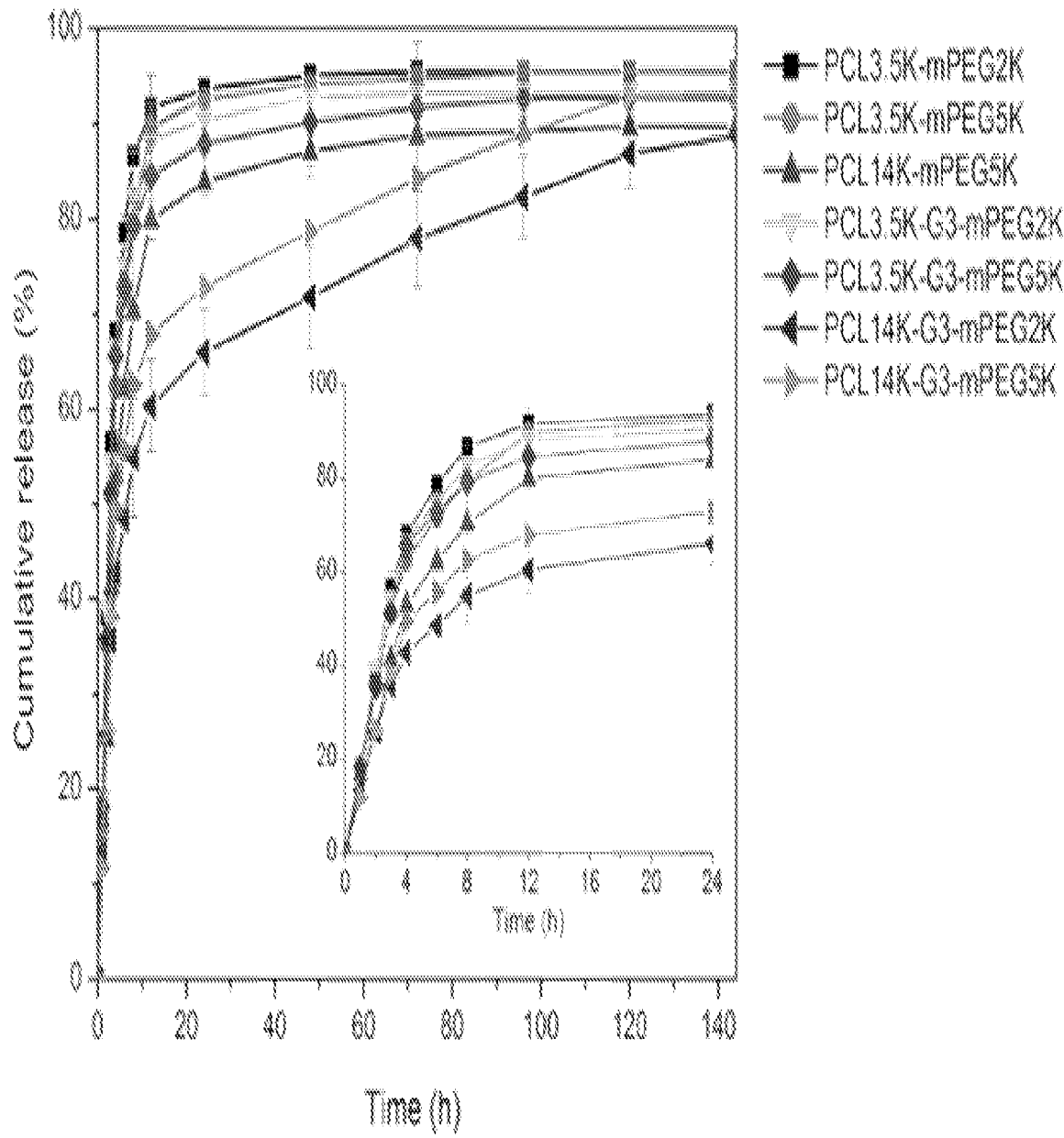
FIG. 13 shows release profiles of IMC from various micelles for 6 days. Inset: release profiles of various micelles over the first 24 h.
Figure 14:
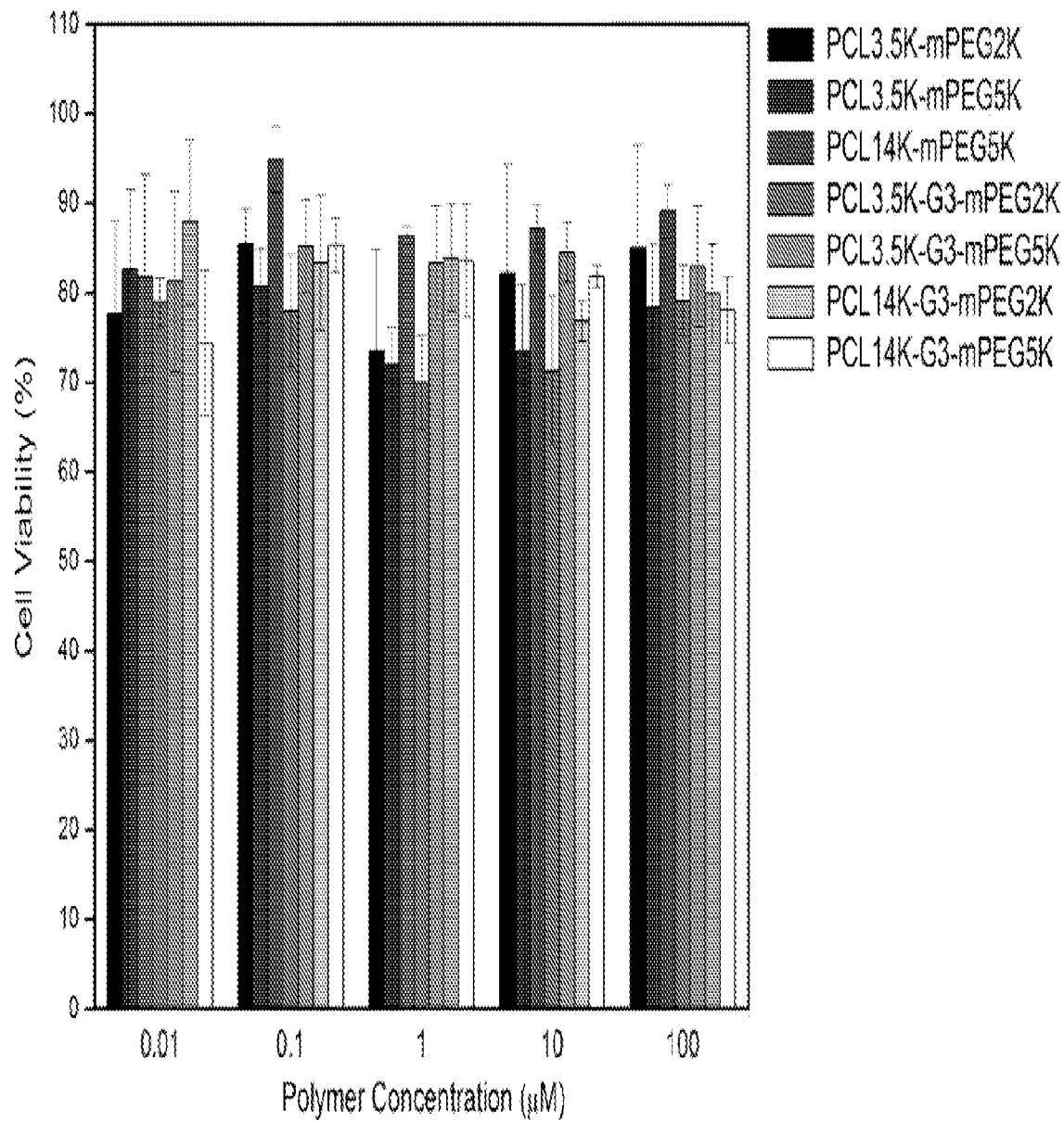
FIG. 14 shows MTS assay results for cell viability of KB cells after 24 h incubation with various block copolymers. All data were expressed as the mean of triplicate cultures. All the polymers do not exhibit significant toxicity in the range of concentrations as high as 100 μM.

FIG. 13 shows controlled release of IMC from the micelles over time, There were no difference in the IMC release profiles between PCL-G3-mPEG and PCL-mPEG micelles. A noticeable difference was observed with the micelles with PCL14K during the first 24 h. This is probably due to increased hydrophobic interactions between PCL and IMC as well as more packed micellar structures leading to a slower rate of diffusion. The cytotoxicity of the various copolymers was evaluated on KB cells after 24 h incubation by MTS assay (FIG. 14). All copolymers did not exhibit significant cytotoxicity at concentrations up to 100 μM.

Thus, we report the synthesis of four newly designed amphiphilic DCs with different HLBs that are composed of PCL, G3 polyester dendron and mPEG. The results from a systematic study of the self-assembly properties of amphiphilic DCs compared to the linear-block copolymers explain that a preorganized and conical architecture of dendron can contribute to facilitate a self-assembly of amphiphilic DCs. In particular, the self-assembling pwcess mediated by the dendron is thermodynamically favored resulting in ultra low CMCs even at extremely high HLBs, which is also supported by MD simulations. The DC micelles showed controlled drug release behaviors as well as good biocompatibility. The facilitated supramolecular structure formation at ultra low CMCs and high HLBs, along with the biocompatibility, all prove that the DC micelles have great potential for use as a versatile drug delivery platform.

Supporting Information for Example 2

Materials

Hydroxyl-terminated poly(ε-caprolactone) (PCL) polymers with two different molecular weights ($M_n$ 3500 and PDI 1.18, $M_n$ 14000 and PDI 1.20) were purchased from Polymer Source Inc. (Montreal, Canada). Generation 3 polyester-8-hydroxyl-1-acetylene bis-MPA dendron (G3 dendron; G3), p-toluenesulfonyl chloride (TsCl), 2-bromoethyl isocyanate (BEI), triethylamine (TEA), trimethylamine hydrochloride (TMA), sodium azide (NaN$_3$), anhydrous sodium sulfate, N,N,N',N'',N''-pentamethyldiethylenetriamine (PMDETA), copper bromide (CuBr), dibutyltin dilaurate (DBTDL), and p-nitrophenyl chloroformate (p-NPC) and indomethacin (IMC) were all provided by Sigma Aldrich Co. (St. Louis, USA). Methoxy polyethylene glycol amine (mPEG-NH$_2$, $M_n$ 2000 and PDI 1.02, $M_n$ 5000 and PDI 1.04) was purchased from JenKem Technology USA Inc. (TX, USA). Regenerated cellulose dialysis membranes (3.5K and 12-14K MWCO) were purchased from Spectrum Labs (CA, USA). All solvents and reagents were used without further purification unless otherwise specified.

Synthesis of PCL3.5K-G3 Dendron Via Click Reaction

Tosylation of PCL3.5K. A terminal hydroxyl group of PCL was firstly tosylated prior to introduction of an azide group as previously reported (FIG. 4).[44] PCL3.5K (1 g, 0.286 mmol) along with TEA (200 μl, 1.43 mmol) and trimethylamine hydrochloride (14 mg, 0.143 mmol) were dissolved in 8 mL of dichloromethane. To this solution, TsCl (272 mg, 1.430 mmol, 5 eq.) dissolved in 2 mL of dichloromethane was added dropwise. The reaction was carried out at room temperature for 24 h. Following the reaction, the solvent was evaporated until a viscous liquid remained. The viscous liquid was then precipitated into cold diethyl ether, filtered, and dried in vacuo (Yield: 90%).

Azido-functionalization of PCL3.5K-Ts. The tosyl group of PCL3.5K-Ts was converted into azide for subsequent click chemistry. PCL3.5K-Ts (840 mg, 0.24 mmol) was dissolved in 8 mL of dimethylformamide. To this solution, sodium azide (312 mg, 4.8 mmol, 20 eq.) was added and reacted at room temperature for 24 h under N$_2$. The reaction mixture was diluted with 200 mL of dichloromethane and washed three times with 150 mL of deionized water and once with 200 mL of brine. The organic layer was dried over anhydrous sodium sulfate, filtered, concentrated, and precipitated into cold diethyl ether (Yield: 70%).

Synthesis of PCL3.5K-G3 dendron. PCL3.5K-G3 dendron was synthesized via click chemistry between PCL3.5K-N$_3$ and G3 dendron bearing an acetylene group in the presence of copper (I) and a base by modification of a previously reported method.[2] PCL3.5K-N$_3$ (73 mg, 0.021 mmol) and G3 dendron (20 mg, 0.023 mmol, 1.1 eq.) were dissolved in 2 mL of dimethylformamide containing PMDETA (7.3 mg, 0.042 mmol, 2 eq.). After dissolving, copper bromide (6 mg, 0.042 mmol, 2 eq.) was added and the reaction was carried out at 80° C. for 24 h. Products were recovered by precipitation into cold diethyl ether and filtration (Yield: 96%).

Synthesis of PCL14K-G3 Dendron Via Click Reaction

Bromination of PCL14K. The terminal hydroxyl group of high molecular weight PCL was easily converted into bromide by reaction with 2-bromoethyl isocyanate (Figure S1B). PCL14K (1 g, 0.071 mmol) was dissolved in 15 mL of toluene containing TEA (11 μl, 0.071 mmol) with a catalytic amount of DBTDL. To this solution, 1 mL of toluene containing 2-bromoethyl isocyanate (108 mg, 0.714 mmol, 10 eq.) was added dropwise and reacted at room temperature for 24 h under N$_2$. Following the reaction, the solvent was evaporated until a viscous liquid remained. The viscous liquid was then precipitated into cold diethyl ether, filtered and dried in vacuo (Yield: 92%).

Azido-functionalization of PCL14K-Br. The bromine group of PCL14K-Br was converted into azide for click chemistry. PCL14K-Br (910 mg, 0.065 mmol) was dissolved in 12 mL of dimethylformamide. To this solution, sodium azide (84 mg, 1.3 mmol, 20 eq.) was added and reacted at room temperature for 24 h under N$_2$. The reaction mixture was diluted with 200 mL of dichloromethane and washed three times with 150 mL of deionized water and once with 200 mL of brine. The organic layer was dried over anhydrous sodium sulfate, filtered, concentrated and precipitated into cold diethyl ether (Yield: 81%).

Synthesis of PCL14K-G3 dendron. PCL14K-G3 dendron was synthesized via click chemistry between PCL14K-N$_3$ and G3 dendron bearing an acetylene group in the presence of copper (I) and a base by modification of a previously reported method.[45] PCL14K-N$_3$ (200 mg, 0.0143 mmol) and G3 dendron (16 mg, 0.0157 mmol, 1.1 eq.) were dissolved in 3 mL of dimethylformamide containing PMDETA (4.94 mg, 0.0286 mmol, 2 eq.). After dissolving, copper bromide (4 mg, 0.0286 mmol, 2 eq.) was added and the reaction was carried out at 80° C. for 24 h. Products were recovered by precipitation into cold diethyl ether and filtration (Yield: 95%).

mPEG Conjugation to PCL-G3 Dendron mPEG conjugation was accomplished following activation of the peripheral hydroxyl groups on PCL-G3 dendron (FIG.

5).[46] PCL-G3 dendron was dissolved in 8 mL of dichloromethane containing pyridine (5 eq.). After adding p-NPC (5 eq.) dropwise, the reaction was carried out at room temperature for 24 h. The solvent was evaporated until a viscous liquid remained. The viscous liquid was then precipitated into cold diethyl ether, filtered and dried in vacuo. For mPEG conjugation, a solution of the activated PCL-G3 dissolved in 1 mL of dimethylformamide was added dropwise to 3 mL of dimethylformamide containing mPEG-$NH_2$ (1.2 eq.) and TEA (4 eq.). The reaction was carried out at room temperature for 24 h. The solution was then transferred into a dialysis bag (MWCO 3.5K for mPEG2K-$NH_2$ and MWCO 12-14K for mPEG5K-$NH_2$), dialyzed for 2 days, and then freeze dried for 2 days (Yields: >70%).

Synthesis of Linear PCL-mPEG Copolymers 300 mg of PCL was dissolved in 8 mL of dichloromethane containing pyridine (5 eq.). After adding p-NPC (5 eq.) dropwise, the reaction was carried out at room temperature for 24 h. The solvent was evaporated until a viscous liquid remained. The viscous liquid was then precipitated into cold diethyl ether, filtered and dried in vacuo (Yields: >90%). A solution of the activated PCL dissolved in 1 mL of dimethylformamide was added dropwise to 3 mL of dimethylformamide containing mPEG-$NH_2$ (1.2 eq.) and TEA (4 eq.) and reacted at room temperature for 24 h. The crude product was transferred into a dialysis bag, dialyzed for 1 day and then freeze dried for 2 days (Yields: >80%). For PCL14K-mPEG copolymers, the extraction method was used due to their low HLB values (Yields: >60%).

Polymer Characterization $^1$H-NMR spectra were recorded at 400 MHz (DPX-400 NMR spectrometer, Bruker Biospin Co., MA, USA). NMR chemical shifts are reported in ppm with calibration against a solvent signal. FT-IR spectra were recorded using FT-IR spectrophotometer (NEXUS 870, Thermo Nicolet Co., WI, USA). GPC measurements were carried out using a 600 HPLC pump, 717plus Autosampler, 2414 Refractive Index detector (Waters, Milford, Mass., USA) and a MiniDAWN™ TREOS triple-angle light scattering detector (Wyatt, Santa Barbara, Calif., USA) using THF as the mobile phase at 1 mL/min with Waters Styragel® HR2 and HR4E columns at 30° C.

Additional Synthetic Description

Figure 15A:
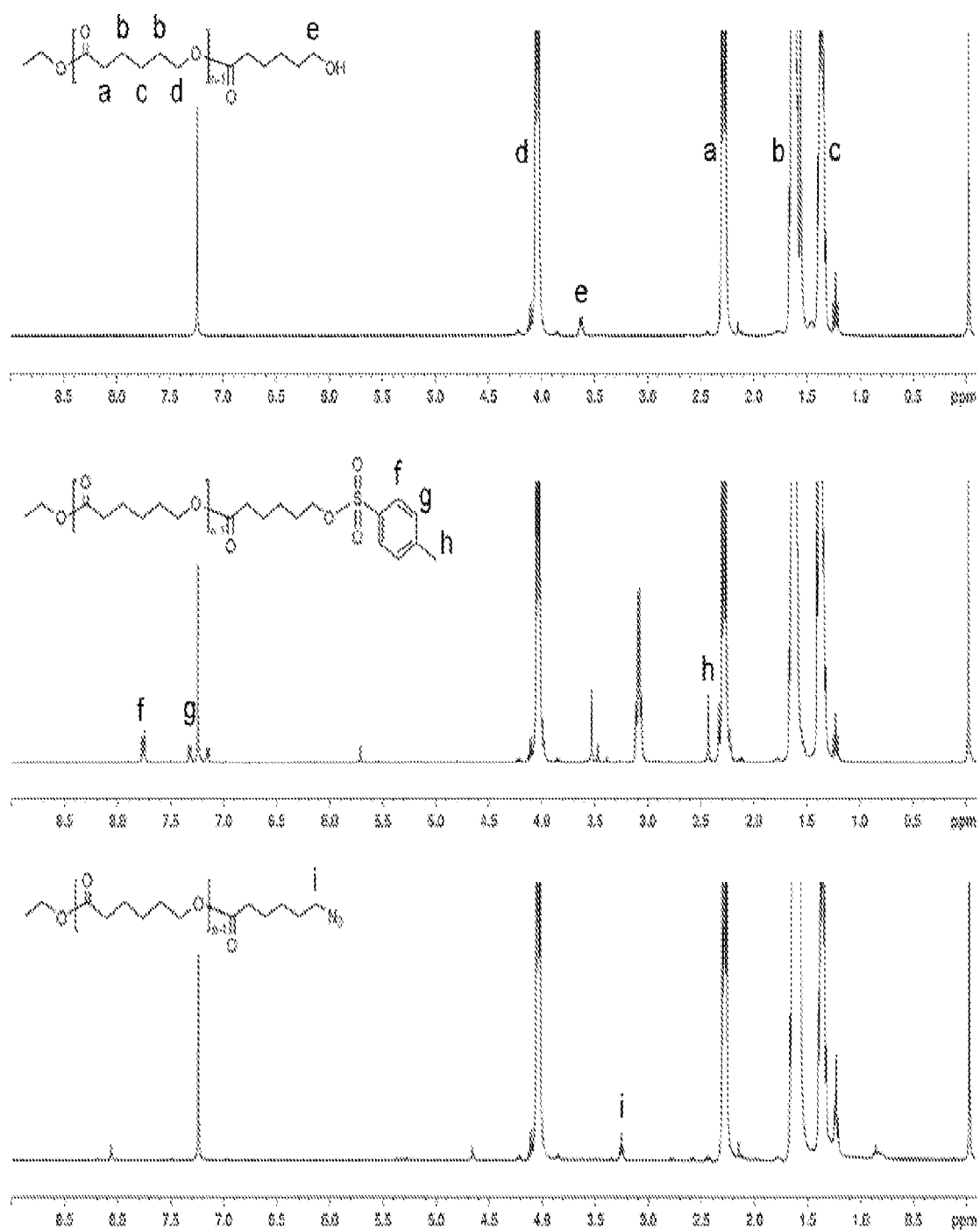
FIG. 15 shows $^1$H-NMR spectra of PCL3.5K (Panel A) and PCL14K derivatives (Panel B). The peaks corresponding to two protons adjacent to a hydroxyl group of PCL ("e" for PCL3.5K and "a" for PCL14K) completely disappeared after the reactions. The peak shifts of PCL14K between 3.7 and 3.2 were clearly observed according to each reaction step.
Figure 15B:
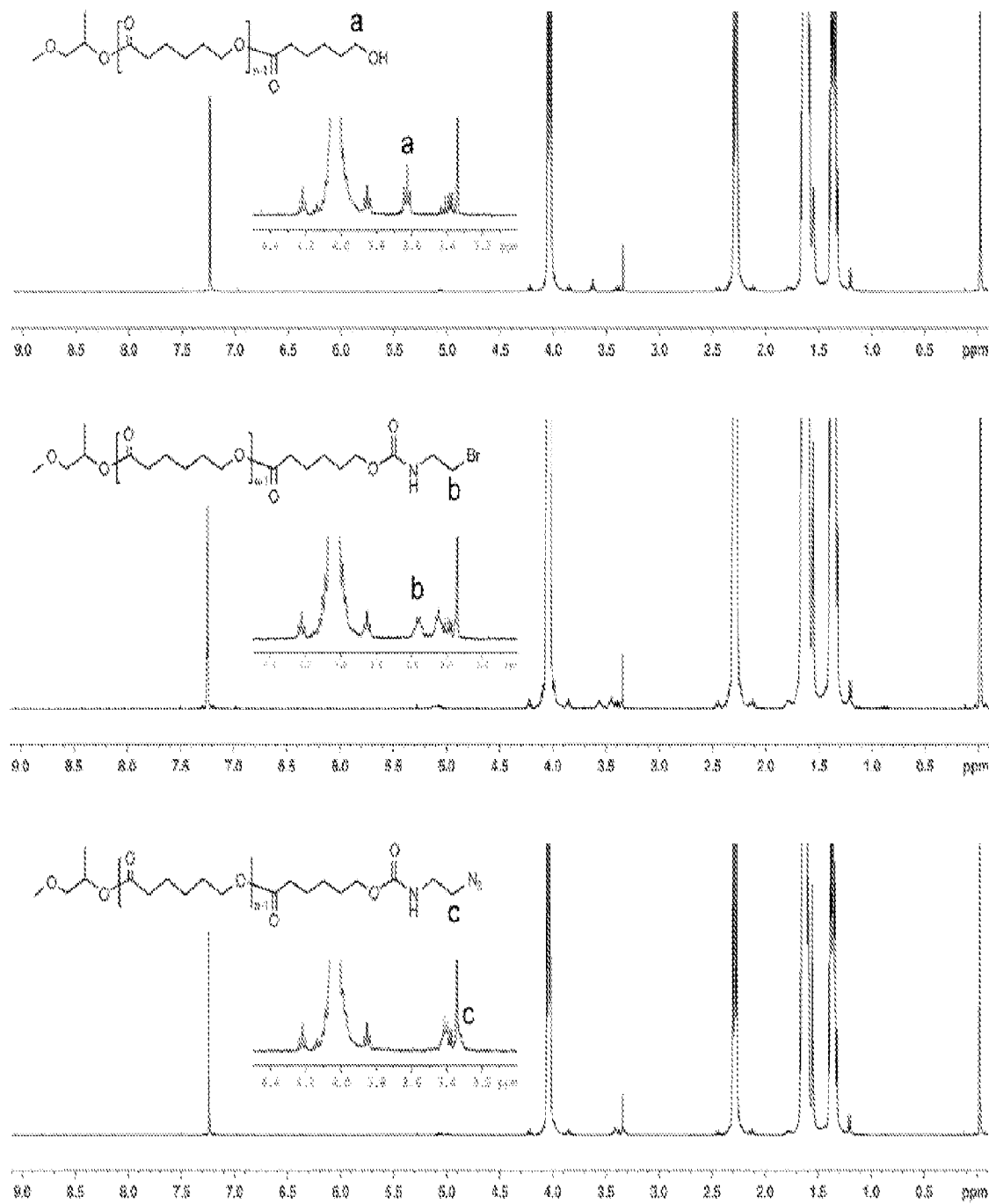

The terminal hydroxyl groups of both PCL3.5K and PCL14K were completely substituted into a tosyl group and bromide, respectively (FIG. 15). The identical method for both molecular weights of PCL was first attempted, however effective substitution was not observed for high molecular weight PCL with p-toluenesulfonyl chloride and the alternative method was chosen due to the high reactivity of the isocyanate group with hydroxyl groups as well as the ease of nucleophilic substitution of bromine for azide.

G3 polyester dendron bearing an acetylene functional group at the focal point was reacted with PCL-$N_3$ via click chemistry. Although click chemistry has been shown to be efficient under mild conditions, a variety of reaction conditions have been developed that vary in terms copper species, bases, solvents and temperatures further increase conjugation yields.[47] The click reaction between PCL-$N_3$ and G3 dendron was firstly catalyzed by 0.2 equivalent amounts of CuBr and PMDETA based on the feed molar amount of PCL-$N_3$ in DMF at room temperature as previously reported.[48] However, the conjugation yield was calculated to be less than 10% by $^1$H-NMR with no appearance of characteristic protons associated with triazole formation. According to few reports on the failure of click reactions,[49] we investigated the efficiency of the click reaction with a variety of conditions; copper species ($CuSO_4$, CuBr, CuI), sodium ascorbate, bases (PMDETA, diazobicyclo[5.4.0undec-7-ene]), solvents (DMF and THF), temperatures (30, 50, and 80° C.). It was found that the click reaction using CuBr and PMDETA in DMF at 80° C. afforded the desired PCL-G3 products with high conjugation yields (PCL3.5K-G3: 70%; PCL14K-G3: 80%).

Micelle Preparation and Characterization

For blank micelles, 20 mg of polymer was dissolved in 2 mL of dimethylformamide. The solution was dialyzed (MWCO 3.5K) against distilled water for 1 day and freeze dried for 2 days. IMC was chosen as a model hydrophobic drug. IMC-loaded micelles were prepared by a dialysis method. 40 mg of polymer was dissolved in 4 mL of dimethylformamide along with 4 mg of IMC. The polymer-IMC solution was then transferred to a dialysis membrane (MWCO 3500), dialyzed for 24 h against 2 L of distilled water, and freeze dried for 2 days to produce IMC-loaded micelles.

Figure 16:
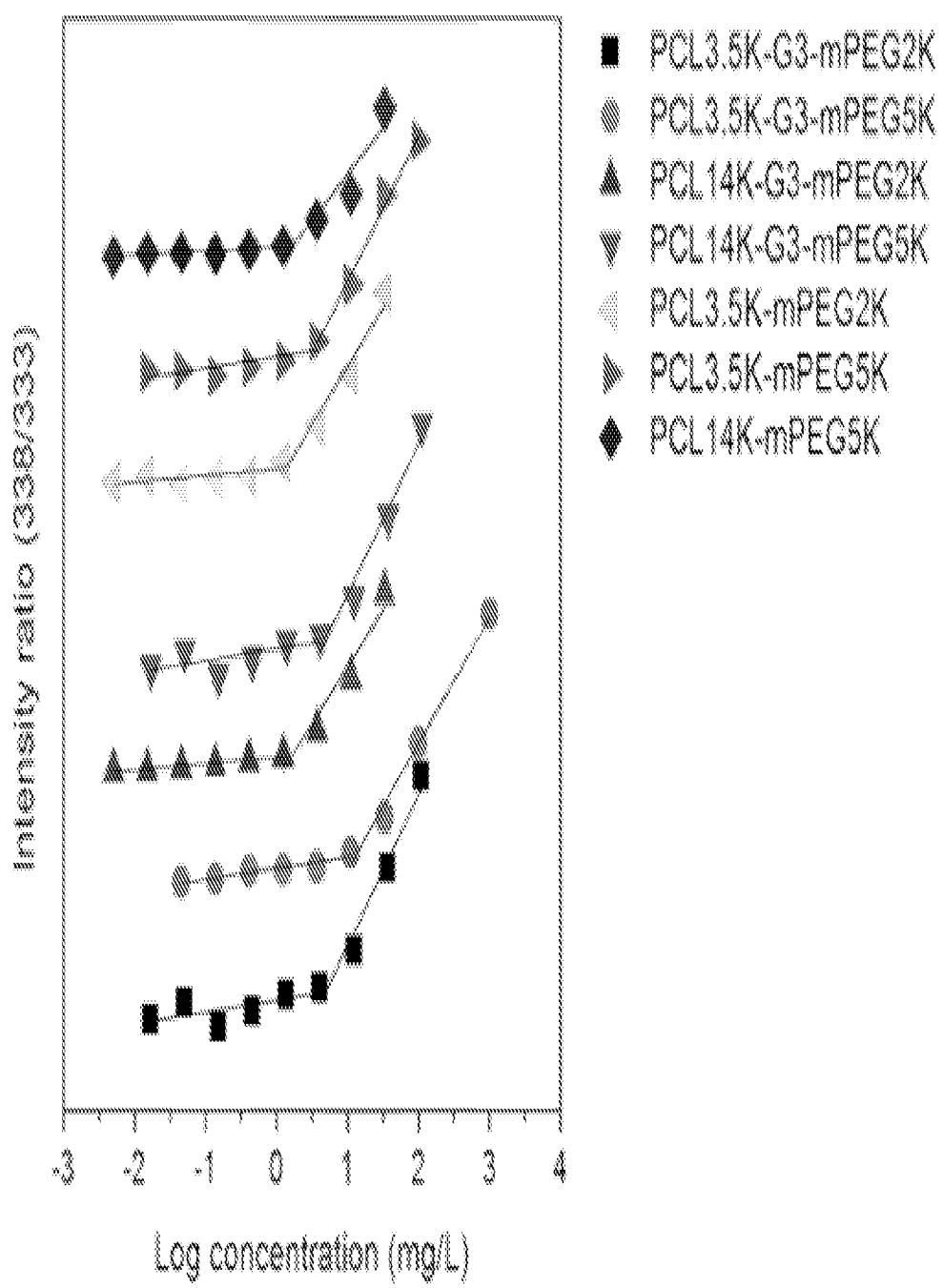
FIG. 16 shows plots of fluorescence intensity ratios against log concentrations of copolymers. The transition points indicate the CMC results of various PCL-G3-mPEG and PCL-mPEG copolymers.

Critical micelle concentration (CMC) was determined by using a fluorescence method as previously reported.[50] Briefly, a known amount of pyrene dissolved in acetone was added to a series of vials and evaporated such that upon addition of 2 mL of polymer solution the concentration of pyrene was $6\times10^{-7}$ M. The copolymers dissolved in water ($10^3$-$10^{-3}$ mg/L) was added to each vial containing pyrene and before fluorescence measurement the solutions were vortexed and incubated at room temperature for 24 h. The emission wavelength $\lambda_{em}$ was set at 390 nm and the $\lambda_{ex}$ was scanned from 300 nm to 400 nm using a spectrofluorophotometer (RF 1501, Shimadzu, Japan) and the intensity ratio $I_{338}/I_{333}$ against log concentration was plotted. See FIG. 16.

The particle size (nm) and size distribution were measured for all micelles by dynamic light scattering (DLS) using a Nicomp 380 Zeta Potential/Particle Sizer (Particle Sizing Systems, Santa Barbara, Calif.). Micelles were prepared at concentrations above their measured CMCs in distilled water, filtered through a 0.45 μm syringe filter, and vortexed briefly before each measurement. The micellar morphology was analyzed by transmission electron microscopy (TEM, JEM-1220, JEOL Ltd., Japan). A drop of micellar suspension (0.2 mg/ml) after filtration (pore size, 0.45 μm) was placed on a 300 mesh copper grid coated with carbon. The sample was stained with a drop of 2% phosphotungstic acid and dried at room temperature in a desiccator for 1 day. The diameters of each micelle were measured by randomly selected 10 particles from each TEM image. The average and standard deviation were calculated.

Drug Release Test

To determine the IMC-loading content, a small amount of IMC-loaded micelles was dissolved in 1 mL of dimethylformamide and the concentration of IMC was determined by measuring the UV-absorbance at 317 nm from a series of IMC standards in dimethylformamide. 10 mg of IMC-loaded micelles was suspended in 1 mL of PBS (pH 7.4, 0.01 M) and transferred to a dialysis bag (MWCO 3.5K). Each dialysis bag was added to 30 mL of PBS and placed into a shaking water bath (37° C., 50 rpm). At predetermined time intervals, 10 mL of release medium was removed and replaced with fresh PBS and frozen until all samples were collected. Samples were then freeze-dried for 2 days, redissolved in 1 mL DMSO and centrifuged at 4000 rpm at room temperature. The amount of IMC released was obtained by measuring the UV-absorbance of the supernatant at 317 nm and comparing to a standard curve of IMC in DMSO. The release profile was obtained by plotting the cumulative IMC release against time.

Cytotoxicity Test

KB cell line was obtained from ATCC (Manassas, Va., USA) and grown continuously as a monolayer in GIBCO RPMI 1640 medium (Invitrogen Corporation, Carlsbad, Calif., USA) in a humidified incubator at 37° C. and 5% $CO_2$. RPMI was supplemented with penicillin (100 units/ml), streptomycin (100 mg/ml), and 10% heat-inactivated fetal bovine serum (FBS) (Invitrogen Corporation, Carlsbad, Calif., USA) before use. For the assay, KB cells were seeded in 96-well plates at a density of $5 \times 10^3$ cells/well and grown in RPMI for 24 h. Cells were then treated with different concentrations of each copolymer ranging from 0.01-100 μM. After each incubation time, cells were washed and incubated for an additional 24 h. Cell viability was assessed using a CellTiter 96 AQueous One Solution (MTS) Assay (Promega, Madison, Wis., USA) according to the manufacturer's protocol. The UV absorbance was measured at 490 nm using a Labsystems Multiskan Plus microplate reader (Labsystems, Finland). Mean cell viabilities were determined relative to a negative control (untreated cells) and a positive control (0.1% Triton-X, Sigma-Aldrich).

Modeling of the Monomer Self-Assembly

We modeled by atomistic molecular dynamics (MD) simulations individual linear, PCL3.5K-mPEG2K and PCL3.5K-mPEG16K, and branched, PCL3.5K-G3-mPEG2K and PCL14K-G3-mPEG2K copolymers in water. Separately, we modeled micellar assemblies of hydrated PCL3.5K-mPEG2K, PCL3.5K-G3-mPEG2K, and PCL14K-G3-mPEGK copolymers with different aggregation numbers, $N_{agg}$. We used the NAMD package[51] and the CHARMM force field (CHARMM27, C35r revision for ethers, and general force field).[52] In all the simulations, the Langevin damping constant of $\gamma_{Lang}=0.01$ $ps^{-1}$ was used to achieve a faster relaxation. Non-bonded interactions were calculated using the cut-off distance of d=12 Å. Long-range electrostatic interactions were calculated by the PME method[53] and the MD integration timestep was set to 2 fs.

Figure 17:
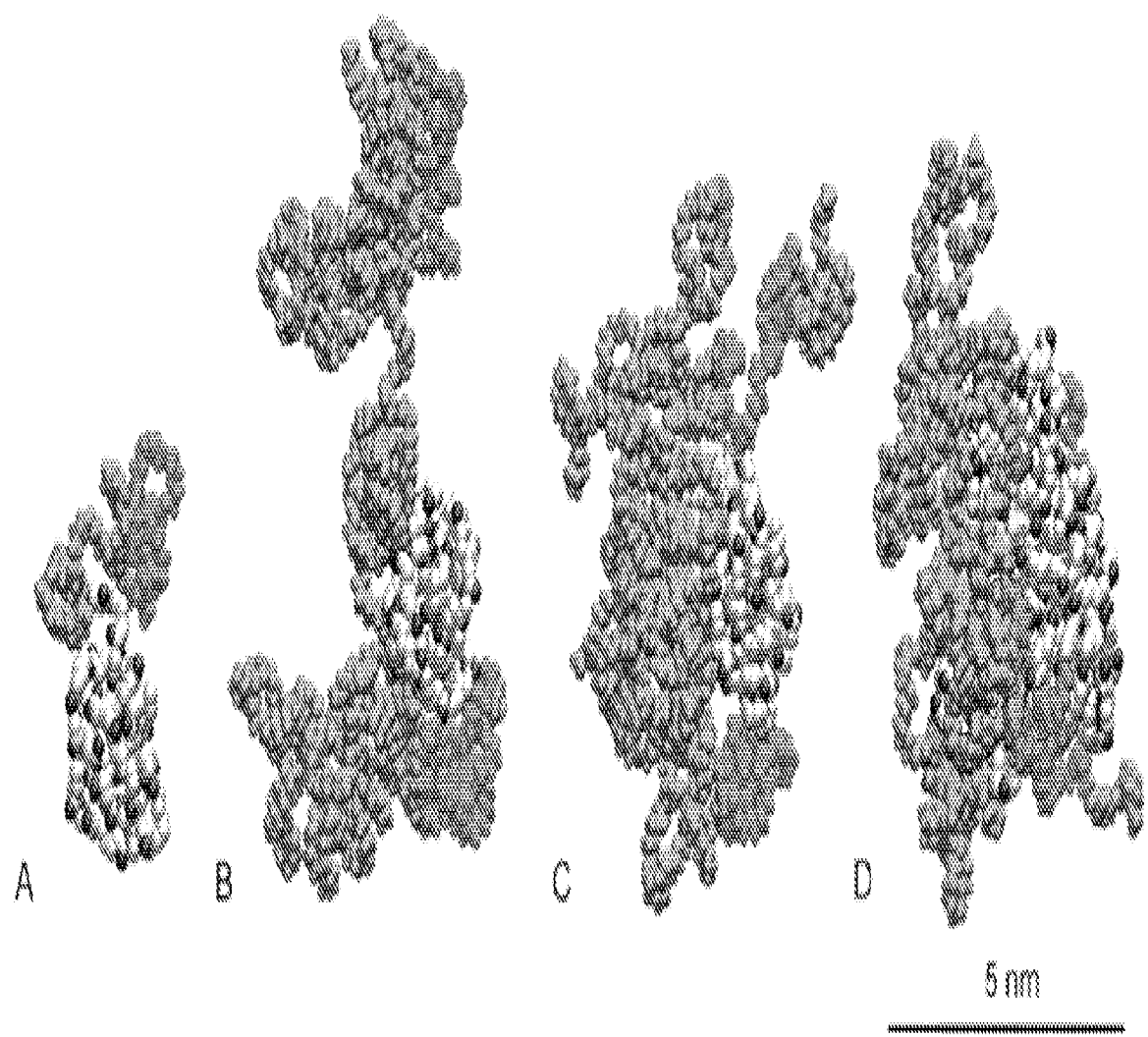
FIG. 17 shows equilibrated conformations of individual (Panel A) PCL3.5K-mPEG2K, (Panel B) PCL3.5K-mPEG16K, (Panel C) PCL3.5K-G3-mPEG2K, and (Panel D) PCL14K-G3-mPEG2K molecules in water (PCL shown in white/black; G3-dendron: hidden in middle in Panel C and D; PEG shown in grey). These structures represent the in-solution morphology of each individual copolymer when they are not packed into micelles. Water is not shown for clarity. Panel E shows equilibrated conformations of the individual PCL3.5K-G3-mPEG2K copolymers in the PCL3.5K-G3-mPEG2K micelle with 14 copolymers taken from FIG. 11 (Panel A).
Figure 17E:
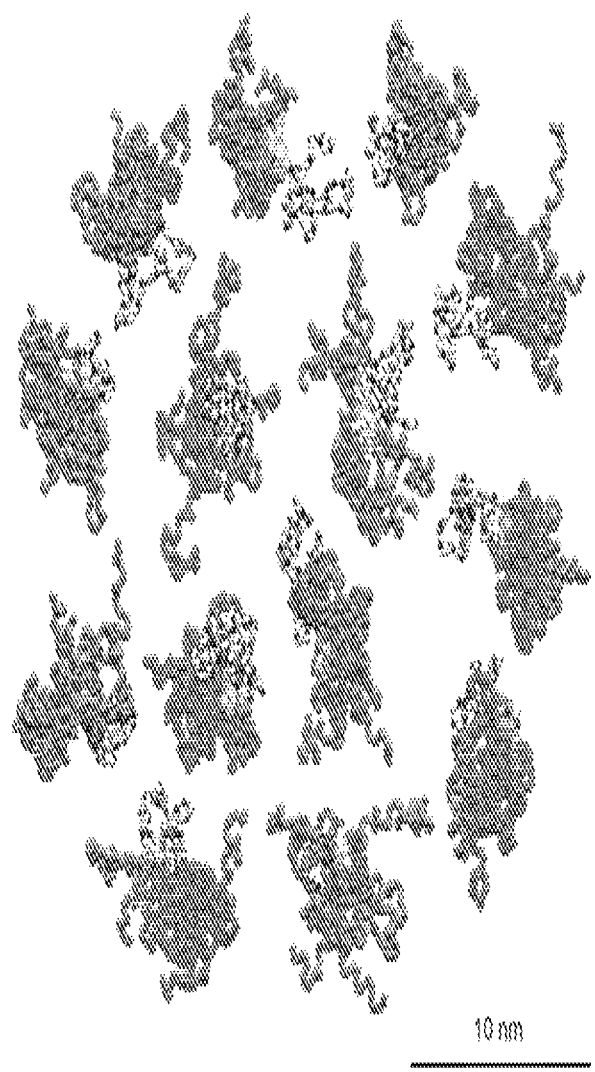

The individual copolymer molecules were solvated and equilibrated for ~5-7 ns in TIP3P water, using the NPT ensemble (VMD)[54], with periodic boundary conditions applied (P=1 bar and T=300 K). The obtained results are shown in FIG. 2b. We also studied the conformations of individual copolymers fully equilibrated in water, using the same conditions. In the equilibration of PCL3.5K-mPEG2K, PCL3.5K-mPEG16K, PCL3.5K-G3-mPEG2K and PCL14K-G3-mPEG2K, a force of F=0.01 kcal/mol/Å was applied to several atoms of the PEG chains, directing toward the hydrophobic PCL core. After ~0.2 ns, the PEG chains were collapsed on the hydrophobic cores. Then, we stopped the force and equilibrated the monomers for another 10 ns. The equilibrated conformations of the copolymers are shown in FIG. 17 (Panels A-D). FIG. 17 (Panel E) shows equilibrated conformations of the individual PCL3.5K-G3-mPEG2K copolymers in the PCL3.5K-G3-mPEG2K micelle with 14 copolymers taken from FIG. 11 (Panel A). Each of the 14 copolymers that form the micelle was translated from their packed configuration and otherwise was not changed. The packed morphology of each of the PCL3.5K-G3-mPEG2K copolymers changes from the largely globular shape, as observed in FIG. 17E, to a significantly conical shape, resembling those in FIG. 11 (Panel A). This conformational change aids in the formation of spherical self-assemblies with fully PEGylated surfaces, as observed in FIG. 11 (Panel A).

Figure 18:
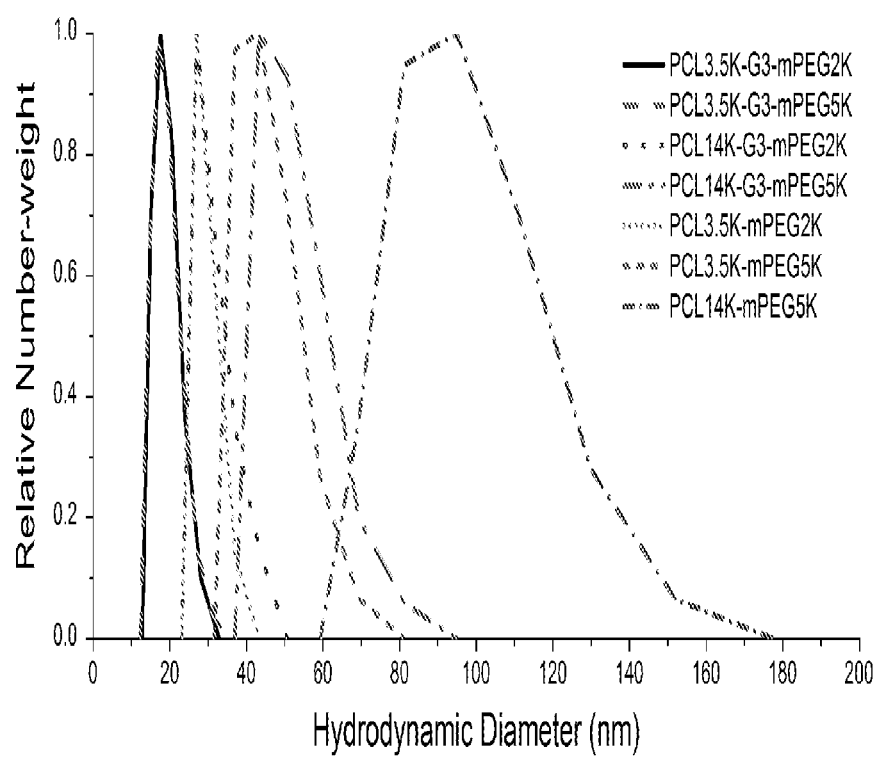
FIG. 18 shows measurements of hydrodynamic diameter using dynamic light scattering (DLS): PCL3.5K-G3-mPEG2K (18.6±3.5 nm); PCL3.5K-G3-mPEG5K (18.3±3.7 nm); PCL14K-G3-mPEG2K (30.3±4.9 nm); PCL14K-G3-mPEG5K (49.8±8.3 nm); PCL3.5K-mPEG2K (29.4±3.2 nm); PCL3.5K-mPEG5K (44.4±9.4 nm); PCL14K-mPEG5K (94.6±16.3 nm).

In the study of micellar assemblies, the monomers were initially spherically distributed by our codes and hydrated in cells containing 30,000-530,000 atoms, with periodic boundary conditions applied. After short minimizations, the systems were heated to T=400 K for fast reorganization, while the volume was kept constant. At the same time, the central force of $\vec{F}(\vec{r})=k\vec{r}$ with k=1.0 kcal/mol/Å was applied to several atoms along the PCL chains of all the copolymers, in order to accelerate aggregation of the micellar core. After 1 ns, the systems were cooled to T=300 K, and equilibrated at P=1 bar for ~4-5 ns. The obtained micelles are shown in FIG. 3b. In order to better understand the conformations of individual PCL3.5K-G3-mPEG2K molecules self-assembled in the micelle, we disintegrated the 14 PCL3.5K-G3-mPEG2K micelle using VMD[11] without changing the conformation of the individual copolymer, as shown in FIG. 18.

We also estimate the approximate entropic cost in the self-assembly of linear monomers, where it is assumed that PEG chains can be described as ideal chains.[55] An ideal chain of length L is comprised of n segments of statistical length l, so that L=ln. When placed in a good solvent (such as water), the ideal chain swells to maximize the number of polymer-fluid contacts. Configurations of the ideal chain can be characterized by a probability distribution function that depends on the chain end-to-end (e-t-e) distance. An ideal chain has a well-defined average e-t-e distance $<r>=ln^{1/2}$, which is associated with minimum (configuration) free energy of the polymer. When the ideal (PEG) chain becomes confined during the self-assembly process, its average e-t-e distance will increase and the free energy cost associated with this extension is purely entropic. Entropy of a freely jointed chain with a given e-t-e distance is proportional to the logarithm of the number of chain configurations for that e-t-e distance. This is in turn is proportional to the probability of the PEG having this e-t-e distance. The entropy difference between PEG chains in a given conformation with different e-t-e extensions is given by[55] $\Delta S=S-S_1=k_B b^2 (r_1^2-r^2)$, where S and $S_1$ are configurational entropies associated with the e-t-e extensions r and $r_1$, $k_B$ is the Boltzmann constant and $b^2=3/(2 nl^2)$. For PCL3.5K-mPEG16K, the PEG block has n=363 repeating units ($-CH_2CH_2O-$), each of the length l is approximately 3.68 Å. In water, the average e-t-e distance of this polymer is $<r>=ln^{1/2}\approx 70$ Å. If we assume that due to steric confinement the e-t-e distance of the chains in the micelle is extended by 50% from the above value of $<r>$, the entropic cost for this extension is $\approx 1.11$ kcal/mol $\approx 1.9$ $k_B T$. Since every chain forming a micelle needs to pay this configurational entropy cost, the micelle formation is not favorable for polymers with long hydrophilic blocks, but in short chains attached to dendrons this entropic costs is absent. We can use the fact that the Gibbs energy associated with the monomer self-assembly is given by $\Delta G=\Delta H-T \Delta S$, where $\Delta H$ is the related enthalpy change. We can immediately see that, for the same $\Delta H$ (hydrophobic binding in the core), long linear amphiphilic molecules tend to be less stable when self-assembled ($\Delta S>0$) than branched dendron-based amphiphilic molecules ($\Delta S\sim 0$).

Example 3

Alpha-Mangostin was Encapsulated into PCL3.5K-G3-mPEG2K Micelles

A solution of PCL3.5K-G3-mPEG2K and α-mangostin (15% w/w; 15 mg drug/100 mg polymer) was prepared at 10 mg polymer/mL in DMF. The solution was dialyzed for 1 day against a 3.5 KDa membrane in 500 mL $dH_2O$ for each 10 mg of polymer with repeated water changes to remove unencapsulated α-mangostin. After dialysis, the dialysate was centrifuged for 10 min at 4000 RPM to remove any unencapsulated α-mangostin. The supernatant was then collected and lyophilized for 2 days to yield the α-mangostin encapsulated micelles.

Figure 19:
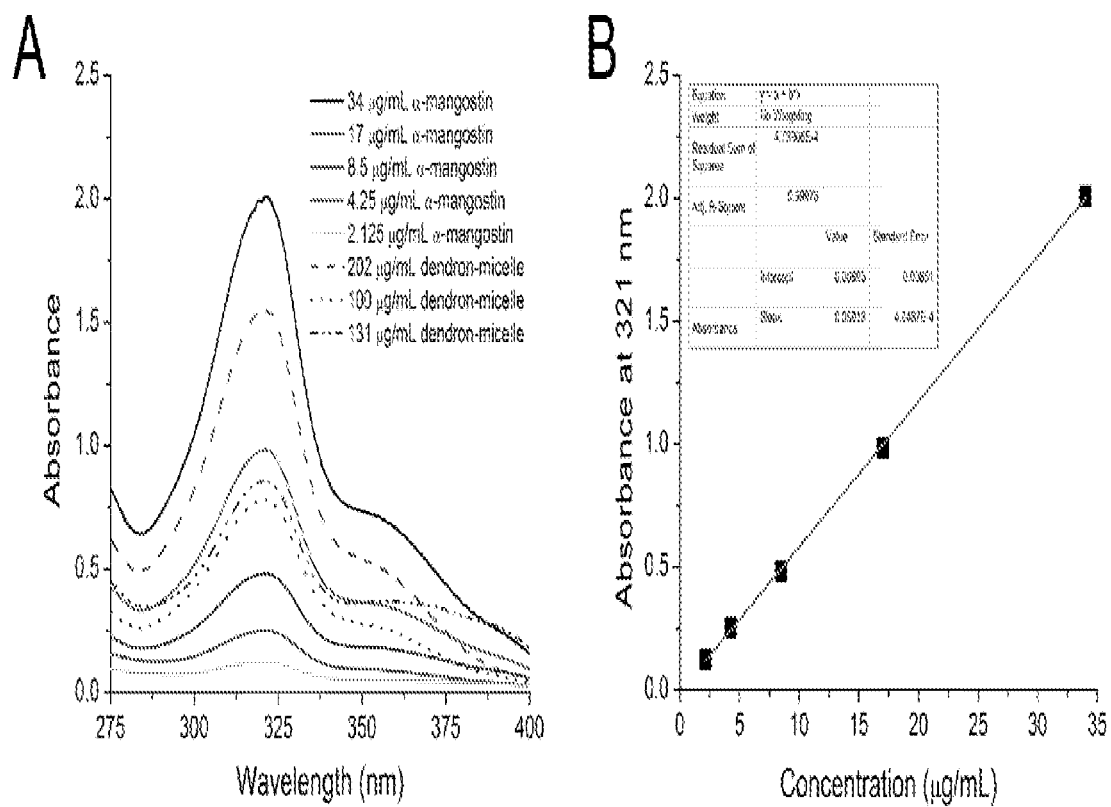
FIG. 19 shows in Panel A, UV/Vis spectra of alpha-mangostin-loaded dendron micelles and free alpha-mangostin, and in Panel B, standard curve based on the UV spectra of free alpha-mangostin. The loading amounts of alpha-mangostin in micelles were calculated based on the standard.

UV/Vis (FIG. 19), loading efficiency and encapsulation efficiency were then calculated. The loading percentage was 12.49±1.2 where Loading %=(Measured α-MS amount/Mass of α-MS loaded micelle)×100(%), while the encapsulation percentage was 83.5±7.7 where Encapsulation (%)=(Measured α-MS amount/Theoretical α-MS loading amount)×100(%).

Figure 20:
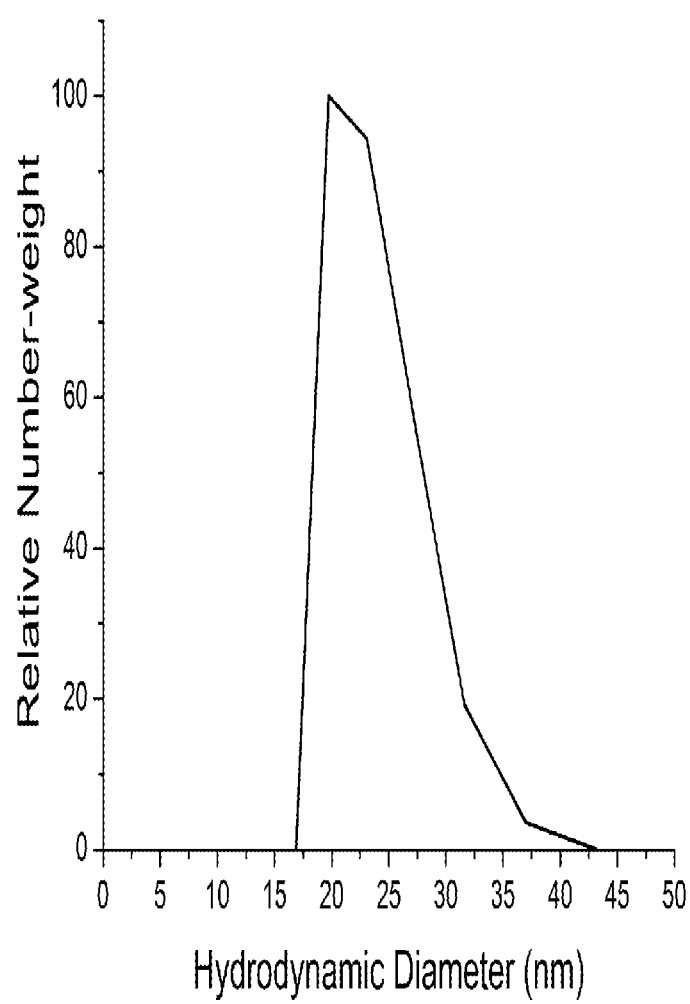
FIG. 20 shows the size distribution of the alpha-mangostin-loaded dendron micelles measured by Dynamic light scattering (DLS).

Next, dynamic light scattering (DLS) analysis of 15% w/w α-mangostin PCL3.5K-G3-mPEG2K micelle (22.7±3.6 nm) was then analyzed. One mg of 15% α-mangostin drug loaded micelles was dissolved in 1 mL of ddH20 and measured by DLS without filtration. The results are shown in FIG. 20.

Figure 21:
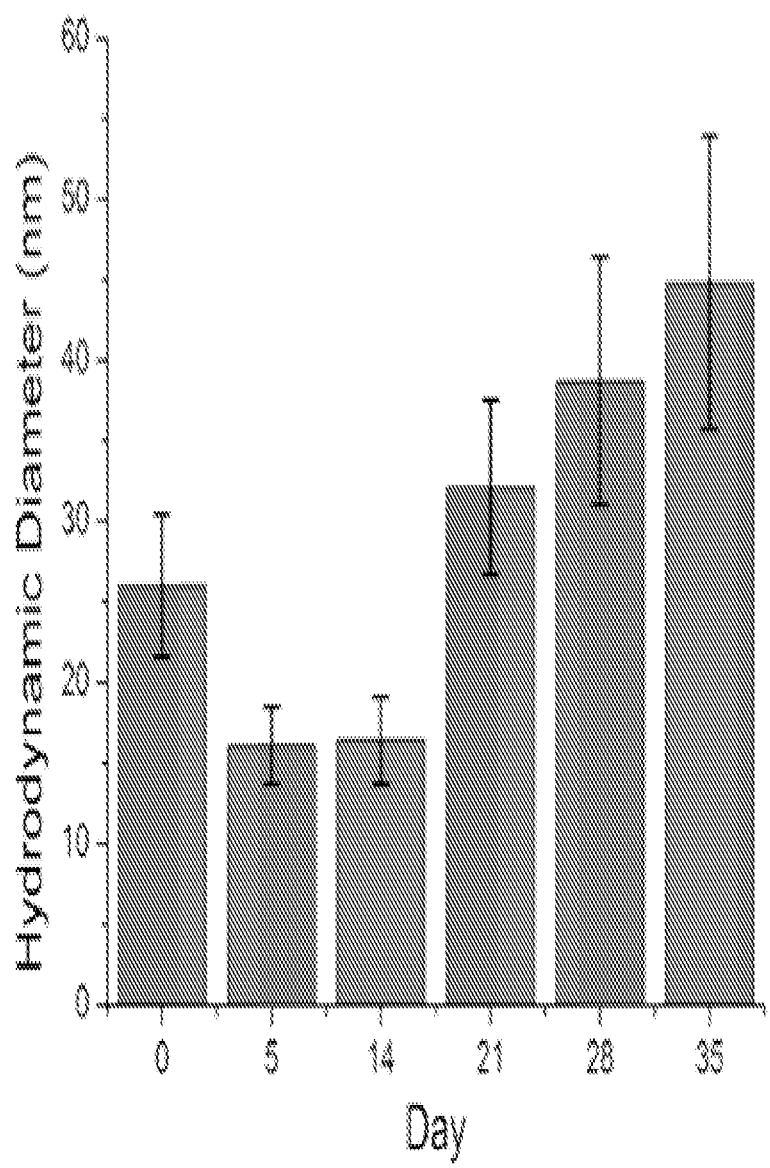
FIG. 21 shows changes in size of the alpha-mangostin-loaded dendron micelles measured by DLS.

Finally, the α-mangostin drug loaded micelles were tested for stability. One mg of 15% α-mangostin drug loaded micelles was dissolved in 1 mL of ddH20 and filtered through a 0.45 um syringe filter. At certain times, the size of the micelles was measured by DLS. The results are shown in FIG. 21.

Example 4

Figure 22:
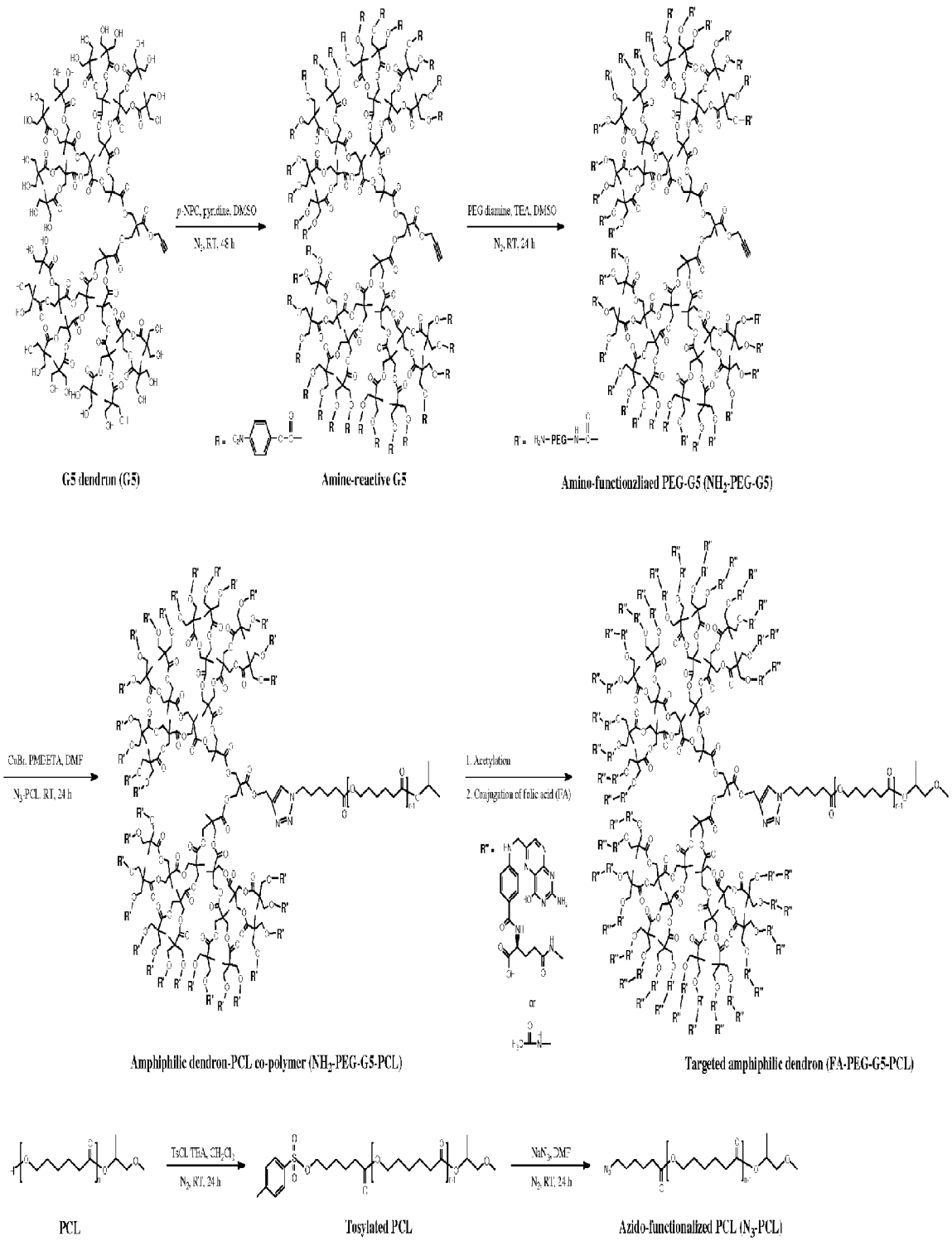
FIG. 22 shows an example of a synthetic route to prepare FA-conjugated amphiphilic dendron.

FA-Conjugated PEG-G5-PCL was Prepared in Four Steps as Shown in FIG. 22

Step 1. Amino-functionalized PEG-G5. G5 dendron (20 mg, 5.47 µmol) and pyridine (138 mg, 1.75 mmol) were dissolved in 10 ml of DMSO and p-NPC (353 mg, 1.75 mmol) was dropwise added to the above solution. The reaction was carried out for 48 h at room temperature under nitrogen atmosphere. The solution was transferred to a pre-swollen membrane (Spectra/Por, MWCO 3.5K), dialyzed against distilled water for 24 h and subsequently lyophilized. To PEG diamine (64-folds .molar excess over activated G5) and TEA (128-fold molar excess over activated G5) dissolved in 20 ml of DMSO, the activated G5 solution was dropwise added and then reacted for 24 h at room temperature under nitrogen atmosphere. After the reaction, the amino-functionalized PEG-G5 was obtained through the same procedure above.

Step 2. Acetylation and FA conjugation of PEG-G5. Both acetylation and FA conjugation on the amino-functionalized PEG-G5 dendron were sequentially performed as previously reported. At first, the PEG-G5 dendron were partially acetylated by reacting with acetic anhydride in anhydrous methanol in the presence of TEA. The reaction was carried out for 24 h at room temperature. The resulting mixture was dialyzed (MWCO 3.5K) first in phosphate buffer at pH 8.0 and then in deionized water. The purified samples were lyophilized and stored at −20° C. For FA conjugation, the obtained product was dissolved in 10 ml of DMSO and the mixture of FA (10 molar excess over dendron) and EDC (10 molar excess over FA) was added dropwise. The conjugation was carried out for 24 h at room temperature under nitrogen atmosphere. After dialysis and lyophilization, FA-PEG-G5 was obtained.

Step 3. Azido-functionalized PCL. Both PCL (0.5 g, 0.013 mmol) and p-toluenesulfonyl chloride (10 mg, 0.091 mmol) were dissolved in 50 ml of methylene chloride. Then, TEA (18 mg, 0.182 mmol) was added dropwise to the mixture and the reaction was performed for 24 h at room temperature under nitrogen atmosphere. The solution was precipitated into cold methanol and dried in vacuo. Tosylated PCL was converted into the azido-functionalized PCL. Sodium azide (10-fold molar excess over tosylated PCL) was added to a solution of tosylated PCL in DMF under nitrogen atmosphere and the reaction was carried out for 24 h at room temperature. DMF was removed using a rotary evaporator and the product was dissolved in methylene chloride and precipitated into cold methanol to give the azido-functionalized PCL.

Step 4. FA-conjugated PEC-G5-PCL. FA-conjugated PEG-G5-PCL was synthesized by coupling azido-PCL to acetylene-dendron via click chemistry. FA-conjugated PEG-G5 was dissolved in 10 ml of dry DMF. After adding CuBr and PMDETA as catalysts, a solution of $N_3$-PCL was added and reacted for 24 h at room temperature. DMF was evaporated completely and the solution was then dissolved in methylene chloride. The solution was precipitated into cold methanol, dried in vacuo and stored at −20° C. before use.

Feed ratio: PCL-N3/FA-PEG-G5/CuBr/PMDETA=1/1/0.2/0.2

Example 5

Supramolecular Structures of Dendron-Based Nanomicelles

Dendron-based nanomicelles (DNM) as a novel targeted drug delivery platform will be prepared by four synthetic procedures; 1) PEGylation of dendron, 2) Conjugation of targeting ligands, 3) Azido-functionalization of a hydrophobic tail, 4) Preparation of amphiphilic dendron via click chemistry. Each step will be further optimized to control the desired properties of nanomicelles for enhanced therapeutic efficiency. By controlling a relative balance between hydrophobic and hydrophilic components, the obtained amphiphilic dendron (AD) molecules can form various unique structures via self assembly. In one application, the micellar structure of AD will be formed at concentrations above the critical micelle concentration (CMC) under aqueous solutions.[56-58] The copolymer composed of hydrophilic dendron and hydrophobic polyester dissolves in an organic solvent with drugs to be encapsulated. Then, DNMs formed by a dialysis method will be physicochemically characterized and its therapeutic efficacy will be evaluated in vitro and in vivo.

Other supramolecular structures such as gold nanaparticles decorated with functionalized dendrons can be prepared by spontaneous alignment of thiol-contained molecules onto the surface of gold nanoparticles.[59] In order to achieve this surface functionalized nanostructure, an acetylene group of the dendron needs to be modified with heterobifunctional PEG, which possesses both azide and thiol at each end, via click chemistry. Then, the self-assembly layers on the nano-sized gold colloids are formed spontaneously in ethanol solution in the presence of dendron-PEG-SH. Either a vesical or a cylindrical nanostructure can be also created by conjugation of hydrophobic molecules to the dendron. In case of a vesicle type, a longer hydrophobic tail should be chemically attached to a focal point of dendron already functionalized with specific ligands, which allows strong hydrophobic interactions. Based on the estimated size of the dendron head group and the hydrophobic length according to the theory of Israelachvili et al.[60], the supranaolecular architecture of these AD molecules eventually results in the formation of lipid bilayers.[58] A cylindrical shape has a similar aspect but hydrophobic modification should be carried out at the peripheral site of the dendron. Consequently, controlling the ratio of the hydrophobic length to the hydrophilic dendron can lead to cylindrical packing.[61] These two switchable features formed via self-assembly are typically dependent on the hydrophobic block length toward two reactive ends of the dendron (either core or periphery).

While the present invention has been described in terms of specific embodiments, it is understood that variations and modifications will occur to those skilled in the art. Accordingly, only such limitations as appear in the claims should be placed on the invention.

All documents cited in this application are hereby incorporated by reference in their entirety for their disclosure described.

DOCUMENTS CITED 1. (a) N. Wiradharma, Y. Zhang, S. Venkataraman, J. L. Hedrick and Y. Y. Yang, *Nano Today,* 2009, 4, 302; (b) A. Harada and K. Kataoka, *Prog. Polym. Sci.,* 2006, 31, 949.
2. (a) J. N. Israelachvili, D. J. Mitchell and B. W. Ninham, *J. Chem. Soc. Farad. T.* 2, 1976, 72, 1525; (b) G. M. Whitesides, J. P. Mathias and C. T. Seto, *Science,* 1991, 254, 1312.
3. B. M. Rosen, C. J. Wilson, D. A. Wilson, M. Peterca, M. R. Imam and V. Percec, *Chem. Rev.,* 2009, 109, 6275.
4. (a) S. Hong, P. R. Leroueil, I. J. Majoros, B. G. Orr, J. R. Baker, Jr. and M. M. Banaszak Holl, *Chem. Biol.,* 2007, 14, 107; (b) D. Q. McNerny, J. F. Kukowska-Latallo, D. G. Mullen, J. M. Wallace, A. M. Desai, R. Shukla, B. Huang, M. M. Banaszak Holl and J. R. Baker, Jr., *Bioconjug. Chem.,* 2009, 20, 1853; (c) I. Papp, C. Sieben, K. Ludwig, M. Roskamp, C. Bottcher, S. Schlecht, A. Herrmann and R. Haag, *Small,* 2010, 6, 2900; (d) M. A. Kostiainen, G. R. Szilvay, J. Lehtinen, D. K. Smith, M. B. Linder, A. Urtti and O. Ikkala, *ACS Nano,* 2007, 1, 103.
5. Olerlemans, C., Bult, W., et al. (2010) "Polymeric Micelles in Anticancer Therapy: Targeting, Imaging and Triggered Release." *Pharm Res* 27: 2569-2589.
6. Peer, D., J. M. Karp, et al. (2007). "Nanocarriers as an emerging platform for cancer therapy." *Nature Nanotechnology* 2(12): 751-760.
7. Sutton, D., N. Nasongkla, et al. (2007). "Functionalized micellar systems for cancer targeted drug delivery." *Pharmaceutical Research* 24(6): 1029-1046.
8. Israelachvili, J. N., D. J. Mitchell, et al. (1976). "Theory of Self-Assembly of Hydrocarbon Amphiphiles into Micelles and Bilayers." *Journal of the Chemical Society-Faraday Transactions Ii* 72: 1525-1568.
9. Kostiainen, M. A., J. G. Hardy, et al. (2005). "High-affinity multivalent DNA binding by using low-molecular-weight dendrons." *Angewandte Chemie-International Edition* 44(17): 2556-2559.
10. S. Hong, P. R. Leroueil, I. J. Majoros, B. G. Orr, J. R. Baker, Jr., M. M. Banaszak Holl, *Chem Biol* 2007, 14, 107-115.
11. B. M. Rosen, C. J. Wilson, D. A. Wilson, M. Peterea, M. R. Imam, V. Percec, *Chem Rev* 2009, 109, 6275-6540.
12. S. Hong, P. R. Leroueil, I. J. Majoros, B. G. Orr, J. R. Baker Jr. and M. M. Bananszak Holl, *Chemistry & Biology* 2007, 14, 107-115.
13. J. H. Myung, K. A. Gajjar, J. Saric, D. T. Eddington and S. Hong, *Angew. Chem. Int. Ed.* 2011, 50, 1-5.
14. Hong, S., Lemuel!, P. R., Majoros, 1. J., Orr, 13. G., Baker, J. R., Ir, and Banaszak Holl, M. M. (2007) The binding avidity of a nanoparticle-based multivalent targeted drug delivery platform, *Chem Biol* 14, 107-115.
15. Christensen, T., Gooden, D. M., Kung, J. B., and Toone, B. J. (2003) Additivity and the physical basis of multivalency effects: A thermodynamic investigation of the calcium BIDTA interaction, *Journal of The American Chemical Society* 125, 7357-7366.
16. Gestwieki, J. E., Cairo, C. W., Mann, D. A., Owen, R. M., and Kiessling, L. L. (2002) Selective immobilization of multivalent ligands for surface plasmon resonance and fluorescence microscopy, *Analytical Biochemistry* 305, 149-155.
17. Kitov, P. 1., and Bundle, D. R. (2003) On the nature of the multivalency effect: A thermodynamic model, *Journal Of the American Chemical Society* 125, 16271-16284.
18. Qiu, L. Y., and Bae, Y. H. (2006) Polymer architecture and drug delivery, *Pharm Res* 23, 1-30.
19. Hong, S., Bielinska, A. U., Mecke, A., Keszler, 13., Beals, J. L., Shi, X., Balogh, L., Orr, B. G., Baker, J. R., Jr., and Banaszak HolI, M. M. (2004) Interaction of poly(amidoamine) dendrimers with supported lipid bilayers and cells: hole formation and the relation to transport, *Bioconj. Chem.* 15, 774-782.
20. Hong, S., Leroueil, P. R., Janus, E. K., Peters, J. L., Kober, M. M., Islam, M. T., Orr, 13. 0, Baker, J. R., Jr., and Banaszak Holl, M. M. (2006) Interaction of polycationic polymers with supported lipid bilayers and cells: nanoscale hole formation and enhanced membrane permeability, *Bioconjug Chem* 17, 728-734.
21. Leroueil, P. R., Hong, S., Mecke, A., Baker, J. R., Jr., Orr, B. G., and Banaszak Holl, M. M. (2007) Nanoparticle interaction with biological membranes: does nanotechnology present a Janus face?, *Ace Chem Res* 40, 335-342.
22. Parker, N., Turk, M. J., Westrick, B., Lewis, J. D., Low, P. S., and Leamon, C. P. (2005) Polate receptor expression in carcinomas and normal tissues determined by a quantitative radioligand binding assay, *Analytical Biochemistry* 338, 284-293.
23. Low, P. S., Henne, W. A., and Doorneweerd, D. D. (2008) Discovery and development of folic-acid-based receptor targeting for imaging and therapy of cancer and inflammatory diseases, *Acc Chem Res* 41, 120-129.
24. Al-Jamal, K. T., Ramaswamy, C., and Florence, A. T. (2005) Supramolecular structures from dendrons and dendrimers, *Advanced Drug Delivery Reviews* 57, 2238-2270.
25. Kong, H. J., Boontheekul, T, and Mooney, 0.1. (2006) Quantifying the relation between adhesion ligand-receptor bond formation and cell phenotype, *Proc Natl Acad Sci USA* 103, 18534-18539.
26. Nagrath, S., Sequist, L. V., Maheswaran, S., Bell, D. W., Irimia, D., Ulkus, L., Smith, M. R., Kwak, E. L, Digumarthy, S., Muzikansky, A., Ryan, P., Balis, U.1., Tompkins, R, G., Haber, D. A., and Toner, M. (2007) Isolation of rare circulating tumour cells in cancer patients by microchip technology, *Nature* 450, 1235-1239.
27. Hong, S., Lee, D., Zhang, H., Zhang, J. Q., Resviek, J. N., Khademhosseini, A., King, M. R., Langer, R., and Karp, J. M. (2007) Covalent immobilization of p-selectin enhances cell rolling, *Langmuir* 23, 12261-122.68.
28. Z. Ge, J. Hu, F, Huang, S. Liu, *Angew Chain Int Ed Engl* 2009, 48, 1798-1802.
29. C. N. Urbani, C. A. Bell, D. Lonsdale, M.12. Whittaker, M. J. Monteiro, *Macromolecules* 2008, 41, 76-86.
30. (a) H. Nandivada, X. W. Jiang, J Lahann, Adv Mater 2007, 19, 2197-2208; (b) W. H. Binder, R. Sachsenholer, Macromol Rapid Comm 2008, 29, 952-981; (c) C. Hua, C. M. Dung, Y. Wei, Biomacromolecules 2009, 10, 1140-1148; (d) K. D. Bodine, D. Y. Gin, M. S. Gin, J Am Chem Sue 2004, 126, 1638-1639; (e) R. Riva, S. Schmeits, C. Jerome, R. Jerome, P. Lecomte, *Macromolecules* 2007, 40, 796-803.
31. E. R. Gillics, J. M. Frechet, *J Am Chem Soc* 2002, 124, 14137-14146.

32. P. Becher, M. J. Schick, *Nonionic Surfactants Physical Chemistor*, MARCEL DEKKER, New York, 1987.
33. (a) J. B. Liu, F. Q. Zeng, C. Allen, Eur Pharm Biopharm 2007, 65, 309-319; (b) H. L. Sun, B. N. Quo, R. Cheng, F. H. Meng, H. Y. Liu, Z, Y. Zhong, Biomaterials 2009, 30, 6358-6366; (c) C. F. Lu, S. R. Guo, L. Liu, S. Q. Zhang, Z. H. Li, J. R. Gu, *J Polym Sci Pol Phys* 2006, 44, 3406-3417.
34. G. Gaucher, M. H. Dufresne, V. P. Sant, N. Kang, D. Maysinger, J. C. Leroux, *J Control Release* 2005, 109, 169-188.
35. (a) S. Y. Kim, I. L. G. Shin, Y. M. Lee, C. S. Cho, Y. K. Sung, *J Control Release* 1998, 51, 13-22; (b) M. L. Forrest, C. Y. Won, A. W. Malick, C, S. Kwon, *J Control Release* 2006, 110, 370-377.
36. G. B. Zhou, J. Smid, *Langmuir* 1993, 9, 2907-2913.
37. C. Tanford, *The Hydrophobic Effect: Formation of Micelles and Biological Membranes*, Wiley Sons, New York, 1973.
38. (a) L. Yang, X. Qi, P. Litt, A. El Ghzaoui, S. M. Li, *Int J Pharm* 2010, 394, 43-49; (b) T. Riley, S. Stolnik, C. R. Heald, C. D, Xiong, M. C. Garnett, L. Ilium, S. S. Davis, S. C. Purkiss, R. J. Barlow, P. R, Gellert, *Langmuir* 2001, 17, 3168-3174; c) P. Posocco, M. Fermeglia, S. Priel, *J Mater Chem* 2010, 20, 7742-7753.
39. M. Ward, *Mechanical Properties of Solid Polymers*, John Wiley and Sons, New York, 1971.
40. (a) G. M. Whitesides, J. P. Mathias, C. T. Seto, *Science* 1991, 254, 1312-1319; (b) J. N. Israelachvili, B. J. Mitchell, B. W. Ninham, *J Chem Soc Farad T* 2 1976, 72, 1525-1568.
41. (a) T. Chen, Z. Zhang, S. C. Glotzer, Proc Nail Acad Sci USA 2007, 104, 717-722; (b) M. Kellermann, W. Bauer, A. Hirsch, B. Schade, K. Ludwig, C. Bottcher, *Angew Chem Int Ed Engl* 2004, 43, 2959-2962; (c) K. Kratzat, H. Finkelmann, *Langmuir* 1996, 12, 1765-1770.
42. R. Nagarajan, *Langmuir* 2002, 18, 31-38.
43. N. W. Suck, M. H. Lamm, *Langmuir* 2008, 24, 3030-3036.
44. Z. Ge, J. Hu, F. Huang and S. Liu, *Angew. Chem. Int. Ed. Engl.*, 2009, 48, 1798.
45. C. N. Urbani, C. A. Bell, D. Lonsdale, M. R. Whittaker and M. J. Monteiro, *Macromolecules*, 2008, 41, 76.
46. (a) H. S. Yoo and T. G. Park, *J. Control. Release.*, 2001, 70, 63; (b) E. R. Gillies and J. M. Frechet, *J. Am. Chem. Soc.*, 2002, 124, 14137.
47. (a) H. Nandivada, X. W. Jiang and J. Lahann, *Adv Mater*, 2007, 19, 2197; (b) W. H. Binder and R. Sachsenhofer, *Macromol. Rapid. Comm.*, 2008, 29, 952.
48. C. Hua, C. M. Dong and Y. Wei, *Biomacromolecules*, 2009, 10, 1140.
49. (a) K. D. Bodine, D. Y. Gin and M. S. Gin, *J. Am. Chem. Soc.*, 2004, 126, 1638; (b) M. J. Joralemon, R. K. O'Reilly, C. J. Hawker and K. L. Wooley, *J. Am. Chem. Soc.*, 2005, 127, 16892; (c) R. Riva, S. Schmeits, C. Jerome, R. Jerome and P. Lecomte, *Macromolecules*, 2007, 40, 796.
50. M. Wilhelm, C. L. Zhao, Y. C. Wang, R. L. Xu, M. A. Winnik, J. L. Mura, G. Riess and M. D. Croucher, *Macromolecules*, 1991, 24, 1033.
51. J. C. Phillips, R. Braun, W. Wang, J. Gumbart, E. Tajkhorshid, E. VIIIa, C. Chipot, R. D. Skeel, L. Kalé and K. Schulten, *J. Comput. Chem.*, 2005, 26, 1781.
52. (a) A. D. MacKerell, D. Bashford, Bellott, R. L. Dunbrack, J. D. Evanseck, M. J. Field, S. Fischer, J. Gao, H. Guo, S. Ha, D. Joseph-McCarthy, L. Kuchnir, K. Kuczera, F. T. K. Lau, C. Mattos, S. Michnick, T. Ngo, D. T. Nguyen, B. Prodhom, W. E. Reiher, B. Roux, M. Schlenkrich, J. C. Smith, R. Stote, J. Straub, M. Watanabe, J. Wiorkiewicz-Kuczera, D. Yin and M. Karplus, The *Journal of Physical Chemistry B*, 1998, 102, 3586; (b) H. Lee, R. M. Venable, A. D. MacKerell and R. W. Pastor, *Biophysical Journal*, 2008, 95, 1590; (c) K. Vanommeslaeghe, E. Hatcher, C. Acharya, S. Kundu, S. Zhong, J. Shim, E. Darian, O. Guvench, P. Lopes, I. Vorobyov and A. D. Mackerell, *J. Comput. Chem.*, 2010, 31, 671.
53. P. P. Ewald, *Ann. Phys.*, 1921, 64, 253.
54. W. Humphrey, A. Dalke and K. Schulten, *Journal of Molecular Graphics*, 1996, 14, 33.
55. I. M. Ward, *Mechanical Properties of Solid Polymers*, John Wiley and Sons, New York, 1971.
56. Gillies, E. R., Jonsson, T. B., and Frechet, J. M. (2004) Stimuli-responsive supramolecular assemblies of linear-dendritic copolymers, *J Am Chem Soc* 126, 11936-11943.
57. Lee, H. 1, Lee, J. A., Poon, Z., and Hammond, P. T. (2008) Temperature-triggered reversible micellar self-assembly of linear-dendritic block copolymers, *Chem Commun (Camb)*, 3726-3728.
58. Tian, L., Nguyen, P., and Hammond, P. T. (2006) Vesicular self-assembly of comb-dendritic block copolymers, *Chem Commun (Camb)*, 3489-3491.
59. Yoshimoto, K., Hoshino, Y., Ishii, T., and Nagasaki, Y. (2008) Binding enhancement of antigen-functionalized PEGylated gold nanoparticles onto antibody-immobilized surface by increasing the functionalized antigen using alpha-sulfanyl-omega-amino-PEG, *Chem Commun (Camb)*, 5369-5371.
60. Israelachvili, J. (1995) *Intermolecular and Surface Forces*, Academic Press Inc., San Diego.
61. Cho, B. K., Jain, A., Gruner, S. M., and Wiesner, U. (2004) Mesophase structure-mechanical and ionic transport correlations in extended amphiphilic dendrons *Science* 305, 1598-1601.

We claim:

1. A micelle comprising amphiphilic dendron-coils, wherein each amphiphilic dendron-coil comprises a non-peptidyl, hydrophobic core-forming block, a polyester dendron and a poly(ethylene) glycol (PEG) moiety, and wherein the non-peptidyl, hydrophobic core-forming block comprises a linear hydrophobic polymer.

2. The micelle of claim 1 wherein the linear hydrophobic polymer is polycaprolactone (PCL), poly(lactic acid) (PLA), poly(glycolic acid) (PGA) or poly(lactic-co-glycolic acid) (PLGA); wherein the polyester dendron is a generation 3 to generation 5 polyester dendron with either an acetylene or carboxylate core; and wherein the PEG moiety is a methoxy PEG (mPEG) moiety, amine-terminated PEG (PEG-NH$_2$) moiety, acetylated PEG (PEG-Ac) moiety, carboxylated PEG (PEG-COOH) moiety, thiol-terminated PEG (PEG-SH) moiety, N-hydroxysuccinimide-actived PEG (PEG-NHS) moiety, NH$_2$-PEG-NH$_2$ moiety or NH$_2$-PEG-COOH moiety.

3. The micelle of claim 1 or 2 wherein the linear hydrophobic polymer has a molecular weight from about 0.5 kDa to about 20 kDa.

4. The micelle of claim 1 wherein the polyester dendron is a generation 3 (G3) dendron.

5. The micelle of claim 1 wherein the polyester dendron is a generation 4 (G4) dendron.

6. The micelle of claim 1 wherein the polyester dendron is a generation 5 (G5) dendron.

7. The micelle of claim 4 wherein the polyester dendron is a generation 3 polyester-8-hydroxyl-1-acetylene bis-MPA dendron.

8. The micelle of claim 1 wherein the PEG moiety is a methoxy PEG (mPEG) moiety, amine-terminated PEG (PEG-NH$_2$) moiety, acetylated PEG (PEG-Ac) moiety, carboxylated PEG (PEG-COOH) moiety, thiol-terminated PEG (PEG-SH) moiety, N-hydroxysuccinimide-actived PEG (PEG-NHS) moiety, $NH_2$-PEG-$NH_2$ moiety or $NH_2$-PEG-COOH moiety.

9. The micelle of claim 8 wherein the PEG moiety has a molecular weight from about 0.2 kDa to about 5 kDa.

10. The micelle of claim 1 further comprising one or more ligands conjugated to one or more PEG moieties.

11. The micelle of claim 1 further comprising a drug.

12. The micelle of claim 11 wherein the drug is a cancer drug.

13. A composition comprising a micelle comprising amphiphilic dendron-coils, wherein each amphiphilic dendron-coil comprises a non-peptidyl, hydrophobic core-forming block, a polyester dendron and a poly(ethylene) glycol (PEG) moiety and wherein the non-peptidyl, hydrophobic core-forming block comprises a linear hydrophobic polymer.

14. A method of delivering a drug to a patient comprising administering a composition comprising a micelle and a pharmaceutically acceptable carrier,
wherein the micelle comprises amphiphilic dendron-coils and encapsulates the drug, and wherein each amphiphilic dendron-coil comprises a non-peptidyl, hydrophobic core-forming block, a polyester dendron and a poly(ethylene) glycol (PEG) moiety and wherein the non-peptidyl, hydrophobic core-forming block comprises a linear hydrophobic polymer.

15. An amphiphilic dendron-coil comprising a non-peptidyl, hydrophobic core-forming block, a polyester dendron and a poly(ethylene) glycol (PEG) moiety, wherein the non-peptidyl, hydrophobic core-forming block comprises a linear hydrophobic polymer.

16. The amphiphilic dendron-coil of claim 15 further comprising a ligand conjugated to the PEG moiety.

* * * * *